United States Patent [19]
Sum et al.

[11] Patent Number: 5,914,339
[45] Date of Patent: Jun. 22, 1999

[54] SUBSTITUTED 1,3-BENZODIOXOLES

[75] Inventors: Fuk-Wah Sum, Pomona; Adam M. Gilbert, Valley Cottage; George T. Grosu, Pearl River, all of N.Y.; Michael S. Malamas, Jamison, Pa.; Aranapakam M. Venkatesan, Rego Park, N.Y.; Gerardo D. Francisco, Orangeburg, N.Y.

[73] Assignee: American Home Products Corporation, Madison, N.J.

[21] Appl. No.: 08/854,199

[22] Filed: May 9, 1997

Related U.S. Application Data

[60] Provisional application No. 60/017,567, May 14, 1996.
[51] Int. Cl.$^6$ .......................... A61K 31/42; A61K 31/36; C07D 263/06; C07D 317/58
[52] U.S. Cl. .......................... 514/374; 514/465; 548/215; 549/436
[58] Field of Search .......................... 549/436; 548/215; 514/465, 374

[56] References Cited

U.S. PATENT DOCUMENTS

| | | | |
|---|---|---|---|
| 5,061,727 | 10/1991 | Bloom et al. | 514/465 |
| 5,480,908 | 1/1996 | Epstein et al. | 514/465 |
| 5,482,971 | 1/1996 | Epstein et al. | 514/465 |
| 5,488,064 | 1/1996 | Sher | 514/465 |

FOREIGN PATENT DOCUMENTS

| | | |
|---|---|---|
| 9533724 | 12/1995 | WIPO. |
| 9604233 | 2/1996 | WIPO. |

OTHER PUBLICATIONS

Claus, H. T. et al., *Annual Reports in Medicinal Chemistry*, 30:20IV, 189–198 (1995).
Bloom, J.D. et al., *J. Med. Chem.*, 35:3081–3084 (1992).
Largis, E. E. et al., *Drug Development Research*, 32:69–76 (1994).
Bloom, J. D. et al., *Drugs of the Future*, 19(1): 23–26 (1994).

*Primary Examiner*—Bernard Dentz
*Attorney, Agent, or Firm*—Steven R. Eck

[57] ABSTRACT

The present invention provides new compounds having anti-diabetic and/or antihyperglycemia and/or anti-obesity activity, as well as pharmaceutical compositions and methods of treatment utilizing the compounds and processes for making the compounds, the compounds having the formula (II):

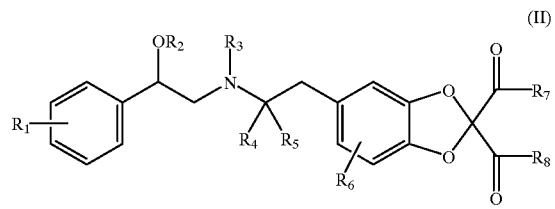

wherein:
$R_1$ and $R_6$ are independently hydrogen, $C_1$ to $C_6$ alkyl, trifluoromethyl, cyano, $C_1$ to $C_6$ alkoxy, or halogen;
$R_2$ is hydrogen or $C_1$ to $C_6$ trialkylsilyl;
$R_3$ is hydrogen or $C_1$ to $C_6$ alkoxycarbonyl;
or $R_2$ and $R_3$ are joined to form a ring:

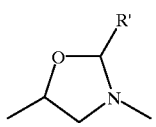

wherein R' is hydrogen, $C_1$ to $C_6$ alkyl, or aryl;
$R_4$ and $R_5$ are independently hydrogen or $C_1$ to $C_6$ alkyl;
$R_7$ and $R_8$ are independently $OR_9$ or $NR_{10}R_{11}$;
$R_9$ is hydrogen, $C_1$ to $C_{12}$ alkyl, $C_1$ to $C_{12}$ cycloalkyl, $C_1$ to $C_{12}$ silylalkyl, aryl, arylalkyl, alkoxyalkyl, heteroaryl, —$CHR_{12}COOR_{13}$, —$CHR_{12}C(O)R_{13}$, —$CHR_{12}CONR_1R_{11}$, —$CHR_{12}OCOOR_{13}$, or —$CHR_{12}OC(O)R_{13}$, with the provision that $R_9$ is not hydrogen in both $R_7$ and $R_8$;
$R_{10}$ and $R_{11}$ are independently hydrogen, $C_1$ to $C_{12}$ alkyl, aralkyl, aryl, furanylalkyl, or alkoxycarbonylalkyl;
$R_{12}$ and $R_{13}$ are independently hydrogen, $C_1$ to $C_{12}$ alkyl, aryl, or aralkyl; and the pharmaceutically acceptable salts thereof, the enantiomers thereof, the racemic mixtures thereof, and the diastereomeric mixtures thereof.

87 Claims, No Drawings

SUBSTITUTED 1,3-BENZODIOXOLES

This application claims the benefit of U.S. Provisional Application No. 60/017,567, filed May 14, 1996.

This invention relates to novel substituted 1,3-benzodioxole compounds which have antidiabetic, antihyperglycemic, and antiobesity properties. The present invention also relates to pharmaceutical compositions containing these compounds, methods for the preparation of these compounds, and methods for the use of these compounds in treating diabetes and/or hyperglycemia and/or obesity in mammals.

BACKGROUND OF THE INVENTION

Bloom, et al., U.S. Pat. No. 5,061,727, disclose substituted 5-(2-((2-aryl-2-hydroxyethyl)amino)propyl)-1,3-benzodioxoles of general formula (I)

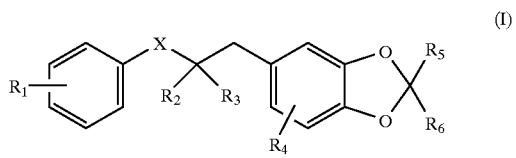

wherein $R_1$ and $R_4$ may be one or more groups which may be the same or different and are selected from the group consisting of hydrogen, $C_1$ to $C_4$ alkyl, $C_1$ to $C_4$ alkoxy, hydroxy, halogen, trifluoromethyl, carboxy, hydroxyalkyl, alkoxycarbonyl, $C_1$ to $C_4$ thioalkyl, sulfonyl and sulfinyl; X is a divalent radical consisting of

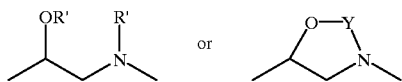

wherein R' is selected from the group consisting of hydrogen, $C_1$ to $C_4$ alkyl and $C_1$ to $C_4$ acyl and Y is selected from the group consisting of carbonyl and thiocarbonyl; $R_2$ and $R_3$ may be the same or different and are selected from the group consisting of hydrogen and $C_1$ to $C_4$ alkyl; $R_5$ and $R_6$ are selected from the group consisting of hydrogen, carboxy, alkoxycarbonyl, hydroxymethyl, —$CH_2OCH_2COOR_7$ and —$CH_2OCH_2CH_2OR_7$, where $R_7$ is hydrogen or $C_1$ to $C_4$ alkyl; with the provision that $R_5$ and $R_6$ may not both be hydrogen; which have antihyperglycemic and antiobesity activity.

The synthesis, antidiabetic effects, and antiobesity effects of (R,R)-5-[2-[[2-(3-chlorophenyl)-2-hydroxyethyl]amino]propyl]-1,3-benzodioxole-2,2-dicarboxylate (which is one of the compounds disclosed by Bloom, et al. in U.S. Pat, No. 5,061,727) are detailed in Bloom, et al. *J. Med. Chem.*, 1992, 35, 3081, Largis, et al. *Drug Dev. Res.*, 1994, 32, 69, and Bloom, et al. *Drugs of the Future*, 1994, 19, 23.

The compounds of the present invention possess greatly increased potency at human $\beta_3$ receptors in comparison to the compounds in Bloom, et al., U.S. Pat. No. 5,061,727. They retain high selectivity for the P3 receptor and show much higher antiobesity and antihyperglycemic activity in animal models than the compounds of the prior art. The compounds have intrinsic activity at human $\beta_3$ receptors and can directly bring about antihyperglycemic and antiobesity effects, but may also be hydrolyzed in vivo to deliver a compound of the type disclosed in Bloom, et al., U.S. Pat. No. 5,061,727 where $R_5$ and $R_6$ are carboxy. Thus the compounds may act as prodrugs. Therefore, the compounds of this invention are useful in treating diabetes, hyperglycemia, and obesity, exhibiting minimal side effects such as heart rate increase and muscle tremor in humans and animals, when formulated into pharmaceutical compositions.

DESCRIPTION OF THE INVENTION

The compounds of the present invention achieve their antidiabetic, antihyperglycemic, and antiobesity effects by acting as selective agonists at $\beta_3$ adrenergic receptors. The stimulation of these receptors on white and brown adipocytes promotes both lipolysis (breakdown of fat) and energy expenditure. Selective stimulation of $\beta_3$ adrenergic receptors is important for chronic treatment. Stimulation of other β-receptors could cause side effects such as increased heart rate ($\beta_1$ effect) and muscle tremor ($\beta_2$ effect). The compounds of the present invention show high selectivity for $\beta_3$ adrenergic receptors.

According to the present invention there are provided new compounds of the formula (II):

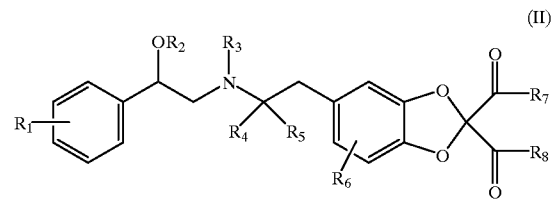

wherein:

$R_1$ and $R_6$ are independently hydrogen, $C_1$ to $C_6$ alkyl, trifluoromethyl, cyano, $C_1$ to $C_6$ alkoxy, or halogen;

$R_2$ is hydrogen or $C_1$ to $C_6$ trialkylsilyl;

$R_3$ is hydrogen or $C_1$ to $C_6$ alkoxycarbonyl;

or $R_2$ and $R_3$ are joined to form a ring:

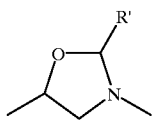

wherein R' is hydrogen, $C_1$ to $C_6$ alkyl, or aryl;

$R_4$ and $R_5$ are independently hydrogen or $C_1$ to $C_6$ alkyl;

$R_7$ and $R_8$ are independently $OR_9$ or $NR_{10}R_{11}$;

$R_9$ is hydrogen, $C_1$ to $C_{12}$ alkyl, $C_1$ to $C_{12}$ cycloalkyl, $C_1$ to $C_{12}$ silylalkyl, aryl, arylalkyl, alkoxyalkyl, heteroaryl, —$CHR_{12}COOR_{13}$, —$CHR_{12}C(O)R_{13}$, —$CHR_{12}CONR_{10}R_{11}$, —$CHR_{12}OCOOR_{13}$, or —$CHR_{12}OC(O)R_{13}$, with the provision that $R_9$ is not hydrogen in both $R_7$ and $R_8$;

$R_{10}$ and $R_{11}$ are independently hydrogen, $C_1$ to $C_{12}$ alkyl, arylalkyl, aryl, furanylalkyl, or alkoxycarbonylalkyl;

$R_{12}$ and $R_{13}$ are independently hydrogen, $C_1$ to $C_{12}$ alkyl, aryl, or aralkyl; and the pharmaceutically acceptable salts thereof, the enantiomers thereof, the racemic mixtures thereof, and the diastereomeric mixtures thereof.

In the description above, aryl may be phenyl or napthyl; arylalkyl may be phenyl $C_1$ to $C_6$ alkyl or naphthyl $C_1$ to $C_6$ alkyl; alkoxy alkyl may be $C_1$ to $C_6$ alkoxy $C_1$ to $C_6$ alkyl; and heteroaryl may be pyridyl, thiophenyl, furanyl, imidazolyl, oxazolyl, or thiazolyl. Further, the phenyl $C_1$ to $C_6$ alkyl group may be optionally substituted by one or more substituents selected from F, Cl, Br, $CH_3$ or $CF_3$.

The most preferred compounds of this invention are the following and the pharmaceutically acceptable salts thereof:

5-{2-[2-(3-chloro-phenyl)-2-hydroxy-ethylamino]-propyl}-benzo[1,3]dioxole-2,2-dicarboxylic acid bis-(2-methoxy-ethyl) ester;

5-{2-[2-(3-chloro-phenyl)-2-hydroxy-ethylamino]-propyl}-benzo[1,3]dioxole-2,2-dicarboxylic acid diphenethyl ester;

5-{2-[2-(3-chloro-phenyl)-2-hydroxy-ethylamino]-propyl}-benzo[1,3]dioxole-2,2-dicarboxylic acid bis-(2-butoxy-ethyl) ester;

5-{2-[2-(3-chloro-phenyl)-2-hydroxy-ethylamino]-propyl}-benzo[1,3]dioxole-2,2-dicarboxylic acid bis-(2-phenoxy-ethyl) ester;

5-{2-[2-(3-chloro-phenyl)-2-hydroxy-ethylamino]-propyl}-benzo[1,3]dioxole-2,2-dicarboxylic acid bis-(2-ethoxy-ethyl) ester;

5-{2-[2-(3-chloro-phenyl)-2-hydroxy-ethylamino]-propyl}-benzo[1,3]dioxole-2,2-dicarboxylic acid bis-(2-tert-butoxy-ethyl) ester;

5-{2-[2-(3-chloro-phenyl)-2-hydroxy-ethylamino]-propyl}-benzo[1,3]dioxole-2,2-dicarboxylic acid (2-tert-butoxy-ethyl) ester;

5-{2-[2-(3-chloro-phenyl)-2-hydroxy-ethylamino]-propyl}-benzo[1,3]dioxole-2,2-dicarboxylic acid bis-(2-isobutoxy-ethyl) ester;

5-{2-[2-(3-chloro-phenyl)-2-hydroxy-ethylamino]-propyl}-benzo[1,3]dioxole-2,2-dicarboxylic acid bis-(benzyl) ester;

5-{2-[2-(3-chloro-phenyl)-2-hydroxy-ethylamino]-propyl}-benzo[1,3]dioxole-2,2-dicarboxylic acid bis-(cyclohexyl) ester;

5-{2-[2-(3-chloro-phenyl)-2-hydroxy-ethylamino]-propyl}-benzo[1,3]dioxole-2,2-dicarboxylic acid bis-(cyclopentyl) ester;

5-{2-[2-(3-chloro-phenyl)-2-hydroxy-ethylamino]-propyl)-benzo[1,3]dioxole-2,2-dicarboxylic acid dioctyl ester;

5-{2-[2-(3-chloro-phenyl)-2-hydroxy-ethylamino]-propyl}-benzo[1,3]dioxole-2,2-dicarboxylic acid dipentyl ester;

5-{2-[2-(3-chloro-phenyl)-2-hydroxy-ethylamino]-propyl}-benzo[1,3]dioxole-2,2-dicarboxylic acid dihexyl ester;

carbonic acid 3-chloro-benzyl ester 2-(3-chloro-benzyloxycarbonyloxy)-4-{2-[2-(3-chloro-phenyl)-2-hydroxy-ethylamino]-propyl)-phenyl ester;

5-{2-[2-(3-chloro-phenyl)-2-hydroxy-ethylamino]-propyl}-benzo[1,3]dioxole-2,2-dicarboxylic acid bis-(1-phenyl-ethyl) ester;

5-{2-[2-(3-chloro-phenyl)-2-hydroxy-ethylamino]-propyl}-benzo[1,3]dioxole-2,2-dicarboxylic acid diheptyl ester;

5-{2-[2-(3-chloro-phenyl)-2-hydroxy-ethylamino]-propyl}-benzo[1,3]dioxole-2,2-dicarboxylic acid dinonyl ester;

5-{2-[2-(3-chloro-phenyl)-2-hydroxy-ethylamino]-propyl}-benzo[1,3]dioxole-2,2-dicarboxylic acid bis-decyl ester;

5-{2-[2-(3-chloro-phenyl)-2-hydroxy-ethylamino]-propyl}-benzo[1,3]dioxole-2,2-dicarboxylic acid didodecyl ester;

5-{2-[2-(3-chloro-phenyl)-2-hydroxy-ethylamino]-propyl}-benzo[1,3]dioxole-2,2-dicarboxylic acid bis-(2-isopropoxy-ethyl)ester;

5-{2-[2-(3-chloro-phenyl)-2-hydroxy-ethylamino]-propyl}-benzo[1,3]dioxole-2,2-dicarboxylic acid isopropyl ester;

5-{2-[2-(3-chloro-phenyl)-2-hydroxy-ethylamino]-propyl}-benzo[1,3]dioxole-2,2-dicarboxylic acid ethyl ester;

5-{2-[2-(3-chloro-phenyl)-2-hydroxy-ethylamino]-propyl}-benzo[1,3]dioxole-2,2-dicarboxylic acid bis-methoxycarbonylmethyl ester;

5-{2-[2-(3-chloro-phenyl)-2-hydroxy-ethylamino]-propyl}-benzo[1,3]dioxole-2,2-dicarboxylic acid bis-propoxycarbonylmethyl ester;

5-{2-[2-(3-chloro-phenyl)-2-hydroxy-ethylamino]-propyl}-benzo[1,3]dioxole-2,2-dicarboxylic acid bis-(1-methoxycarbonyl-ethyl) ester;

5-{2-[2-(3-chloro-phenyl)-2-hydroxy-ethylamino]-propyl}-benzo[1,3]dioxole-2,2-dicarboxylic acid bis-isopropoxycarbonylmethyl ester;

5-{2-[2-(3-chloro-phenyl)-2-hydroxy-ethylamino]-propyl}-benzo[1,3]dioxole-2,2-dicarboxylic acid bis-ethoxycarbonylmethyl ester;

5-{2-[2-(3-chloro-phenyl)-2-hydroxy-ethylamino]-propyl}-benzo[1,3]dioxole-2,2-dicarboxylic acid bis-(1-ethoxycarbonyl-ethyl) ester;

5-{2-[2-(3-chloro-phenyl)-2-hydroxy-ethylamino]-propyl}-benzo[1,3]dioxole-2,2-dicarboxylic acid bis-trimethylsilanylmethyl ester;

5-{2-[2-(3-chloro-phenyl)-2-hydroxy-ethylamino]-propyl}-benzo[1,3]dioxole-2,2-dicarboxylic acid bis-(2-trimethylsilanyl-ethyl) ester;

5-{2-[2-(3-chloro-phenyl)-2-hydroxy-ethylamino]-propyl}-benzo[1,3]dioxole-2,2-dicarboxylic acid bis-(3-trimethylsilanyl-propyl) ester;

5-{2-[2-(3-chloro-phenyl)-2-hydroxy-ethylamino]-propyl}-benzo[1,3]dioxole-2,2-dicarboxylic acid bis-(3,3-dimethyl-butyl) ester;

5-{2-[2-(3-chloro-phenyl)-2-hydroxy-ethylamino]-propyl}-benzo[1,3]dioxole-2,2-dicarboxylic acid bis-cyclohexylmethyl ester;

5-{2-[2-(3-chloro-phenyl)-2-hydroxy-ethylamino]-propyl}-benzo[1,3]dioxole-2,2-dicarboxylic acid bis-(4-methyl-pentyl) ester;

5-{2-[2-(3-chloro-phenyl)-2-hydroxy-ethylamino]-propyl}-benzo[1,3]dioxole-2,2-dicarboxylic acid bis-(2-cyclohexyl-ethyl) ester;

5-{2-[2-(3-chloro-phenyl)-2-hydroxy-ethylamino]-propyl}-benzo[1,3]dioxole-2,2-dicarboxylic acid bis-(3-cyclopentyl-propyl) ester;

5-{2-[2-(3-chloro-phenyl)-2-hydroxy-ethylamino]-propyl}-benzo[1,3]dioxole-2,2-dicarboxylic acid bis-cyclopropylmethyl ester;

5-{2-[2-(3-chloro-phenyl)-2-hydroxy-ethylamino]-propyl}-benzo[1,3]dioxole-2,2-dicarboxylic acid bis-(1-methyl-cyclopropylmethyl) ester;

5-{2-[2-(3-chloro-phenyl)-2-hydroxy-ethylamino]-propyl}-benzo[1,3]dioxole-2,2-dicarboxylic acid bis-cyclobutylmethyl ester;

5-{2-[2-(3-chloro-phenyl)-2-hydroxy-ethylamino]-propyl}-benzo[1,3]dioxole-2,2-dicarboxylic acid bis-(2-cyclopentyl-ethyl) ester;

5-{2-[2-(3-chloro-phenyl)-2-hydroxy-ethylamino] propyl}benzo[1,3]dioxole-2,2-dicarboxylic acid bis-acetoxymethyl ester;

5-{2-[2-(3-chloro-phenyl)-2-hydroxy-ethylamino] propyl}benzo[1,3]dioxole-2,2-dicarboxylic acid bis-propionyloxymethyl ester;

5-{2-[2-(3-chloro-phenyl)-2-hydroxy-ethylamino] propyl}benzo[1,3]dioxole-2,2-dicarboxylic acid bis-butyryloxymethyl ester;

5-{2-[2-(3-chloro-phenyl)-2-hydroxy-ethylamino] propyl}benzo[1,3]dioxole-2,2-dicarboxylic acid bis-isobutyryloxymethyl ester;

5-{2-[2-(3-chloro-phenyl)-2-hydroxy-ethylamino] propyl}benzo[1,3]dioxole-2,2-dicarboxylic acid bis-heptanoyloxymethyl ester;

5-{2-[2-(3-chloro-phenyl)-2-hydroxy-ethylamino] propyl}benzo[1,3]dioxole-2,2-dicarboxylic acid bis-(4-methyl-pentanoyloxymethyl) ester;

5-{2-[2-(3-chloro-phenyl)-2-hydroxy-ethylamino]
propyl}benzo[1,3]dioxole-2,2-dicarboxylic acid bis-hexanoyloxymethyl ester;

5-{2-[2-(3-chloro-phenyl)-2-hydroxy-ethylamino]
propyl}benzo[1,3]dioxole-2,2-dicarboxylic acid bis-(2,2-dimethyl-propionyloxymethyl) ester;

5-{2-[2-(3-chloro-phenyl)-2-hydroxy-ethylamino]
propyl}benzo[1,3]dioxole-2,2-dicarboxylic acid bis cyclohexanecarbonyloxymethyl ester;

5-{2-[2-(3-chloro-phenyl)-2-hydroxy-ethylamino]
propyl}benzo[1,3]dioxole-2,2-dicarboxylic acid bis-(1-propionyloxy-ethyl) ester;

5-{2-[2-(3-chloro-phenyl)-2-hydroxy-ethylamino]
propyl}benzo[1,3]dioxole-2,2-dicarboxylic acid bis-[1-(2,2-dimethyl-propionyloxy-ethyl) ester;

5-{2-[2-(3-chloro-phenyl)-2-hydroxy-ethylamino]
propyl}benzo[1,3]dioxole-2,2-dicarboxylic acid bis-(3,3-dimethyl-butyryloxymethyl) ester;

5-{2-[2-(3-chloro-phenyl)-2-hydroxy-ethylamino]
propyl}benzo[1,3]dioxole-2,2-dicarboxylic acid bis-[1-(3,3-dimethyl-butyryloxy)-ethyl)}ester;

5-{2-[2-(3-chloro-phenyl)-2-hydroxy-ethylamino]
propyl}benzo[1,3]dioxole-2,2-dicarboxylic acid bis-(3-cyclopentyl-propionyloxymethyl) ester;

5-{2-[2-(3-chloro-phenyl)-2-hydroxy-ethylamino]
propyl}benzo[1,3]dioxole-2,2-dicarboxylic acid bis-benzoyloxymethyl ester;

5-{2-[2-(3-chloro-phenyl)-2-hydroxy-ethylamino]
propyl}benzo[1,3]dioxole-2,2-dicarboxylic acid bis-(benzoyloxy-ethyl) ester;

5-{2-[2-(3-chloro-phenyl)-2-hydroxy-ethylamino]
propyl}benzo[1,3]dioxole-2,2-dicarboxylic acid bis-(2,2-dimethyl-butyryloxymethyl) ester;

5-{2-[2-(3-chloro-phenyl)-2-hydroxy-ethylamino]-propyl}-benzo[1,3]dioxole-2,2-dicarboxylic acid bis-amide;

5-{2-[2-(3-chloro-phenyl)-2-hydroxy-ethylamino]-propyl}-benzo[1,3]dioxole-2,2-dicarboxylic acid bis-2-propyl amide;

5-{2-[2-(3-chloro-phenyl)-2-hydroxy-ethylamino]-propyl}-benzo[1,3]dioxole-2,2-dicarboxylic acid bis-n-butyl amide;

5-{2-[2-(3-chloro-phenyl)-2-hydroxy-ethylamino]-propyl}-benzo[1,3]dioxole-2,2-dicarboxylic acid bis-phenylmethyl amide;

5-{2-[2-(3-chloro-phenyl)-2-hydroxy-ethylamino]-propyl}-benzo[1,3]dioxole-2,2-dicarboxylic acid bis-(2-furanylmethyl) amide;

5-{2-[2-(3-chloro-phenyl)-2-hydroxy-ethylamino]-propyl}-benzo[1,3]dioxole-2,2-dicarboxylic acid bis-(glycine ethyl ester) amide;

5-{2-[2-(3-chloro-phenyl)-3-oxazolidinyl]-propyl}-benzo[1,3]dioxole-2,2-dicarboxylic acid;

Also according to the present invention there is provided a method of treating diabetes and/or hyperglycemia and/or obesity in humans or other mammals which comprises administering to a human or other mammal an antiobesity effective amount or an antihyperglycemia effective amount of a compound of the present invention.

It is understood that the effective dosage of the active compounds of this invention may vary depending upon the particular compound utilized, the mode of administration, the condition, and severity thereof, of the condition being treated, as well as the various physical factors related to the individual being treated. For treating diabetes mellitus and/or hyperglycemia generally satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. This regimen may be adjusted to provide the optimal therapeutic response.

When treating obesity, in conjunction with diabetes and/or hyperglycemia, or alone, generally satisfactory results can be obtained when the compounds of this invention are administered at a daily dosage of from about 0.1 mg to about 1 mg per kg of body weight, preferably given in divided doses two to six times per day or in a sustained release form. For most large mammals, the total daily dosage is from about 3.5 to about 140 mg, preferably from about 3.5 to about 5 mg. In the case of a 70 kg human adult, the total daily dose will generally be from about 7 mg to about 70 mg and may be adjusted to provide the optimal therapeutic result.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elexir may contain, in addition to the active ingredients, sucrose as a sweetening agent, methyl and propyl parabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of micoorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, domestic pets and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. The method of the present invention has several advantages; for the pet owner or veterinarian who wishes to increase leanness and trim unwanted fat from pet animals, the present invention provides the means by which this can be accomplished. For the poultry and swine raisers, using the method of the present invention yields leaner animals which command higher prices from the meat industry.

Further, according to the present invention there are provided pharmaceutical compositions of matter comprising an effective amount of the compounds of the present invention in combination with a pharmaceutically acceptable carrier; as well as a method for increasing the content of lean meat in edible animals, which comprises administering to edible mammals an effective amount of the compound.

Also according to the present invention there are provided processes for producing the compounds of the present invention.

PROCESS OF THE INVENTION

The compounds of the present invention may be prepared according to one of the general processes outlined below.

As outlined in Scheme I, a disodium carboxylate 1 is converted to a disilver carboxylate and treated with an iodo derivative 2 to yield the diester compounds 3 wherein $R_1$, $R_4$, $R_5$, $R_6$, $R_{12}$, and $R_{13}$ are as defined above.

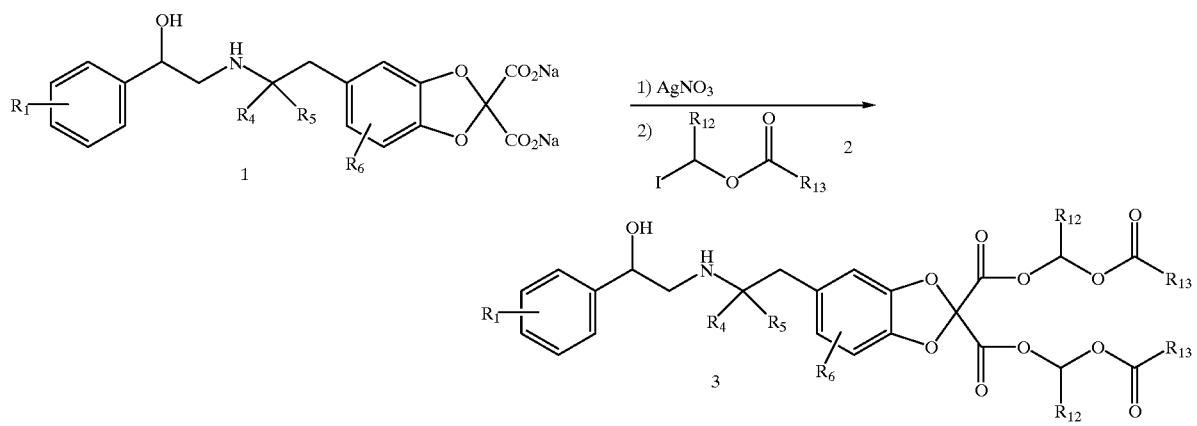

Scheme I

Alternatively, a dicarboxylic acid 4 (Scheme II) is treated with an alcohol $R_9OH$ and an acid catalyst to yield the diester compounds 5 wherein $R_1$, $R_4$, $R_5$, $R_6$, and $R_9$ are as defined above.

Scheme II

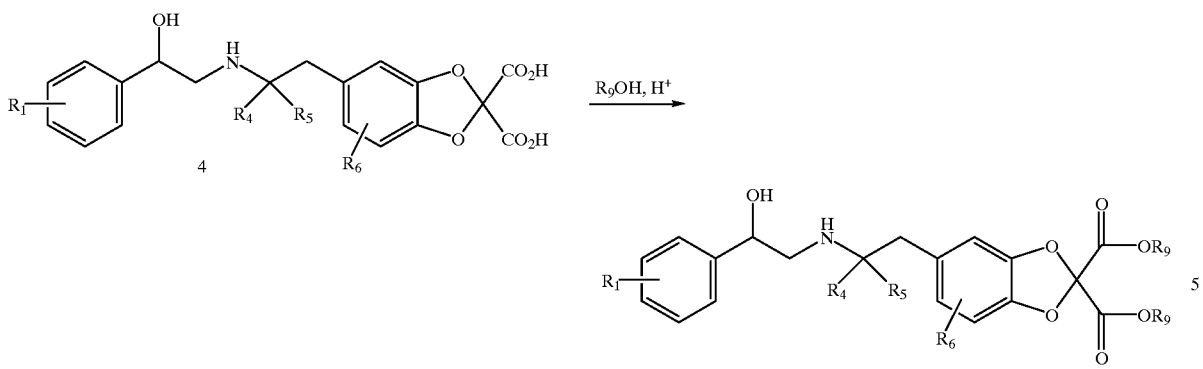

As outlined in Scheme III, the diester compounds 5 can also be produced by protecting the hydroxy and amino groups of compound 6 with $R_2$ and $R_3$ groups, respectively, basic hydrolysis of the ethyl esters, alkylation of the carboxyl groups of compound 7 with an alkylating agent Z-$R_9$, and removing the protecting groups $R_2$ and $R_3$, wherein $R_1$, $R_2$, $R_3$, $R_4$, $R_5$, $R_6$, and $R_9$ are as defined above and Z is Cl, Br, I, methanesulfonate, trifluoromethanesulfonate, or para-toluenesulfonate.

Scheme III

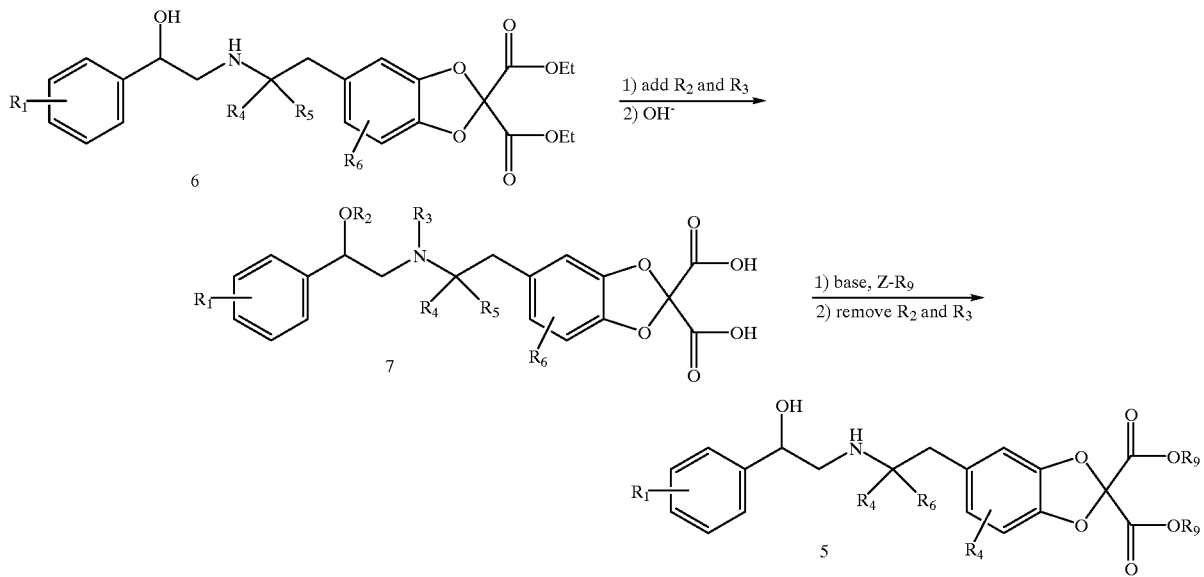

As outlined in Scheme IV, a dicarboxylate 1 is treated with an aldehyde R'CHO to yield the oxazaline compounds 8, wherein $R_1$, $R_4$, $R_5$, $R_6$, and R' are as defined above.

Scheme IV

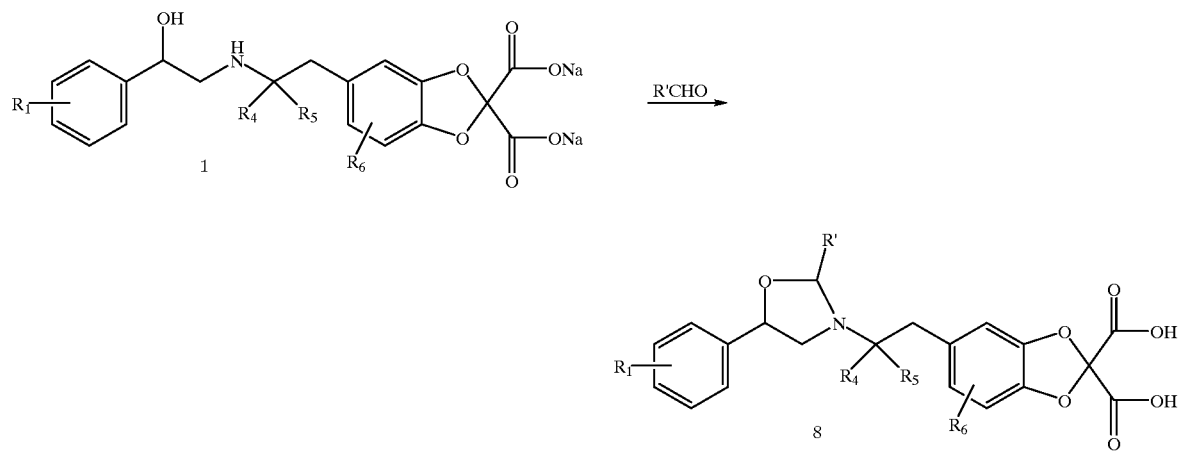

As outlined in Scheme V the diester compounds 5 can be hydrolyzed under basic conditions to a monoester 9a and/or 9b, wherein $R_1$, $R_4$, $R_5$, $R_6$, and $R_9$ are as defined above. One or both of the diastereomers 9a and 9b may be produced in the hydrolysis reaction.

Scheme V

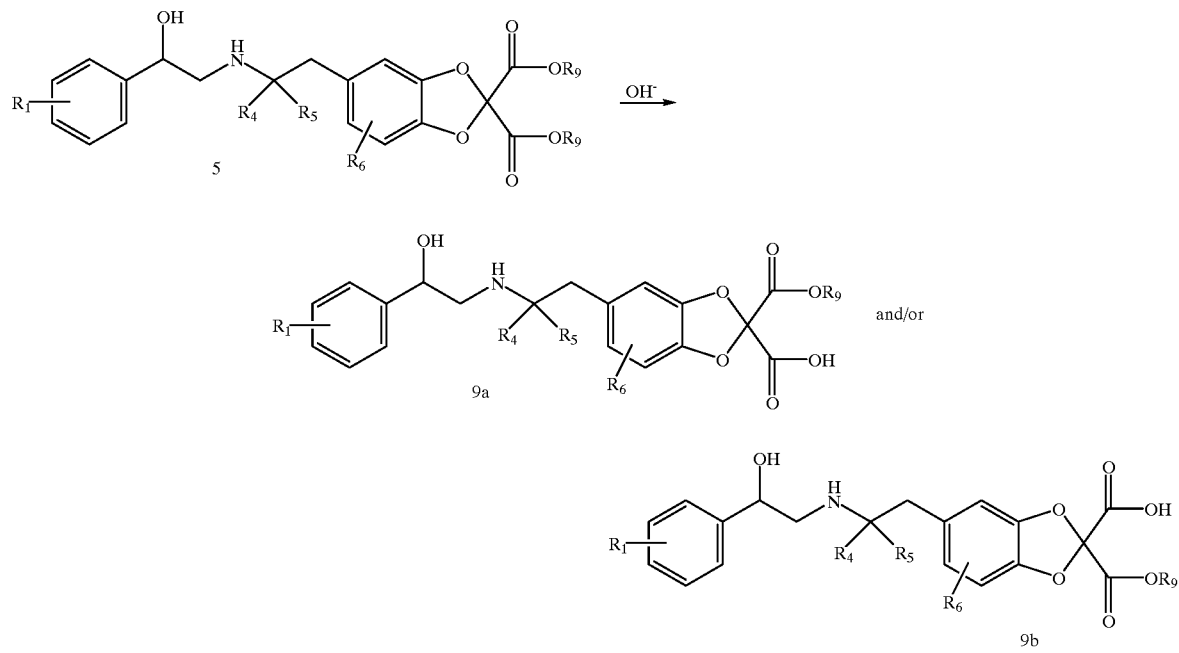

As illustrate in Scheme VI, a diester compound 5 is reacted with an amine $HNR_{11}R_{12}$ to yield the diamide compounds 10, wherein $R_1$, $R_4$, $R_5$, $R_6$, $R_9$, $R_{11}$, and $R_{12}$ are as defined above.

Scheme VI

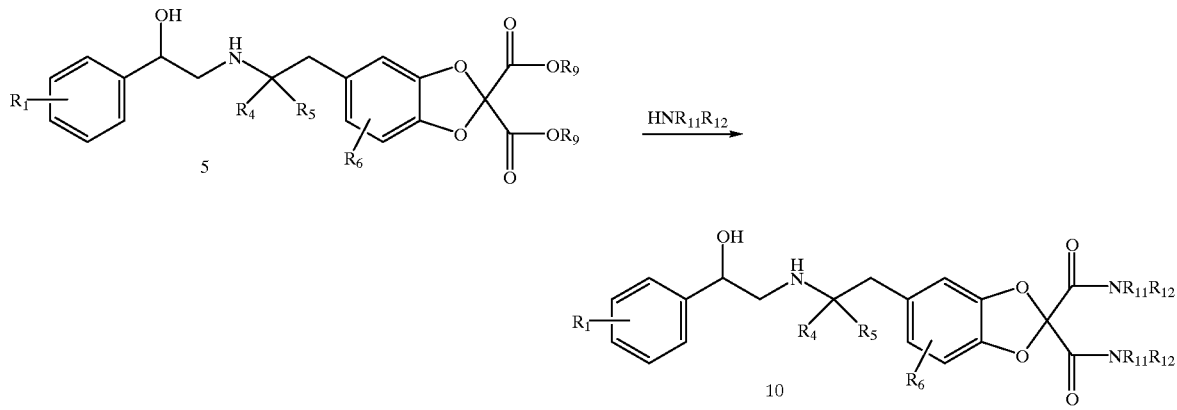

The compounds of this invention were tested for antihyperglycemic and antiobesity activity according to the following procedures.

Human Beta Adrenergic Receptor Selectivity

The activity of the test compounds on human β-adrenergic receptors was determined with Chinese hamster ovary (CHO) cells transfected with human $\beta_2$, or $\beta_1$ adrenergic receptors. Agonist activity is indicated by increased cAMP levels in the CHO cells. Selectivity of the test compounds for the $\beta_3$ receptor was assessed by comparison with results in $\beta_2$ and $\beta_1$ adrenergic receptor transfected cells.

Procedure:
1). Chinese hamster ovary (CHO) cells transfected with human $\beta_2$, or $\beta_1$ adrenergic receptors were used in the assay.
2). Cells were grown to confluent conditions in 24 well plates.
3). Drugs were dissolved in DMSO at a concentration of 10 μM.
4). Cells were incubated with drug at 10 nM concentration for 10 min at 37° C. Isoproterenol (Standard 1) was used as the standard compound and assayed at 10 μM which gives a maximal cAMP elevation in all 3 cell types.
5). Cell cAMP concentrations were assayed using a scintillation proximity assay kit from Amersham Corp., Chicago, Ill.
6). Activities for the test compounds are expressed as a percentage of the isoproterenol response.

Production of the CHO cells transfected with human $\beta_2$, or $\beta_1$ adrenergic receptors, and compound test procedures utilizing the CHO cells, are described by Emorine et al. in their article "Molecular Characterization of the Human Beta$_3$-Adrenergic Receptor", Science 1989, 245(8), 1118–1121 and by Muzzin et al. in the article "An Adipose Tissue-Specific Beta$_3$-Adrenergic Receptor", J. Biol. Chem.1991, 266, 24053–24058.

Effects on Free Fatty Acid Levels in Rats

Rats respond to a single oral dose of $\beta_3$ agonists by increasing plasma free fatty acids (FFA) in response to $\beta_3$ receptor stimulation on the plasma membrane of the fat cell. 5-{2-[2-(3-Chloro-phenyl)-2-hydroxy-ethylamino]-propyl}-benzo[1,3]dioxole-2,2-dicarboxylic acid diisopropyl ester (Standard 2) was used as a standard compound. All test compounds were dosed at 0.1 mg/kg and compared to the response by Standard 2.

Procedure:
1). Drugs were dissolved in DMSO at 10 mg/ml.
2). Twenty μl of the DMSO-drug solution was added to 10 mL methyl cellulose:tween-80 (0.5%:0.1%) for a final concentration of 20 μg/mL.
3). Methyl cellulose:tween-80 drug suspension was given via gavage (1 mL/200 g body weight; or 0.1 mg/kg) to rats and blood was collected 50 min later.
4). Plasma was analyzed for free fatty acids using a kit supplied by Biochemical Diagnostics Inc. (Brentwood, N.Y.).
5). Drug response was calculated from the formula below.

$$\% \, FFA \, Response = \frac{FFA \, (\text{compound}) - FFA \, \text{vehicle}}{FFA \, (\text{Standard 2}) - FFA \, \text{vehicle}} \times 100$$

Effects on Hyperglycemia in Mice

On the morning of Day 1 (baseline), 35 mice (male, db/db (C57BL/KsJ), Jackson Laboratories, 2 to 7 months of age and 35 to 60 g) were fasted for 4 h, weighed, and a baseline blood sample was collected from the tail-tip of each mouse without anesthesia, placed directly into a fluoride-containing tube, mixed, and maintained on ice. Food was then returned to the mice. The plasma was seperated and the levels of glucose in the plasma were dertennined by an Abbot VP Analyzer. Because of the variable plasma glucose levels of the db/db mice, the 5 mice having the most extreme (i.e., highest or lowest) plasma glucose levels were excluded and the remaining 30 mice were randomly assigned into 7 groups of equivalent mean plasma glucose level (vehicle control, ciglitazone (Standard 3), and 5 test compound groups). On the afternoon of Days 1, 2, and 3 the vehicle (0.2 mL of 2% Tween 80/saline w/v) or test compounds were administered (p.o.) to the ad libitum fed mice. On the morning of Day 4, the food was removed from the cages for 3 h, a blood sample was collected, and the mice were then given the fourth administration of test compound or vehicle. Additional blood samples were collected at 2 and 4 h after test compound administration. Plasma glucose levels were determined. To assess test compound activity, the percent change of an animal's plasma glucose level on Day 4 (mean of 2 and 4 h values) from its level before test compound administration (Day 1 baseline sample) was determined as follows:

$$\frac{\text{Mean of 2 and 4 } h \text{ samples (Day 4)}}{\text{Baseline sample (Day 1)}} \times 100$$

A 50–60% reduction of plasma glucose levels in the hyperglycemic db/db mice represents a normalization of glucose levels.

TABLE I

| Compound (Example) | $\beta_1{}^a$ | $\beta_2{}^a$ | Rat Free Fatty Acid$^b$ | db/db Mice Plasma Glucose$^c$ |
|---|---|---|---|---|
| 1 |  | 4% | 65% |  |
| 2 |  | 0.022 μM | 0.071 mg/kg | 0.128 mg/kg |
| 3 |  | 0% | 20% |  |
| 4 |  | 1% | 2% |  |
| 5 |  | 4% | 115% |  |
| 6 |  | 3% | 14% |  |
| 7 |  | 2% | 22% |  |
| 8 |  | 1% | 50% |  |
| 9 |  | 16% | 22% |  |
| 10 |  | 0% | 59% |  |
| 11 |  | nt | 118% |  |
| 12 |  | 1% | 48% |  |
| 14 |  | 5% | 65% |  |
| 15 |  | 18% | 46% |  |
| 16 |  | nt | 0.128 mg/kg |  |
| 17 |  | nt | nt |  |
| 18 |  | 6% | 25% |  |
| 19 |  | 2% | 36% |  |
| 20 |  | 0% | 48% |  |
| 21 |  | 2% | 0.086 mg/kg |  |
| 22 |  | 0.015 μM | 45% |  |
| 23 |  | nt | 57% |  |
| 24 |  | nt | nt |  |
| 25 |  | 6% | 30% |  |
| 26 |  | 7% | 42% |  |
| 27 |  | 5% | 78% |  |
| 28 |  | 2% | 22% |  |
| 29 |  | 2% | 9% |  |
| 30 |  | 0% | 75% |  |
| 31 |  | 5% | 0.090 mg/kg |  |
| 32 |  | 2% | 33% |  |
| 33 | 5.90 μM | 0.100 μM | 0.080 mg/kg | 0.201 mg/kg |
| 34 |  | 2% | 74% |  |
| 35 |  | 4% | 69% |  |
| 36 |  | 2% | 37% |  |
| 37 |  | 3% | 33% |  |
| 38 |  | 0.274 μM | 0.086 mg/kg |  |
| 39 |  | 1% | 71% |  |
| 40 | 8.4 μM | 0.420 μM | 0.071 mg/kg |  |
| 41 |  | 22% | 36% |  |
| 42 |  | 0% | 39% |  |
| 43 |  | 0% | 10% |  |
| 44 |  | 0% | 24% |  |
| 45 |  | 1% | 26% |  |
| 46 |  | 16% | 23% |  |
| 47 |  | 0% | 37% |  |
| 48 |  | 4% | 29% |  |
| 49 |  | 4% | 50% |  |
| 50 |  | 0% | 19% |  |
| 51 |  | 0% | 2% |  |
| 52 |  | 2% | 23% |  |
| 53 |  | 2% | 20% |  |
| 54 |  | 7% | 24% |  |
| 55 |  | 0% | 31% |  |
| 56 |  | 8% | 31% |  |
| 57 |  | 0% | 30% |  |
| 58 |  | 8% | 35% |  |
| 59 |  | 10% | 17% |  |
| 60 |  | 3% | 22% |  |
| 66 |  | 3% | 40% |  |
| 68 |  | 5% | 5% |  |
| 69 |  | 0.079 μM | 42% |  |
| 70 | 3.00 μM | 0.048 μM | 39% |  |
| 71 |  | 14% | 0.076 mg/kg |  |
| 72 |  | 13% | 43% |  |
| 73 |  | 0% | 83% |  |
| 74 |  | 0% | 86% |  |
| 75 | 5.4 μM | 0.058 μM | 0.026 mg/kg | 0.110 mg/kg |
| 76 | 0.980 μM | 0.074 μM | 42% |  |
| 77 |  | 5% | 25% |  |
| 78 | 5.0 μM | 0.325 μM | 0.027 mg/kg | 0.028 mg/kg |
| 79 |  | 0% | 61% |  |
| 80 | 2.4 μM | 0.055 μM | 81% |  |
| 81 | 0.380 μM | 0.059 μM | 61% |  |
| 82 |  | nt | 84% |  |
| 83 |  | nt | 13% |  |
| 84 |  | nt | 65% |  |
| 85 |  | nt | 60% |  |
| 86 |  | nt | 40% |  |
| 87 |  | nt | 68% |  |
| 89 |  | nt | 25% |  |
| 90 |  | 7% | 11% |  |
| 91 |  | 7% | 27% |  |
| 92 |  | nt | 40% |  |
| 93 |  | nt | 75% |  |
| 94 |  | nt | 78% |  |
| 95 |  | 0% | 73% |  |
| 96 |  | 1% | 71% |  |
| 97 |  | 4% | 39% |  |
| 98 |  | 7% | 86% |  |
| 99 |  | 16% | 58% |  |
| 100 |  | 2% | 10% |  |
| 101 |  | 3% | 38% |  |
| 104 |  | 2% | 83% |  |

$^a$Human β receptors expressed in Chinese hamster ovary cells, compounds tested at 10 nM, results expressed as % of isoproterenol activity (increase in cAMP) at 10 μM. $EC_{50}$ (μM) values determined for selected compounds.
$^b$Elevation of plasma free fatty acids in rats, compounds tested at 0.1 mg/kg, results expressed as % of 5-{2-[2-(3-Chloro-phenyl)-2-hydroxy-ethylamino]-propyl}-benzo[1,3]-dioxole-2,2-dicarboxylic acid diisopropyl ester response (78% increase) at 0.1 mg/kg. $ED_{50}$ (mg/kg) values determined for selected compounds.
$^c ED_{50}$ (mg/kg/day) values for lowering of plasma glucose.

The following non-limiting specific examples further illustrate the present invention.

EXAMPLE 1

5-{2-[2-(3-Chloro-phenyl)-2-hydroxy-ethylamino]-propyl}-benzo[1,3]dioxole-2,2-dicarboxylic acid bis-(2-methoxy-ethyl) ester hydrochloride salt To a stirred mixture of 5-{2-[2-(3-chloro-phenyl)-2-hydroxy-ethylamino]-propyl}-benzo[1,3]dioxole-2,2-dicarboxylic acid (1.0 g, 2.37 mmol), and 2-methoxy-1-ethanol (10 mL) was added excess $HCl_{(g)}$. The mixture became homogeneous and was stirred at 23° C. After 12 h, the solution was concentrated, and chromatographed on silica gel, eluting with $CHCl_3$/MeOH (1/0, then 40/1, 20/1 and 10/1) to give fractions containing 5-{2-[2-(3-chloro-phenyl)-2-hydroxy-ethylamino]-propyl}-benzo[1,3] dioxole-2,2-dicarboxylic acid bis-(2-methoxy-ethyl) ester ($R_f$=0.37 (10/1 $CHCl_3$/MeOH)) as a viscous oil. This oil was dissolved in $Et_2O$ (10 mL) and $HCl_{(g)}$ was bubbled through the solution for 1 min. The resulting solution was evaporated to give 1.06 g (78%) of 5-{2-[2-(3-chloro-phenyl)-2-hydroxy-ethylamino]-propyl}-benzo[1,3]dioxole-2,2-dicarboxylic acid bis-(2-methoxy-ethyl) ester hydrochloride salt as a white solid; $^1$H NMR (300 MHz, $CDCl_3$): δ 1.33 (brm, 3H), 2.75–2.88 (brm, 1H), 3.10–3.30 (brm, 2H), 3.35

(s, 6H), 3.40–3.53 (brm 2H), 3.63–3.68 (complexm, 4H), 4.40–4.48 (brm, 4H), 5.40–5.50 (brd, 1H), 5.50–5.75 (brs, 1H), 6.70–6.91 (complex m, 4H), 7.18–7.38 (m, 2H), 7.43 (s, 1H), 8.60–8.85 (brs, 1H), 9.90–10.15 (brs, 1H); MS (ES) m/z (relative intensity): 538 ($M^+$-HCl, 100).

EXAMPLE 2

5-{2-[2-(3-Chloro-phenyl)-2-hydroxy-ethylamino]-propyl}-benzo[1,3]dioxole-2,2-dicarboxylic acid diphenethyl ester hydrochloride salt The title compound was prepared from 5-{2-[2-(3-chloro-phenyl)-2-hydroxy-ethylamino]-propyl}-benzo[1,3]dioxole-2,2-dicarboxylic acid and 2-phenylethanol according to the procedure of Example 1 as a colorless oil; $^1$H NMR (300 MHz, $CDCl_3$): d 1.30–1.45 (brs, 3H), 2.80–2.90 (brm, 1H), 2.89 (t, J=6.9 Hz, 4H), 3.10–3.30 (brm, 2H), 3.39–3.69 (brm, H), 4.40 (t, J=6.8 Hz, 4H), 5.45–5.61 (brs, 2H), 6.70–6.91 (brm, 3H), 7.10–7.35 (complex m, 13H), 7.40–7.51 (brs, 1H), 8.60–8.85 (brs, 1H), 9.91–10.20 (brs, 1H); MS (ES) m/z (relative intensity): 630 ($M^+$-HCl, 40), 144 (100).

EXAMPLE 3

5-{2-[2-(3-Chloro-phenyl)-2-hydroxy-ethylamino]-propyl}-benzo[1,3]dioxole-2,2-dicarboxylic acid bis-(2-butoxy-ethyl) ester hydrochloride salt The title compound was prepared from 5-{2-[2-(3-chloro-phenyl)-2-hydroxy-ethylamino]-propyl}-benzo[1,3]dioxole-2,2-dicarboxylic acid and 2-butoxyethanol according to the procedure of Example 1 as a colorless oil; $^1$H NMR (300 MHz, $CDCl_3$): δ 0.78–0.93 (m, 6H), 1.15–1.78 (m, 12H), 2.70–3.62 (brm, 5H), 3.31–3.47 (m, 4H), 3.57–3.73 (m, 4H), 4.29–4.53 (m, 4H), 5.47–5.57 (brs, 1H), 6.70–6.95 (m, 3H), 7.20–7.49 (m, 4H); MS (ES) m/z (relative intensity): 622 ($M^+$-HCl, 20), 214 (10), 158 (10).

EXAMPLE 4

5-{2-[2-(3-Chloro-phenyl)-2-hydroxy-ethylamino]-propyl}-benzo[1,3]dioxole-2,2-dicarboxylic acid bis-(2-phenoxy-ethyl) ester hydrochloride salt The title compound was prepared from 5-{2-[2-(3-chloro-phenyl)-2-hydroxy-ethylamino]-propyl}-benzo[1,3]dioxole-2,2-dicarboxylic acid and 2-phenoxyethanol according to the procedure of Example 1 as an off-white gummy solid; $^1$H NMR (300 MHz, $CDCl_3$): δ 1.23–1.40 (brs, 3H), 2.70–2.90 (brm, 1H), 3.05–3.30 (brm, 2H), 3.31–3.52 (brm, 2H), 4.12 (t, J=4.4 Hz, 4H), 4.57 (t, J=4.8 Hz, 4H), 5.38–5.60 (brs, 2H), 6.70–7.0 (complexm, 10H), 7.15–7.47 (complex m, 7H), 8.60–8.80 (brs, 1H), 9.90–10.20 (brs, 1H).; MS (ES) m/z (relative intensity): 662 ($M^+$-HCl, (100), 594 (20), 498 (35).

EXAMPLE 5

5-{2-[2-(3-Chloro-phenyl)-2-hydroxy-ethylamino]-propyl}-benzo[1,3]dioxole-2,2-dicarboxylic acid bis-(2-ethoxy-ethyl) ester hydrochloride salt The title compound was prepared from 5-{2-[2-(3-chloro-phenyl)-2-hydroxy-ethylamino]-propyl}-benzo[1,3]dioxole-2,2-dicarboxylic acid and 2-ethoxyethanol according to the procedure of Example 1 as an oily off-white gummy solid; $^1$H NMR (300 MHz, $CDCl_3$): δ 1.10–1.20 (t overlaps with d, J=6.9 Hz, 9H), 1.31–1.41 (brm, 2H), 2.75–2.90 (brm, 1H), 3.10–3.30 (brm, 2H), 3.50 (brq, J=6.9 Hz, 4H), 3.62–3.71 (brm, 4H), 4.37–4.47 (brm, 4H), 5.30–5.70 (brm, 2H), 6.70–6.90 (brm, 4H), 7.19–7.50 (brm, 3H), 8.50–8.85 (brs, 1H), 9.90–10.30 (brs, 1H); MS (ES) m/z (relative intensity): 566 ($M^+$-HCl, (60).

EXAMPLE 6 AND EXAMPLE 7

5-{2-[2-(3-Chloro-phenyl)-2-hydroxy-ethylamino]-propyl}-benzo[1,3]dioxole-2,2-dicarboxylic acid bis-(2-tert-butoxy-ethyl) ester and 5-{2-[2-(3-Chloro-phenyl)-2-hydroxy-ethylamino]-propyl}-benzo[1,3]dioxole-2,2-dicarboxylic acid (2-tert-butoxy-ethyl) ester To a stirred mixture of 5-{2-[2-(3-chloro-phenyl)-2-hydroxy-ethylamino]-propyl}-benzo[1,3]dioxole-2,2-dicarboxylic acid (1.0 g, 2.37 mmol), and 2-t-butoxy-1-ethanol (10 mL) was added p-toluenesulfonic acid (451 mg, 2.37 mmol). The mixture became homogeneous and was stirred at 23° C. After 12 h, an additional portion of p-toluenesulfonic acid (351 mg, 1.84 mmol) was added. After a total of 90 h, the solution was concentrated, and chromatographed on silica gel, eluting with CHCl3/MeOH (1/0, then 40/1, 20/1 and 10/1) to give 100 mg (7%) of 5-{2-[2-(3-chloro-phenyl)-2-hydroxy-ethylamino]-propyl}-benzo[1,3]dioxole-2,2-dicarboxylic acid bis-(2-tert-butoxy-ethyl) ester ($R_f$=0.25 (10/1 $CHCl_3$/MeOH)) as a yellow oil and 320 mg (26%) of 5-{2-[2-(3-chloro-phenyl)-2-hydroxy-ethylamino]-propyl}-benzo[1,3]dioxole-2,2-dicarboxylic acid (2-tert-butoxy-ethyl) ester ($R_f$=0.09 (10/1 $CHCl_3$/MeOH)) as an off-white solid.

5-{2-[2-(3-chloro-phenyl)-2-hydroxy-ethylamino]-propyl}-benzo[1,3]dioxole-2,2-dicarboxylic acid bis-(2-tert-butoxy-ethyl) ester; $^1$H NMR (300 MHz, $CDCl_3$): δ 1.15 (d, 3H), 1.68 (s, 18H), 1.85–2.40 (brm, 2H), 2.50–2.75 (m, 2H), 2.81–2.96 (m, 1H), 3,41–3.51 (m, 4H), 3.56–3.64 (m, 2H), 3.65–3.76 (m, 4H), 4.30–4.41 (m, 2H), 6.61–6.87 (m, 4H), 7.15–7.33 (m, 2H), 7.44 (s, 1H); MS (ES) m/z (relative intensity): 622 ($M^+$, 90), 522 ($M^+$-$t$-$BuOCH_2CH_3$, 60), 352 (40), 266 (100).

5-{2-[2-(3-chloro-phenyl)-2-hydroxy-ethylarnino]-propyl}-benzo[1,3]dioxole-2,2-dicarboxylic acid (2-tert-butoxy-ethyl) ester; $^1$H NMR (300 MHz, $CDCl_3$): δ 1.10 (brm, 12H), 2.25–2.70 (brm, 2H), 3.00–3.30 (brm, 5H), 3.51–3.61 (m, 2H), 4.25–4.47 (m, 2H), 5.20–5.35 (brm, 1H), 6.50–6.70 (brm, 4H), 7.15–7.44 (m, 3H), 8.70–9.70 (brs, 1H). MS (ES) m/z (relative intensity): 522 ($M^+$, 100).

EXAMPLE 8

5-{2-[2-(3-Chloro-phenyl)-2-hydroxy-ethylamino]-propyl}-benzo[1,3]dioxole-2,2-dicarboxylic acid bis-(2-isobutoxy-ethyl) ester The title compound was prepared from 5-{2-[2-(3-chloro-phenyl)-2-hydroxy-ethylamino]-propyl}-benzo[1,3]dioxole-2,2-dicarboxylic acid and 2-isobutoxyethanol according to the procedure of Example 1 as a colorless oil; $^1$H NMR (300 MHz, $CDCl_3$): δ 0.70–0.95 (m, 12H), 1.10–2.0 (complexm, 11H), 3.09–3.29 (m, 4H), 3.51–3.58 (m, 1H), 3.60–3.72 (m, 4H), 4.31–4.48 (m, 2H), 6.70–7.00 (m, 4H), 7.15–7.50 (m, 4H); MS (ES) m/z (relative intensity): 622 ($M^+$-HCl, 100).

EXAMPLE 9

5-{2-[2-(3-Chloro-phenyl)-2-hydroxy-ethylamino]-propyl}-benzo[1,3]dioxole-2,2-dicarboxylic acid bis-(benzyl) ester hydrochloride salt The title compound was prepared from 5-{2-[2-(3-chloro-phenyl)-2-hydroxy-ethylamino]-propyl}-benzo[1,3]

dioxole-2,2-dicarboxylic acid and benzyl alcohol according to the procedure of Example I as a gummy white solid: $^1$H NMR (300 MHz, CDCl$_3$): δ 1.26–1.32 (m, 3H), 2.76 (brt, 1H), 3.01–3.21 (brm, 2H), 3.36–3.49 (brm, 2H), 5.24 (s, 4H), 5.41 (d, J=9.5 Hz, 1H), 6.70–6.88 (m, 3H), 7.12–7.44 (complex m, 14H), 8.70–8.83 (brs, 1H), 9.95–10.10 (brs, 1H); MS (ES) m/z (relative intensity): 602 (M$^+$, 100).

EXAMPLE 10

5-{2-[2-(3-Chloro-phenyl)-2-hydroxy-ethylamino]-propyl}-benzo[1,3]dioxole-2,2-dicarboxylic acid bis-(cyclohexyl) ester hydrochloride salt The title compound was prepared from 5-{2-[2-(3-chloro-phenyl)-2-hydroxy-ethylamino]-propyl}-benzo[1,3]dioxole-2,2-dicarboxylic acid and cyclohexanol according to the procedure of Example 1 as a yellow gum: $^1$H NMR (300 MHz, CDCl$_3$): δ 1.10–1.40 (complex m, 7H), 1.45–1.60 (brm, 4H), 1.63–1.81 (brm, 8H), 1.82–1.95 (brm, 4H), 2.72–2.90 (brm, 1H), 3.10–3.30 (brm, 2H), 3.37–3.55 (m, 2H), 4.90–5.03 (m, 2H), 5.37–5.52 (brs, 1H), 6.71–6.90 (complex m, 4H), 7.20–7.32 (m, 2H), 7.44 (s, 1H), 8.55–8.80 (brs, 1H), 9.90–10.20 (brs, 1H); MS (ES) m/z (relative intensity): 585 (M$^+$-HCl), 532 (10).

EXAMPLE 11

5-{2-[2-(3-Chloro-phenyl)-2-hydroxy-ethylamino]-propyl}-benzo[1,3]dioxole-2,2-dicarboxylic acid bis-(cyclopentyl) ester The title compound was prepared from 5-{2-[2-(3-chloro-phenyl)-2-hydroxy-ethylamino]-propyl}-benzo[1,3]dioxole-2,2-dicarboxylic acid and cyclopentanol as a yellow gum according to the procedure of Example 1, leaving out the final HCl$_{(g)}$/Et$_2$O hydrochloride salt forming step: $^1$H NMR (300 MHz, CDCl$_3$): δ 1.07 (d, J=6.2 Hz, 3H), 1.50–2.00 (complex m, 16H), 2.52–2.70 (complex m, 3H), 2.85–2.95 (m, 2H), 4.55–4.65 (m, 1H), 5.29–5.38 (m, 2H), 6.65–6.72 (m, $^1$H), 6.76 (s, 1H), 6.84 (d, J=8.0 Hz, 1H), 7.18–7.30 (m, 3H), 7.37 (s, 1H); MS (ES) m/z (relative intensity): 558 (M$^+$, 100), 518 (10), 490 (20).

EXAMPLE 12

5-{2-[2-(3-Chloro-phenyl)-2-hydroxy-ethylamino]-propyl}-benzo[1,3]dioxole-2,2-dicarboxylic acid dioctyl ester The title compound was prepared from 5-{2-[2-(3-chloro-phenyl)-2-hydroxy-ethylamino]-propyl}-benzo[1,3]dioxole-2,2-dicarboxylic acid and 1-octanol as a gummy white solid according to the procedure of Example 1, leaving out the final HCl$_{(g)}$/Et$_2$O hydrochloride salt forming step: $^1$H NMR (300 MHz, CDCl$_3$): δ 0.78–0.90 (m, 6H), 0.95–1.40 (brm, 23H), 1.52–1.87 (m, 6H), 2.55–2.75 (brs, 1H), 2.89–3.30 (brm, 4H), 4.12–4.33 (m, 4H), 5.15–5.35 (brs, 1H), 6.60–6.81 (m, 3H), 7.12–7.45 (m, 4H); MS (EI) m/z (relative intensity): 645 (M$^+$, 5), 504 (100), 348 (100), 319 (100), 180 (100).

EXAMPLE 13

5-{2-[2-(3-Chloro-phenyl)-2-hydroxy-ethylamino]-propyl}-benzo[1,3]dioxole-2,2-dicarboxylic acid dipentyl ester The title compound was prepared from 5-{2-[2-(3-chloro-phenyl)-2-hydroxy-ethylamino]-propyl}-benzo[1,3]dioxole-2,2-dicarboxylic acid and 1-pentanol as a brown gum according to the procedure of Example 1, leaving out the final HCl$_{(g)}$/Et$_2$O hydrochloride salt forming step: $^1$H NMR (300 MHz, CDCl$_3$): δ 0.90 (t, J=6.9 Hz, 3H), 1.21–1.41 (brm, 10H), 1.67 (t, J=7.0 Hz, 4H), 1.80–2.10 (brs, 1H), 2.80 (t, J=6.5 Hz, 1H), 3.05–3.19 (brm, 2H), 3.45 (d, J=10.4 Hz, 2H), 4.28 (t, J=6.7 Hz, 4H), 5.46 (d, J=9.6 Hz, 1H), 5.50–5.90 (brs, 1H), 6.71–6.90 (m, 3H), 7.20–7.35 (m, 3H), 7.43 (s, 1H), 8.76 (brs, 1H), 1.05 (brs, 1H); MS (ES) m/z (relative intensity): 562 (M$^+$, 100).

EXAMPLE 14

5-{2-[2-(3-Chloro-phenyl)-2-hydroxy-ethylamino]-propyl}-benzo[1,3]dioxole-2,2-dicarboxylic acid dihexyl ester The title compound was prepared from 5-{2-[2-(3-chloro-phenyl)-2-hydroxy-ethylamino]-propyl}-benzo[1,3]dioxole-2,2-dicarboxylic acid and 1-hexanol as a white solid according to the procedure of Example 1, leaving out the final HCl$_{(g)}$/Et$_2$O hydrochloride salt forming step: $^1$H NMR (300 MHz, CDCl$_3$): δ 0.75–0.90 (m, 6H), 1.00–1.41 (brm, 15H), 1.47–1.85 (m, 6H), 2.60–3.50 (brm, 5H), 4.15–4.30 (m, 4H), 5.18–5.35 (brs, 1H), 6.67–6.82 (m, 3H), 7.15–7.45 (m, 4H); MS (ES) m/z (relative intensity):

EXAMPLE 15

Carbonic acid 3-chloro-benzyl ester 2-(3-chloro-benzyloxycarbonyloxy)-4-{2-[2-(3-chloro-phenyl)-2-hydroxy-ethylamino]-propyl}-phenyl ester The title compound was prepared from 5-{2-[2-(3-chloro-phenyl)-2-hydroxy-ethylamino]-propyl}-benzo[1,3]dioxole-2,2-dicarboxylic acid and 3-chlorobenzyl alcohol as a tan solid according to the procedure of Example 1, leaving out the final HCl$_{(g)}$/Et$_2$O hydrochloride salt forming step: $^1$H NMR (300 MHz, CDCl$_3$): δ 1.28 (d, J=6.3 Hz, 3H), 1.80–2.40 (brs, 1H), 2.79 (t, J=8.8 Hz, 1H), 3.05–3.17 (brm, 2H), 3.37–3.49 (m, 2H), 5.23 (s, 4H), 5.43 (m, 1H), 6.72–6.88 (m, 3H), 7.10–7.44 (complexm, 12H), 8.76 (brs, 1H), 10.02 (brs, 1H); MS (ES) m/z (relative intensity): 670 (M$^+$, 100)

EXAMPLE 16

5-{2-[2-(3-Chloro-phenyl)-2-hydroxy-ethylamino]-propyl}-benzo[1,3]dioxole-2,2-dicarboxylic acid bis-(1-phenyl-ethyl) ester The title compound was prepared from 5-{2-[2-(3-chloro-phenyl)-2-hydroxy-ethylamino]-propyl}-benzo[1,3]dioxole-2,2-dicarboxylic acid and 1-phenylethanol as a gummy tan solid according to the procedure of Example 1, leaving out the final HCl$_{(g)}$/Et$_2$O hydrochloride salt forming step: $^1$H NMR (300 MHz, CDCl$_3$): δ 0.90–1.22 (m, 6H), 1.30–1.61 (m, 6H), 2.39–2.70 (brm, 1H), 2.83–3.19 (brm, 2H), 3.20–3.50 (brm, 2H), 5.15–5.35 (brs, 1H), 5.90–6.02 (brm, 1H), 6.45–6.82 (m, 3H), 7.11–7.40 (m, 4H), 8.64 (brs, 1H), 9.45 (brs, 1H); MS (ES) m/z (relative intensity): 630 (M$^+$, 100).

EXAMPLE 17

5-{2-[2-(3-Chloro-phenyl)-2-hydroxy-ethylamino]-propyl}-benzo[1,3]dioxole-2,2-dicarboxylic acid diheptyl ester The title compound was prepared from 5-{2-[2-(3-chloro-phenyl)-2-hydroxy-ethylamino]-propyl}-benzo[1,3]

dioxole-2,2-dicarboxylic acid and 1-heptanol as a brown gum according to the procedure of Example 1, leaving out the final $HCl_{(g)}/Et_2O$ hydrochloride salt forming step: $^1H$ NMR (300 MHz, $CDCl_3$): δ 0.80–0.92 (m, 6H), 1.23–1.40 (brm, 19H), 1.60–1.75 (m, 4H), 2.80 (t, J=8.8 Hz, 1H), 3.05–3.30 (brm, 2H), 3.38–3.50 (m, 2H), 4.27 (q, J=6.7 Hz, 4H), 5.43 (d, J=8.4 Hz, 1H), 6.72–6.90 (m, 4H), 7.20–7.33 (m, 2H), 7.44 (s, 1H), 8.70 (brs, 1H), 10.10 (brs, 1H); MS (ES) m/z (relative intensity): 618 ($M^+$, 100).

EXAMPLE 18

5-{2-[2-(3-Chloro-phenyl)-2-hydroxy-ethylamino]-propyl}-benzo[1,3]dioxole-2,2-dicarboxylic acid dinonyl ester The title compound was prepared from 5-{2-[2-(3-chloro-phenyl)-2-hydroxy-ethylamino]-propyl}-benzo[1,3]dioxole-2,2-dicarboxylic acid and 1-nonanol as a brown gum according to the procedure of Example 1, leaving out the final $HCl_{(g)}/Et_2O$ hydrochloride salt forming step: $^1H$ NMR (300 MHz, $CDCl_3$): δ 0.88 (t, J=6.8 Hz, 9H), 1.25–1.40 (m, 22H), 1.54–1.60 (m, 2H), 1.63–1.74 (m, 4H), 2.79 (brt, J=8.8 Hz, 1H), 3.08–3.30 (m, 2H), 3.40–3.55 (m, 2H), 4.28 (t, J=6.8 Hz, 4H), 5.46 (d, J=8.7 Hz, 1H), 6.70–6.90 (m, 3H), 7.15–7.35 (m, 3H), 7.43 (s, 1H), 8.72 (brs, 1H), 9.98 (brs, 1H); MS (ES) m/z (relative intensity): 674 ($M^+$, 100), 548 ($M^+$-$C_9H_{20}$, 5).

EXAMPLE 19

5-{2-[2-(3-Chloro-phenyl)-2-hydroxy-ethylamino]-propyl}-benzo[1,3]dioxole-2,2-dicarboxylic acid bis-decyl ester The title compound was prepared from 5-{2-[2-(3-chloro-phenyl)-2-hydroxy-ethylamino]-propyl}-benzo[1,3]dioxole-2,2-dicarboxylic acid and 1-decanol as a brown gum according to the procedure of Example 1, leaving out the final $HCl_{(g)}/Et_2O$ hydrochloride salt forming step: $^1H$ NMR (300 MHz, $CDCl_3$): δ 0.88 (t, J=6.8 Hz, 9H), 1.15–1.40 (m, 24H), 1.52–1.60 (m, 4H), 1.62–1.74 (m, 4H), 2.80 (brt, J=8.8 Hz, 1H), 3.08–3.28 (m, 2H), 3.35–3.52 (m, 2H), 4.28 (t, J=6.7 Hz, 4H), 5.45 (d, J=8.8 Hz, 1H), 6.70–6.90 (m, 3H), 7.18–7.35 (m, 3H), 7.43 (s, 1H), 8.71 (brs, 11H), 10.02 (brs, 1H); MS (ES) m/z (relative intensity): 702 ($M^+$, 100).

EXAMPLE 20

5-{2-[2-(3-Chloro-phenyl)-2-hydroxy-ethylamino]-propyl}-benzo[1,3]dioxole-2,2-dicarboxylic acid didodecyl ester The title compound was prepared from 5-{2-[2-(3-chloro-phenyl)-2-hydroxy-ethylamino]-propyl}-benzo[1,3]dioxole-2,2-dicarboxylic acid and 1-dodecanol as a brown gum according to the procedure of Example 1, leaving out the final $HCl_{(g)}/Et_2O$ hydrochloride salt forming step: $^1H$ NMR (300 MHz, $CDCl_3$): δ 0.88 (t, J=6.8 Hz, 9H), 1.20–1.40 (m, 30H), 1.51–1.60 (m, 4H), 1.62–1.73 (m, 4H), 2.75–2.85 (m, 1H), 3.05–3.25 (m, 2H), 3.35–3.52 (m, 2H), 4.28 (t, J=6.8 Hz, 4H), 5.45 (d, J=8.8 Hz, 1H), 6.60–6.90 (m, 3H), 7.17–7.40 (m, 3H), 7.43 (s, 1H), 8.78 (brs, 1H), 10.05 (brs, 1H); MS (ES) m/z (relative intensity): 594 ($M^+$, 100).

EXAMPLE 21

5-{2-[2-(3-Chloro-phenyl)-2-hydroxy-ethylamino]-propyl}-benzo[1,3]dioxole-2,2-dicarboxylic acid bis-(2-isopropoxy-ethyl) ester The title compound was prepared from 5-{2-[2-(3-chloro-phenyl)-2-hydroxy-ethylamino]-propyl}-benzo[1,3]dioxole-2,2-dicarboxylic acid and 2-isopropoxyethanol as a brown solid according to the procedure of Example 1, leaving out the final $HCl_{(g)}/Et_2O$ hydrochloride salt forming step: $^1H$ NMR (300 MHz, $CDCl_3$): δ 1.11 (d, J=6.1 Hz, 12H), 1.30 (d, J=6.2 Hz, 3H), 2.79 (t, J=8.7 Hz, 1H), 3.06–3.28 (m, 2H), 3.40–3.60 (m, 2H), 3.62–3.70 (complexm, 4H), 3.90–4.12 (brm, 2H), 4.35–4.45 (complexm, 4H), 5.43 (d, J=8.7 Hz, 1H), 6.61–6.90 (m, 3H), 7.11–7.32 (m, 3H), 7.44 (m, 1H), 8.70 (brs, 1H), 9.92 (brs, 1H); MS (ES) m/z (relative intensity): 758 ($M^+$, 30), 546 (100).

EXAMPLE 22

5-{2-[2-(3-Chloro-phenyl)-2-hydroxy-ethylamino]-propyl}-benzo[1,3]dioxole-2,2-dicarboxylic acid isopropyl ester To a stirred solution of 5-{2-[2-(3-chloro-phenyl)-2-hydroxy-ethylamino]-propyl}-benzo[1,3]dioxole-2,2-dicarboxylic acid bis-isopropyl ester hydrochloride salt (3.0 g, 5.53 mmol) and 20 mL of i-PrOH was added was added 1N NaOH (11.1 mL, 11.1 mmol). After stirring at 23° C. for 3 days, the mixture was concentrated to dryness, dissolved in 10% $MeOH/CH_2Cl_2$, and filtered through a small pad of silica gel. The filtrate was concentrated to a colorless gum, and triturated with $Et_2O$ to give 1.0 g (39%) of 5-{2-[2-(3-chloro-phenyl)-2-hydroxy-ethylamino]-propyl}-benzo[1,3]dioxole-2,2-dicarboxylic acid isopropyl ester as a white solid; $^1H$ NMR (300 MHz, $CDCl_3$): δ 0.93 (d, J=6.1 Hz, 3H), 1.17 (d, J=6.3 Hz, 6H), 2.30–2.53 (m, 2H), 2.67–2.80 (m, 2H), 2.85–3.00 (m, 1H), 4.65–4.75 (brs, 1H), 4.91 (hept, J=6.3 Hz, 1H), 6.52–6.80 (complexm, 3H), 7.17–7.45 (complexm, 4H); MS (ES) m/z (relative intensity): 464 ($M^+$, 100).

EXAMPLE 23

5-{2-[2-(3-Chloro-phenyl)-2-hydroxy-ethylamino]-propyl}-benzo[1,3]dioxole-2,2-dicarboxylic acid ethyl ester The title compound was prepared from 5-{2-[2-(3-chloro-phenyl)-2-hydroxy-ethylamino]-propyl}-benzo[1,3]dioxole-2,2-dicarboxylic acid bis-ethyl ester hydrochloride according to the procedure of Example 22 as a brown solid: $^1H$ NMR (300 MHz, $CDCl_3$): δ 1.20 (d, J=6.7 Hz, 3H)1 1.33 (t, J=7.1 Hz, 3H), 2.70 (m, 1H), 2.90–3.22 (m, 4H), 3.23–3.48 (m, 1H), 4.34 (q, J=7.1 Hz, 2H), 5.30 (m, 1H), 6.55–6.90 (m, 3H), 7.10–7.45 (m, 4H); MS (ES) m/z (relative intensity): 450 ($M^+$+1, 50).

EXAMPLE 24

5-{2-[2-(3-Chloro-phenyl)-2-hydroxy-ethylamino]-propyl}-benzo[1,3]dioxole-2,2-dicarboxylic acid bis-methoxycarbonylmethyl ester Step 1

5-(2-{tert-Butoxycarbonyl-[2-(3-chloro-phenyl)-2-hydroxy-ethyl]-amino}-propyl)-benzo[1,3]dioxole-2,2-dicarboxylic acid bis-ethyl ester To a stirred solution of 5-{2-[2-(3-chloro-phenyl)-2-hydroxy-ethylamino]-propyl}-benzo[1,3]dioxole-2,2-dicarboxylic acid diethyl ester hydrochloride salt (5.0 g, 9.72 mmol), and THF (90 mL) was added i-$Pr_2NEt$ (4.23 mL, 3.14 g, 24.3 mmol) and $(Boc)_2O$ (2.12 g, 9.72 mmol).

After 6 h, an additional portion of (Boc)$_2$O (200 mg, 0.92 mmol) is added. After a total of 22 h, the solution was quenched with 10 mL of sat. aq. NaHCO$_3$, and extracted with 3×100 mL Et$_2$O. The combined organics were washed with 1×150 mL of brine, dried over MgSO$_4$, filtered and concentrated to a yellow oil. Flash chromatography on silica gel, eluting with hexanes/EtOAc (2/1) gave 5.07 g (90%) of product as a sticky, off-white solid; $^1$H NMR (300 MHz, CDCl$_3$): δ 1.22 (d, J=6.9 Hz, 3H), 1.30–1.47 (m, 15H), 2.47–2.54(m, 1H), 2.57–2.70 (m, 1H), 3.05–3.15 (m, 1H), 3.46–3.68 (m, 1H), 4.08–4.18 (m, 1H), 4.29–4.42 (m, 4H), 4.75 (brd, J=8.6 Hz, 1H), 5.51 (brs, 1H), 6.55–6.88 (complexm, 4H), 7.20–7.44 (m, 3H); MS (ES) m/z (relative intensity): 578 (M$^+$, 1), 504 (20), 336 (60), 298 (20), 198 (100), 180 (40).

Step 2

5-(2-{tert-Butoxycarbonyl-[2-(3-chloro-phenyl)-2-hydroxy-ethyl]-amino}-propyl)-benzo[1,3]dioxole-2, 2-dicarboxylic acid To a stirred solution of 5-(2-{tert-butoxycarbonyl-[2-(3-chloro-phenyl)-2-hydroxy-ethyl]-amino}-propyl)-benzo[1, 3]dioxole-2,2-dicarboxylic acid bis-ethyl ester (4.42 g, 7.65 mmol), MeOH (100 mL) and H$_2$O (25 mL) was added 5 N NaOH (7.64 mL, 38.2 mmol). After 19 h, the solution was concentrated to an aqueous mixture and acidified to pH=1 with 1 N aq. HCl which turns the solution milky-white. Extraction with 3×100 mL EtOAc, washing the combined organics with 1×200 mL brine, drying over Na$_2$SO$_4$, filtration and concentration gave 3.96 g (99%) of product as a white solid; $^1$H NMR (300 MHz, DMSO-d$_6$): δ 1.16 (d, J=6.7 Hz, 3H), 1.31 (s, 9H), 2.55–2.70 (m, 1H), 2.80–2.92 (m, 1H), 3.05–3.23 (m, 2H), 3.71–3.93 (m, 2H), 4.62–4.87 (m, 2H), 5.30–5.90 (brs, 1H), 6.59–6.99 (complexm, 4H), 7.14–7.47 (complexm, 3H), 8.60–8.80 (brs, 1H); MS (ES) m/z (relative intensity): 522. (M$^+$+H, 50).

Step 3

5-(2-{tert-Butoxycarbonyl-[2-(3-chloro-phenyl)-2-hydroxy-ethyl]-amino}-propyl)-benzo[1,3]dioxole-2, 2-dicarboxylic acid bis-methoxycarbonyl-methyl ester To a stirred solution of 5-(2-{tert-butoxycarbonyl-[2-(3-chloro-phenyl)-2-hydroxy-ethyl]-amino}-propyl)-benzo[1, 3]dioxole-2,2-dicarboxylic acid (500 mg, 0.96 mmol) and DMF (10 mL) was added K$_2$CO$_3$ (132 mg, 0.96 mmol) and methyl-2-bromoacetate (0.23 mL, 366 mg, 2.40 mmol). After stirring at 50° C. for 4 h, the reaction mixture was cooled to 23° C., quenched with 5 mL sat. aq. NaHCO$_3$, and extracted with 3×30 mL of EtOAc. The combined organics were washed with 2×50 mL brine, dried over MgSO$_4$, filtered and concentrated to a yellow oil. Flash chromatography on silica gel, eluting with hexane/EtOAc (4/1 to 2/1), gave 508 mg (79%) of product as a colorless oil; $^1$H NMR (300 MHz, CDCl$_3$): δ 1.22 (d, J=6.9 Hz, 3H), 1.41 (brs, 9H), 2.50–2.60 (brm, 1H), 2.60–2.75 (brm, 1H), 3.06–3.15 (brm, 1H), 3.45–3.60 (brm, 1H), 3.76 (s, 3H), 3.77 (s, 3H), 4.05–4.20 (brm, 1H), 4.70–4.79 (brm, 1H), 4.79(s, 2H), 4.80(s, 2H), 5.42–5.51 (brs, 1H), 6.60–6.91 (complexm, 4H), 7.20–7.43(complexm, 3H); MS (ES) m/z (relative intensity): 666 (M+, (100), 610 (25).

Step 4

5-{2-[2-(3-Chloro-phenyl)-2-hydroxy-ethylamino]-propyl}-benzo[1,3]-dioxole-2,2-dicarboxylic acid bis-methoxycarbonylmethyl ester To a stirred solution of 5-(2-{tert-butoxycarbonyl-[2-(3-chloro-phenyl)-2-hydroxy-ethyl]-amino}-propyl)-benzo[1, 3]dioxole-2,2-dicarboxylic acid bis-methoxycarbonyl-methyl ester (330 mg, 0.50 mmol) and CH$_2$Cl$_2$ (10 mL) was added trifluoroacetic acid (0.08 mL, 113 mg, 0.99 mmol). After stirring at 23° C. for 1 h, additional trifluoroacetic acid (0.08 mL, 113 mg, 0.99 mmol) was added. After a total of 22 h, the mixture was quenched with 5 mL of sat. aq. NaHCO$_3$, and extracted with 3×30 mL of EtOAc. The combined organics were washed with 1×50 mL of brine, dried over MgSO$_4$, filtered and concentrated to a yellow oil. Flash chromatography on silica gel, eluting with CHCl$_3$/MeOH (20/1 to 10/1) gave 145 mg (52%) of product as a white gum; $^1$H NMR (300 MHz, CDCl$_3$): δ 1.33 (m, 3H), 1.70–2.40 (brm, 2H), 2.73–2.90 (brt, 1H), 3.04–3.30 (m, 2H), 3.37–3.53 (m, 2H), 3.75 (s, 3H), 3.76 (s, 3H), 4.80 (s, 2H), 4.81 (s, 2H), 5.40 (m, 1H), 6.73–6.93 (complexm, 4H), 7.15–7.32 (m, 2HO, 7.43 (s, 1H); MS (ES) m/z (relative intensity): 566 (M$^+$, 80), 508 (M$^+$-CO$_2$CH$_3$+H, 100), 450 (M$^+$-2CO$_2$CH$_3$+2H, 30).

EXAMPLE 25

5-{2-[2-(3-Chloro-phenyl)-2-hydroxy-ethylamino]-propyl}-benzo[1,3]dioxole-2,2-dicarboxylic acid bis-propoxycarbonylmethyl ester Step 1

5-(2-{tert-Butoxycarbonyl-[2-(3-chloro-phenyl)-2-hydroxy-ethyl]-amino}-propyl)-benzo[1,3]dioxole-2, 2-dicarboxylic acid bis-propoxycarbonylmethyl ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid and propyl 2-bromoacetate according to the procedure of Example 24, step 3 as a colorless oil: $^1$H NMR (300 MHz, CDCl$_3$): δ 0.91 (t, J=7.4 Hz, 6H), 1.21 (d, J=6.9 Hz, 3H), 1.40 (s, 9H), 1.55–1.72 (m, 4H), 2.47–2.70 (m, 1H), 3.05–3.17 (m, 1H), 3.46–3.60 (m, 1H), 4.11 (t, J=6.6 Hz, 4H), 4.70–4.85 (m, 4H), 5.47 (s, 1H), 6.60–6.92 (m, 3H), 7.20–7.35 (m, 3H), 7.41 (s, 1H); MS (ES) m/z (relative intensity): 722 (M$^+$, 100).

Step 2

5-{2-[2-(3-Chloro-phenyl)-2-hydroxy-ethylamino]-propyl}-benzo[1,3]-dioxole-2,2-dicarboxylic acid bis-propoxycarbonylmethyl ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid bis-propoxyoxycarbonylmethyl ester according to the procedure of Example 24, step 4 as a brown gum: $^1$H NMR (300 MHz, CDCl$_3$): δ 0.80–0.95 (m, 9H),1.40–1.80 brm, 6H), 2.80–3.74 (brm, 7H), 4.05–4.20 (m, 4H), 4.70–4.85 (m, 2H), 5.10 (brs, 1H), 6.70–6.95 (brm, 3H), 7.15–7.40 (brm, 4H); MS (ES) m/z (relative intensity): 622 (M$^+$, 100).

EXAMPLE 26

5-{2-[2-(3-Chloro-phenyl)-2-hydroxy-ethylamino]-propyl}-benzo[1,3]dioxole-2,2-dicarboxylic acid bis-(1-methoxycarbonyl-ethyl) ester Step 1

5-(2-{tert-Butoxycarbonyl-[2-(3-chloro-phenyl)-2-hydroxy-ethyl]-amino}-propyl)-benzo[1,3]dioxole-2, 2-dicarboxylic acid bis-(1-methoxycarbonyl-ethyl) ester The title compound was prepared from 5-(2-{tert-butoxycarbonyl-[2-(3-chloro-phenyl)-2-hydroxy-ethyl]- amino}-propyl)-benzo[1,3]dioxole-2,2-dicarboxylic acid and methyl 1-bromopropionate according to the procedure of Example 24, step 3 as a colorless oil : $^1$H NMR (300 MHz, CDCl$_3$): δ 1.22 (d, J=6.9 Hz, 3H), 1.38 (s, 9H), 2.50–2.70 (m, 2H), 2.89 (s, 3H), 2.96 (s, 3H), 3.07–3.15 (m, 1H), 3.45–3.60 (m, 1H), 3.70–3.83 (m, 8H), 4.05–4.18 (m, 1H), 4.72–4.80 (m, 1H), 5.22–5.32 (m, 1H), 6.60–6.90 (m, 3H), 7.20–7.32 (m, 3H), 7.41 (s, 1H); MS (ES) m/z (relative intensity): 694 (M$^+$, 100), 638 (M$^+$-t-Bu, 20), 594 (M$^+$-Boc, 20).

Step 2

5-{2-[2-(3-Chloro-phenyl)-2-hydroxy-ethylamino]-propyl}-benzo[1,3]dioxole-2,2-dicarboxylic acid bis-(1-methoxycarbonyl-ethyl)ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid bis-methoxycarbonyl-1-ethyl ester according to the procedure of Example 24, step 4 as a colorless gum: $^1$H NMR (300 MHz, CDCl$_3$): δ 1.28 (d, J=6.7 Hz, 3H), 1.30–2.00 (brm, 2H), 1.55–1.65 (m, 6H), 2.70–2.80 (m, 1H), 3.05–3.30 (m, 2H), 3.35–3.69 (m, 2H), 3.68–3.80 (m, 6H), 5.10–5.18 (m, 1H), 5.22–5.31 (m, 2H), 6.70–6.95 (m, 3H), 7.15–7.30 (m, 3H), 7.36 (s, 1H); MS (ES) m/z (relative intensity): 594 (M$^+$, 100).

EXAMPLE 27

5-{2-[2-(3-Chloro-phenyl)-2-hydroxy-ethylamino]-propyl}-benzo[1,3]dioxole-2,2-dicarboxylic acid bis-isopropoxycarbonylmethyl ester Step 1

5-(2-{tert-Butoxycarbonyl-[2-(3-chloro-phenyl)-2-hydroxy-ethyl]-amino}-propyl)-benzo[1,3]dioxole-2,2-dicarboxylic acid bis-isopropoxycarbonyl-methyl ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid and isopropyl 2-bromoacetate according to the procedure of Example 24, step 3 as a colorless oil: $^1$H NMR (300 MHz, CDCl$_3$): δ 1.15–1.30 (m, 15H), 1.40 (s, 9H), 2.45–2.70 (m, 2H), 3.06–3.15 (m, 1H), 3.45–3.60 (m, 1H), 4.05–4.18 (m, 2H), 4.70–4.80 (m, 4H), 5.06 (sept, J=6.3 Hz, 2H), 5.46 (brs, 1H), 6.60–6.90 (m, 3H), 7.20–7.35 (m, 3H), 7.41 (s, 1H).; MS (ES) m/z (relative intensity): 722 (M$^+$, 100).

Step 2

5-{2-[2-(3-Chloro-phenyl)-2-hydroxy-ethylamino]-propyl}-benzo [1,3]dioxole-2,2-dicarboxylic acid bis-isopropoxycarbonylmethyl ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid bis-isopropoxycarbonylmethyl ester according to the procedure of Example 24, step 3 as a brown gum: $^1$H NMR (300 MHz, CDCl$_3$): δ 1.17–1.30 (m, 15H), 2.72–2.82 9m, 1H), 3.10–3.29 (m, 3H), 3.38–3.50 (m, 1H), 4.70–4.80 (m, 4H), 4.95–5.18 (complexm, 3H), 6.72–6.95 (m, 3H), 7.15–7.30 (m, 3H), 7.36 (s, 1H), 8.73 (brs, 1H), 9.86 (brs, 1H); MS (ES) m/z (relative intensity): 622 (M$^+$, 100).

EXAMPLE 28

5-{2-[2-(3-Chloro-phenyl)-2-hydroxy-ethylamino]-propyl}-benzo[1,3]dioxole-2,2-dicarboxylic acid bis-ethoxycarbonylmethyl ester Step 1

5-(2-{tert-Butoxycarbonyl-[2-(3-chloro-phenyl)-2-hydroxy-ethyl]-amino}-propyl)-benzo[1,3]dioxole-2, 2-dicarboxylic acid bis-ethoxycarbonyl methylester The title compound was prepared from 5-(2-(tert-butoxycarbonyl-[2-(3-chloro-phenyl)-2-hydroxy-ethyl]-amino}-propyl)-benzo[1,3]dioxole-2,2-dicarboxylic acid and ethyl bromoacetate according to the procedure of Example 24, Step 3 as a colorless oil; $^1$H NMR (300 MHz, CDCl$_3$): δ 1.17–1.30 (m, 9H), 1.39 (s, 9H), 2.48–2.54 (brm, 1H), 2.55–2.61(brm, 1H), 3.07–3.13 (m, 2H), 3.47–3.55 (brm, 1H), 4.05–4.20 (brm, 1H), 4.21 (q, J=7.0 Hz, 4H), 4.20–4.33 (brm, 1H), 4.78 (s, 2H), 4.79 (s, 2H), 5.45–5.50 (brm, 1H), 6.61–6.85 (m, 4H), 7.20–7.43 (m, 3H); MS (ES) m/z (relative intensity): 694 (M$^+$, (100), 638 (15), 594 (15).

Step 2

5-{2-[2-(3-Chloro-phenyl)-2-hydroxy-ethylamino]-propyl}-benzo[1,3]dioxole-2,2-dicarboxylic acid bis-ethoxycarbonylmethyl ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid bis-ethoxycarbonylmethyl ester according to the procedure of Example 24, Step 4 as a white gum; $^1$H NMR (300 MHz, CDCl$_3$): δ 1.15–1.27 (m, 3H), 1.31–1.41 (t, J=6.8 Hz, 6H), 2.53–3.51 (m, 6H), 3.60–3.80 (m, 4H), 4.00–4.10 (brs, 1H), 4.15–4.30 (q, J=6.7 Hz, 4H), 4.70–4.85 (brm, 1H), 6.60–6.95 (m, 3H), 7.10–7.50 (m, 4H); MS (ES) m/z (relative intensity): 594 (M$^+$, 10), 522 (80), 508 (80), 436 (100).

EXAMPLE 29

5-{2-[2-(3-Chloro-phenyl)-2-hydroxy-ethylamino]-propyl}-benzo[1,3]dioxole-2,2-dicarboxylic acid bis-(1-ethoxycarbonyl-ethyl) ester Step 1

5-(2-{tert-Butoxycarbonyl-[2-(3-chloro-phenyl)-2-hydroxy-ethyl]-amino}-propyl)-benzo[1,3]dioxole-2, 2-dicarboxylic acid bis-(1-ethoxycarbonyl-ethyl) ester The title compound was prepared from 5-(2-{tert-butoxycarbonyl-[2-(3-chloro-phenyl)-2-hydroxy-ethyl]-amino}-propyl)-benzo[1,3]dioxole-2,2-dicarboxylic acid and ethyl 2-bromopropionate according to the procedure of Example 24, Step 3 as a colorless oil; $^1$H NMR (300 MHz, CDCl$_3$): δ 1.15–1.30 (complex m, 9H), 1.40 (brs, 9H), 1.52–1.69 (m, 6H), 2.47–2.58 (m, 1H), 2.58–2.70 (m, 1H), 3.05–3.16 (m, 1H), 3.42–3.54 (m, 1H), 4.05–4.30 (complexm, 5H), 4.77 (m, 1H), 5.19–5.30 (m, 2H), 5.49 (brs, 1H), 6.57–6.67 (m, 1H), 6.71–6.80 (m, 1H), 6.82–6.91 (m, 2H), 7.20–7.35 (m, 2H), 7.41 (brs, 1H); MS (ES) m/z (relative intensity): 722 (M$^+$, 100).

Step 2

5-{2-[2-(3-Chloro-phenyl)-2-hydroxy-ethylamino]-propyl}-benzo[1,3]dioxole-2,2-dicarboxylic acid bis-(1-ethoxycarbonyl-ethyl) ester The title compound was prepared from 5-(2-{tert-butoxycarbonyl-[2-(3-chloro-phenyl)-2-hydroxy-ethyl]- amino}-propyl)-benzo[1,3]dioxole-2,2-dicarboxylic acid bis-ethoxycarbonyl-1-ethyl ester according to the procedure of Example 24, Step 4 as a colorless oil; $^1$H NMR (300 MHz, CDCl$_3$): δ very complex due to 4 diastereomers present; MS (ES) m/z (relative intensity): 622 (M$^+$, 40), 522 (M$^+$-CH$_3$CHCO$_2$Et, 100).

EXAMPLE 30

5-{2-[2-(3-Chloro-phenyl)-2-hydroxy-ethylamino]-propyl}-benzo[1,3]dioxole-2,2-dicarboxylic acid bis-trimethylsilanylmethyl ester Acetyl chloride (0.59 g, 7.5 mmol) was added to trimethylsilylmethanol (4.03 g, 37.5 mmol) with stirring at room temperature. After 0.5 h, 5-{2-[2-(3-chloro-phenyl)-2-hydroxy-ethylamino]-propyl}-benzo[1,3]dioxole-2,2-dicarboxylic acid (1.05 g, 2.5 mmol) was added in portions. The resulting solution was stirred for 3 days, and then treated with 50 ml of 50% sodium bicarbonate solution, followed by extraction with ethyl acetate (50 ml). The organic extract was dried over anhydrous sodium sulfate, filtered, and evaporated. The residue was passed through a pad of silica gel, eluting with hexanes, and ether-hexanes/1:1 until no more trimethylsilylmethanol could be detected. The filter pad was then eluted with ethyl acetate, and the solvent was evaporated to give 1.14 g of the desired product as a colorless gum. Conversion to the HCl salt yielded 1.16 g of white foam; $^1$H NMR (CDCl$_3$) δ 0.06 (s, 18H), 1.33 (d, J=6.5 Hz, 3H), 2.80 (m, 1H), 3.15 (m, 1H), 3.20 (m, 1H), 3.48 (m, 2H), 4.014 (s, 2H), 4.015 (s, 2H), 5.45 (bd, J=9.7 Hz, 1H), 5.60 (bs, 1H), 6.80 (m, 3H), 7.25 (m, 2H), 7.45 (s, 1H), 8.70 (bs, 1H), 10.10 (bs, 1H); IR (KBr): 1763 cm$^{-1}$ (C=O); MS (ES) m/z 594 (MH$^+$); [α]$_D^{25}$ -23° (c, 1.0, CHCl$_3$). Anal. Calcd. for C$_{28}$H$_{40}$ClNO$_7$Si$_2$·HCl: C, 53.32; H, 6.39; N, 2.22; Cl, 11.24; Si, 8.91. Found: C, 52.65; H, 6.70; N, 2.11; Cl, 11.47; Si, 9.00.

EXAMPLE 31

5-{2-[2-(3-Chloro-phenyl)-2-hydroxy-ethylamino]-propyl}-benzo[1,3]dioxole-2,2-dicarboxylic acid bis-(2-trimethylsilanyl-ethyl) ester The title compound was prepared from 5-{2-[2-(3-chloro-phenyl)-2-hydroxy-ethylamino]-propyl}-benzo[1,3]dioxole-2,2-dicarboxylic acid and 2-trimethylsilylethanol according to the procedure of Example 30 as a white foam (HCl salt); $^1$H NMR (CDCl$_3$) δ 0.03 (s, 18H), 1.06 (t, J=8.6 Hz, 4H), 1.33 (bs, 3H), 1.90 (bs, 1H), 2.80 (bs, 1H), 3.18 (bs, 2H), 3.48 (bs, 2H), 4.37 (t, J=8.6 Hz, 4 H), 5.45 (bs, 1H), 6.80 (m, 3H), 7.26 (m, 2H), 7.43 (s, 1H), 8.70 (bs, 1H), 10.10 (bs, 1H); IR (KBr): 1763 cm$^{-1}$ (C=O); MS (ES) m/z 622 (MH$^+$); [α]$_D^{25}$ -23° (c, 1.0, CHCl$_3$). Anal. Calcd. for C$_{30}$H$_{44}$ClNO$_7$Si$_2$·HCl: C, 54.70; H, 6.88; N, 2.13; Cl, 10.76; Si, 8.53. Found: C, 53.96; H, 7.05; N, 1.86; Cl, 8.84; Si, 10.33.

EXAMPLE 32

5-{2-[2-(3-Chloro-phenyl)-2-hydroxy-ethylamino]-propyl}-benzo[1,3]dioxole-2,2-dicarboxylic acid bis-(3-trimethylsilanyl-propyl) ester The title compound was prepared from 5-{2-[2-(3-chloro-phenyl)-2-hydroxy-ethylamino]-propyl}-benzo[1,3]dioxole-2,2-dicarboxylic acid and 3-trimethylsilylpropanol according to the procedure of Example 24 as a white foam (HCl salt); $^1$H NMR (CDCl$_3$) δ 0.01 (s, 18H), 0.46 (m, 4H), 1.33 (d, J=6.3 Hz, 3H), 1.70 (m, 4H), 2.80 (m, 1H), 3.18 (m, 2H), 3.46(m 2H), 4.24(t, J=7.0 Hz, 4H), 5.47 (bd, J=9.7 Hz, I H), 5.70 (bs, 1H), 6.80 (m, 3H), 7.25 (m, 2H), 7.43 (s, 1H), 8.70 (bs, 1H), 10.10 (bs, 1H); IR (KBr): 1765 cm$^{-1}$ (C=O); MS (ES) m/z 650 (MH$^+$); [α]$_D^{25}$ -22° (c, 1.0, CHCl$_3$). Anal. Calcd. for C$_{32}$H$_{48}$ClNO$_7$Si$_2$·HCl: C, 55.96; H, 7.04; N, 2.04 Cl, 10.32; Si, 8.18. Found: C, 55.82; H, 7.21; N, 1.87; Cl, 10.22; Si, 7.76.

EXAMPLE 33

5-{2-[2-(3-Chloro-phenyl)-2-hydroxy-ethylamino]-propyl}-benzo[1,3]dioxole-2,2-dicarboxylic acid bis-(3,3-dimethyl-butyl) ester The title compound was prepared from 5-{2-[2-(3-chloro-phenyl)-2-hydroxy-ethylarnino]-propyl}-benzo[1,3]dioxole-2,2-dicarboxylic acid and 3,3-dimethylbutanol according to the procedure of Example 30 as a white foam (HCl salt); $^1$H NMR (CDCl$_3$) δ 0.90 (s, 18H), 1.33 (bs, 3H), 1.62 (t, J=7.4 Hz, 4H), 2.80 (bs, 1H), 3.18 (bs, 2H), 3.48 (bs, 2H), 4.35 (t, J=7.4 Hz, 4H), 5.45 (bs, 1H), 6.80 (m, 3 H), 7.26 (m, 2H), 7.43 (s, 1H), 8.70 (bs, 1H), 10.10 (bs, 1H); IR (KBr): 1765 cm$^{-1}$ (C=O); MS (CI) m/z 590 (MH$^+$); [α]$_D^5$ -24° (c, 1.0, CHCl$_3$). Anal. Calcd. for C$_{32}$H$_{44}$ClNO$_7$·HCl: C, 61.34; H, 7.08; N, 2.24; Cl, 11.32. Found: C, 60.79; H, 7.46; N, 2.09; Cl, 11.95.

EXAMPLE 34

5-{2-[2-(3-Chloro-phenyl)-2-hydroxy-ethylamino]-propyl}-benzo[1,3]dioxole-2,2-dicarboxylic acid bis-cyclohexylmethyl ester The title compound was prepared from 5-{2-[2-(3-chloro-phenyl)-2-hydroxy-ethylamino]-propyl}-benzo[1,3]dioxole-2,2-dicarboxylic acid and cyclohexylmethanol according to the procedure of Example 30 as a white foam (HCl salt); $^1$H NMR (CDCl$_3$) δ 0.80–1.80 (m, 22H), 1.33 (bs, 3H), 2.80 (m, 1H), 3.18 (m, 2H), 3.48 (m, 2H), 4.10 (m, 4H), 5.50 (bs, 1H), 6.80 (m, 3H), 7.25 (m, 2H), 7.43 (s, 1H), 8.70 (bs, 1H), 10.10 (bs, 1H); IR (KBr): 1765 cm$^{-1}$ (C=O); MS (CI) m/z 614 (MH$^+$); [α]$_D^{25}$ -22° (c, 1.0, CHCl$_3$). Anal. Calcd. for C$_{34}$H$_{44}$ClNO$_7$·HCl: C, 62.77; H, 6.82; N, 2.15; Cl, 10.90. Found: C, 61.83; H, 7.27; N, 2.07; Cl, 10.25.

EXAMPLE 35

5-{2-[2-(3-Chloro-phenyl)-2-hydroxy-ethylamino]-propyl}-benzo[1,3]dioxole-2,2-dicarboxylic acid bis-(4-methyl-pentyl) ester The title compound was prepared from 5-{2-[2-(3-chloro-phenyl)-2-hydroxy-ethylamino]-propyl}-benzo[1,3]dioxole-2,2-dicarboxylic acid and 4-methylpentanol according to the procedure of Example 30 as a colorless gum (HCl salt); $^1$H NMR (CDCl$_3$) δ 0.87 (d, J=6.5 Hz, 12H), 1.33 (bs, 3H), 1.10–2.0 (m, 10H), 2.80 (bs, 1H), 3.18 (bs, 2H), 3.48 (bs, 2H), 4.28(m, 4H), 5.60 (bs, 2H), 6.80 (m, 3H), 7.25 (m, 2H), 7.43 (s, 1H), 8.70 (bs, 1H), 10.10 (bs, 1H); IR (KBr): 1765 cm$^{-1}$ (C=O); MS (CI) m/z 590 (MH$^+$); [α]$_D^{25}$ -24° (c, 1.0, CHCl$_3$). Anal. Calcd. for C$_{32}$H$_{44}$ClNO$_7$·HCl: C, 61.34; H, 7.08; N, 2.24; Cl, 11.32. Found: C, 60.50; H, 7.36; N, 2.13; Cl, 11.66.

EXAMPLE 36

5-{2-[2-(3-Chloro-phenyl)-2-hydroxy-ethylamino]-propyl}-benzo[1,3]dioxole-2,2-dicarboxylic acid bis-(2-cyclohexyl-ethyl ) ester The title compound was prepared from 5-{2-[2-(3-chloro-phenyl)-2-hydroxy-ethylamino]-propyl}-benzo[1,3]

dioxole-2,2-dicarboxylic acid and 2-cyclohexylethanol according to the procedure of Example 30 as an off-white foam (HCl salt); $^1$H NMR (CDCl$_3$) δ 0.80–1.80 (m, 26H), 1.32 (d, J=6.3 Hz, 3H), 2.80 (m, 1H), 3.18 (m, 2H), 3.48 (m, 2H), 4.32 (t, J=6.9 Hz, 4H), 5.45 (bd, J=9.7 Hz, 1H), 6.80 (m, 3 H), 7.25 (m, 2H), 7.45 (s, 1H), 8.70 (bs, 1H), 10.0 (bs, 1H); IR (KBr): 1765 cm$^{-1}$ (C=O); MS (CI) m/z 642 (MH$^+$); $[α]_D^{25}$ −24° (c, 1.0, CHCl$_3$). Anal. Calcd. for C$_{36}$H$_{48}$ClNO$_7$·HCl: C, 63.71; H, 7.13; N, 2.06; Cl, 10.45. Found: C, 63.07; H, 7.54; N, 2.07; Cl, 12.81.

EXAMPLE 37

5-{2-[2-(3-Chloro-phenyl)-2-hydroxy-ethylamino]-propyl}-benzo[1,3]dioxole-2,2-dicarboxylic acid bis-(3-cyclopentyl-propyl) ester The title compound was prepared from 5-{2-[2-(3-chloro-phenyl)-2-hydroxy-ethylamino]-propyl}-benzo[1,3]dioxole-2,2-dicarboxylic acid and 3-cyclopentylpropanol according to the procedure of Example 30 as a colorless gum (HCl salt); $^1$H NMR (CDCl$_3$) δ 0.80–1.80 (m, 26H), 1.33 (d, J=6.3 Hz, 3H), 2.80 (m, 1H), 3.18 (m, 2H), 3.48 (m, 2H), 4.28 (t, J=6.8 Hz, 4H), 5.45 (bd, J=9.7 Hz, 1H), 6.80 (m, 3H), 7.25 (m, 2H), 7.45 (s, 1H), 8.70 (bs, 1H), 10.10 (bs, 1 H); IR (KBr): 1765 cm$^{-1}$ (C=O); MS (CI) m/z 642 (MH$^+$); $[α]_D^{25}$ −21° (c, 1.0, CHCl$_3$). Anal. Calcd. for C$_{36}$H$_{48}$ClNO$_7$·HCl: C, 63.71; H, 7.13; N, 2.06; Cl, 10.45. Found: C, 63.69; H, 7.64; N, 2.00; Cl, 10.13.

EXAMPLE 38

5-{2-[2-(3-Chloro-phenyl)-2-hydroxy-ethylamino]-propyl}-benzo[1,3]dioxole-2,2-dicarboxylic acid bis-cyclopropylmethyl ester The title compound was prepared from 5-{2-[2-(3-chloro-phenyl)-2-hydroxy-ethylamino]-propyl}-benzo[1,3]dioxole-2,2-dicarboxylic acid and cyclopropylmethanol according to the procedure of Example 30 as a white solid (HCl salt); $^1$H NMR (CDCl$_3$) δ 0.33 (m, 4H), 0.61 (m, 4H), 1.21, (m, 2H), 1.32 (bs, 3H), 2.80 (m, 1H), 3.19 (m, 2H), 3.48 (m, 2H), 4.15 (d, J=7.3 Hz, 4H), 5.50 (bd, 1H), 5.70 (bs, 1H), 6.80 (m, 3H), 7.25 (m, 2H), 7.45 (s, 1H), 8.70 (bs, 1H), 10.10 (bs, 1 H); IR (KBr): 1757, 1778 cm$^{-1}$ (C=O); MS (ES) m/z 530 (MH$^+$); $[α]_D^{25}$ −26° (c, 1.0, CHCl$_3$). Anal. Calcd. for C$_{28}$H$_{32}$ClNO$_7$·HCl: C, 59.37; H, 5.69; N, 2.47; Cl, 12.53. Found: C, 59.19; H, 5.88; N, 2.29; Cl, 12.87.

EXAMPLE 39

5-{2-[2-(3-Chloro-phenyl)-2-hydroxy-ethylamino]-propyl}-benzo[1,3]dioxole-2,2-dicarboxylic acid bis-(1-methyl-cyclopropylmethyl) ester The title compound was prepared from 5-{2-[2-(3-chloro-phenyl)-2-hydroxy-ethylamino]-propyl}-benzo[1,3]dioxole-2,2-dicarboxylic acid and 1-methylcyclopropyl-methanol according to the procedure of Example 30 as a white solid (HCl salt); $^1$H NMR (CDCl$_3$) δ 0.39 (m, 4H), 0.52 (m, 4H), 1.10, (s, 6H), 1.32 (d, J=6.5 Hz, 3H), 2.80 (m, 1H), 3.19 (m, 2H), 3.48 (m, 2H), 4.10 (s, 4H), 5.50 (bd, 1H), 5.70 (bs, 1H), 6.80 (m, 3H), 7.25 (m, 2H), 7.45 (s, 1H), 8.70 (bs, 1H), 10.10 (bs, 1H); IR (KBr): 1763 cm$^{-1}$ (C=O); MS (ES) m/z 558 (MH$^+$); $[α]_D^{25}$ −25° (c, 1.0, CHCl$_3$). Anal. Calcd. for C$_{30}$H$_{36}$ClNO$_7$·HCl: C, 60.61; H, 6.10; N, 2.36; Cl, 11.94. Found: C, 60.02; H, 6.58; N, 2.17; Cl, 11.20.

EXAMPLE 40

5-{2-[2-(3-Chloro-phenyl)-2-hydroxy-ethylamino]-propyl}-benzo[1,3]dioxole-2,2-dicarboxylic acid bis-cyclobutylmethyl ester The title compound was prepared from 5-{2-[2-(3-chloro-phenyl)-2-hydroxy-ethylamino]-propyl}-benzo[1,3]dioxole-2,2-dicarboxylic acid and cyclobutylmethanol according to the procedure of Example 30 as an off-white solid (HCl salt); $^1$H NMR (CDCl$_3$) δ 1.32 (d, J=6.5 Hz, 3H), 1.85 (m, 8H), 2.05 (m, 4H), 2.69 (m, 2H), 2.80 (m, 1H), 3.19 (m, 2H), 3.48 (m, 2H), 4.10 (s, 4H), 5.50 (bd, 1H), 5.70 (bs, 1H), 6.80 (m, 3H), 7.25 (m, 2H), 7.45 (s, 1H), 8.70 (bs, 1H), 10.10 (bs, 1H); IR (KBr): 1759, 1779 cm$^{-1}$ (C=O); MS (ES) m/z 558 (MH$^+$); $[α]_D^{25}$ −27° (c, 1.0, CHCl$_3$). Anal. Calcd. for C$_{30}$H$_{36}$ClNO$_7$·HCl: C, 60.61; H, 6.10; N, 2.36; Cl, 11.94. Found: C, 60.68; H, 6.30; N, 2.31; Cl, 11.71.

EXAMPLE 41

5-{2-[2-(3-Chloro-phenyl)-2-hydroxy-ethylamino]-propyl}-benzo[1,3]dioxole-2,2-dicarboxylic acid bis-(2-cyclopentyl-ethyl) ester The title compound was prepared from 5-{2-[2-(3-chloro-phenyl)-2-hydroxy-ethylamino]-propyl}-benzo[1,3]dioxole-2,2-dicarboxylic acid and 2-cyclopentylethanol according to the procedure of Example 30 as an amber gum (HCl salt); $^1$H NMR (CDCl$_3$) δ 1.32 (d, J=6.3 Hz, 3H), 1.60 (m, 20H), 2.80 (m, 1H), 2.90 (m, 2H), 3.15 (m, 1H), 3.20 (m, 1H), 3.48 (m, 2H), 4.30 (t, J=6.9 Hz, 4H), 5.50 (bd, 1 H), 6.80 (m, 3H), 7.25 (m, 2H), 7.43 (s, 1H), 8.70 (bs, 1H), 10.10 (bs, 1H); IR (KBr): 1765 cm$^{-1}$ (C=O); MS (CI) m/z 614 (MH$^+$); $[α]_D^{25}$ −24° (c, 1.0, CHCl$_3$). Anal. Calcd. for C$_{34}$H$_{44}$ClNO$_7$·HCl: C, 62.77; H, 6.82; N, 2.15; Cl, 10.90. Found: C, 64.04; H, 8.24; N, 1.62; Cl, 8.99.

General Method to Prepare 5-{2-[2-(3-Chloro-phenyl)-2-hydroxy-ethylamino]-propyl}-benzo[1,3]dioxole-2,2-dicarboxylic acid bis-acetoxy-alkyl esters

Step 1

Preparation of Acyloxyalkyl Iodides

These esters were prepared by reacting the appropriate acid chlorides with formaldehyde or acetaldehyde in the presence of a catalytic amount of anhyrous ZnCl$_2$ according to Ulich, L. H. and Adams, R. J. *Amer. Chem. Soc.* 1921, 43, 660–666. The resultant acyloxyalkyl chlorides were converted in to the corresponding acyloxyalkyl iodide derivatives by reacting them with NaI in boiling benzene according to Fujimoto, K., Ishihara, S., Yanagisawa, H., Ide, J., Nakayama, E., Nakao, H., Sugawara, S., Iwata, M. J. *Antibiotics* 1987, 19, 370.

Step 2

5-{2-[2-(3-Chlorophenyl)-2-hydroxyethylamino]-propyl}-benzo[1,3]dioxole-2,2-dicarboxylic acid disilver salt To a stirred solution of 5-{2-[2-(3-chlorophenyl)-2-hydroxyethylamino]-propyl}-benzo[1,3]dioxole-2,2-dicarboxylic acid disodium salt (3.0 gm, 6.0 mmol) in distilled water, (in the dark) a solution of AgNO$_3$ (2.3 g, 12.0 mmol) was added dropwise. After stirring at room temperature for 1 h the separated solid was filtered and washed with water and acetone. The solid was dried at room temperature under vacuum to give a colorless solid; yield 100%; mp 183–185; M+H 422.1.

Step 3

5-{2-[2-(3-Chloro-phenyl)-2-hydroxy-ethylamino]-propyl}-benzo[1,3]dioxole-2,2-dicarboxylic acid bis-acetoxyalkyl esters To a stirred suspension of 5-{2-[2-(3-chlorophenyl)-2-hydroxyethylamino]-propyl}-benzo]1,3]dioxole-2,2- dicarboxylic acid disilver salt (2.0 gms, 3 mmol) in anhydrous chloroform the appropriately substituted acyloxyalkyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane. The compounds of Examples 42–58 below were prepared according to this general procedure.

EXAMPLE 42

5-{2-[2-(3-Chloro-phenyl)-2-hydroxyethylamino] propyl}benzo[1,3] dioxole-2,2-dicarboxylic acid bis-acetoxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform, acetoxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield an ivory color solid; mp 132–134; yield 97%; M+H 566.

EXAMPLE 43

5-{2-[2-(3-Chloro-phenyl)-2-hydroxyethylamino] propyl}benzo[1,3] dioxole-2,2-dicarboxylic acid bis-propionyloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform, propionyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a colorless solid; mp 118–20; yield 88%; M+H 594.

EXAMPLE 44

5-{2-[2-(3-Chloro-phenyl)-2-hydroxyethylamino] propyl}benzo[1,3] dioxole-2,2-dicarboxylic acid bis-butyryloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform butyryloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 70–72 (dec); yield 85%; M+H 622.

EXAMPLE 45

5-{2-[2-(3-Chloro-phenyl)-2-hydroxyethylamino] propyl}benzo[1,3] dioxole-2,2-dicarboxylic acid bis-isobutyryloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform isobutyryloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 114–116 (dec); yield 78%; M+H 622.

EXAMPLE 46

5-{2-[2-(3-Chloro-phenyl)-2-hydroxyethylamino] propyl}benzo[1,3] dioxole-2,2-dicarboxylic acid bis-heptanoyloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform heptanoyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 94–96; yield 18%; M+H 707.

EXAMPLE 47

5-{2-[2-(3-Chloro-phenyl)-2-hydroxyethylamino] propyl}benzo[1,3] dioxole-2,2-dicarboxylic acid bis-(4-methyl-pentanoyloxymethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform pentanoyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 105–108 (dec); yield 19%; M+H 679.

EXAMPLE 48

5-{2-[2-(3-Chloro-phenyl)-2-hydroxyethylamino]propyl}benzo[1,3] dioxole-2,2-dicarboxylic acid bis-hexanoyloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform hexanoyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 106–109; yield 20%; M+H 679.

EXAMPLE 49

5-{2-[2-(3-Chloro-phenyl)-2-hydroxyethylamino]propyl}benzo[1,3] dioxole-2,2-dicarboxylic acid bis-(2,2-dimethyl-propionyloxymethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 2,2-dimethylpropionyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a ivory solid; mp 72 (dec); yield, 48%; M+H 651.

EXAMPLE 50

5-{2-[2-(3-Chloro-phenyl)-2-hydroxyethylamino]propyl}benzo[1,3] dioxole-2,2-dicarboxylic acid bis-cyclohexanecarbonyloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform cyclohexanecarbonyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 86 (dec); yield 52%; M+H 703.

EXAMPLE 51

5-{2-[2-(3-Chloro-phenyl)-2-hydroxyethylamino]propyl}benzo[1,3] dioxole-2,2-dicarboxylic acid bis-(1-propionyloxy-ethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 1-propionyloxyethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 130–132 (dec); yield, 68%; M+H 622

EXAMPLE 52

5-{2-[2-(3-Chloro-phenyl)-2-hydroxyethylamino]propyl}benzo[1,3] dioxole-2,2-dicarboxylic acid bis-[1-(2,2-dimethyl-propionyloxy-ethyl) ester To a stirred suspension of 5-{2-[2-(3-chlorophenyl)-2-hydroxyethylamino]-propyl)-benzo[1,3]dioxole-2,2-dicarboxylic acid disilver salt (2.0 gms, 3 mmol) in anhydrous chloroform 1-(2,2-dimethylpropionyloxy)ethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 92; yield, 58%; M+H 679.

EXAMPLE 53

5-{2-[2-(3-Chloro-phenyl)-2-hydroxyethylamino]propyl}benzo[1,3] dioxole-2,2-dicarboxylic acid bis-(3,3-dimethyl-butyryloxymethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 3,3-dimethylbutyryloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 104–105 (dDec); yield 98%; M+H 678.

EXAMPLE 54

5-{2-[2-(3-Chloro-phenyl)-2-hydroxy-ethylamino]propyl}benzo[1,3] dioxole-2,2-dicarboxylic acid bis-[1-(3,3-dimethyl-butyryloxy)-ethyl)}ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 3,3-dimethylbutyryloxyethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 96–98 (dec); yield, 72%; M+H 706.

EXAMPLE 55

5-{2-[2-(3-Chloro-phenyl)-2-hydroxy-ethylamino]propyl}benzo[1,3]dioxole-2,2-dicarboxylic acid bis-(3-cyclopentyl-propionyloxymethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 3-cyclopentylpropionyloxy iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 155–157 (dec); yield, 98%; M+H 730.

EXAMPLE 56

5-{2-[2-(3-Chloro-phenyl)-2-hydroxy-ethylamino]propyl}benzo[1,3]dioxole-2,2-dicarboxylic acid bis-benzoyloxymethyl ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform benzoyloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a white solid; mp 150–153 (dec); yield 98%; M+H 690.

EXAMPLE 57

5-{2-[2-(3-Chloro-phenyl)-2-hydroxyethylamino]propyl}benzo[1,3] dioxole-2,2-dicarboxylic acid bis-(benzoyloxy-ethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 1-benzoyloxyethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield an ivory solid; mp 82–83 (dec); yield 96%; M+H 718.

EXAMPLE 58

5-{2-[2-(3-Chloro-phenyl)-2-hydroxyethylamino]propyl}benzo[1,3] dioxole-2,2-dicarboxylic acid bis-(2,2-dimethyl-butyryloxymethyl) ester To a stirred suspension of 5-{2-[2-(3-chlorophenyl)-2-hydroxyethylamino]-propyl}-benzo[1,3]dioxole-2,2-dicarboxylic acid disilver salt (2.0 gms, 3 mmol) in anhydrous chloroform 2,2-dimethylbutyryloxymethyl iodide (9 mmol) dissolved in chloroform (30 mL) was added. The reaction mixture was stirred at room temperature, under dark for 16 h. The reaction mixture was filtered and washed with 5% $Na_2S_2O_3$ solution in distilled water. The chloroform layer was dried over anhydrous $MgSO_4$ and filtered. It was evaporated to dryness and the residue obtained was dissolved in 5 mL of ethyl acetate and 60 mL of hexane was added. The separated solid was filtered and washed with hexane to yield a ivory solid; mp 121–123 (dec); yield 37%; M+H 679.

EXAMPLE 59

5-{(2R)-2-[(2R)-2-(3-Chloro-phenyl)-2-hydroxy-ethylamino]-propyl}-benzo[1,3]dioxole-2,2-dicarboxylic acid bis-[1-(cyclohexyloxycarbonyloxy)-ethyl] ester Cyclohexyl 1-iodoethyl carbonate (5.6 g, 18 8 mmol) in $CHCl_3$ (10 mL) was added dropwise into a cold (0° C.) suspension of (R,R)-5-[2-[2-(3-chlorophenyl)-2-hydroxyethylamino]propyl]-1,3-benzodioxole-2,2-dicarboxylic acid disilver salt (4.0 g, 6.3 mmol) and $CHCl_3$ (100 mL). After the addition, the mixture was allowed to come to room temperature and stirred for 24 h. Diethyl ether (300 mL) was added into the reaction mixture and the precipitated solids were filtered and discarded. The filtrate was concentrated in vaccuo at room temperature and the residue was quickly chromatographed through silica gel, eluting anhydrous solvent (EtOAc/hexane, 1/1), to give a light yellow solid (1.25 g, 26% yield): mp 78–81° C., (+)FAB m/e 762 (M+H)$^+$. Analysis for: $C_{38}H_{48}ClNO_{13}$: Calcd: C, 59.89; H, 6.35; N, 1.84; Found: C, 60.88; H, 6.53; N, 1.99.

EXAMPLE 60

5-{2-[2-(3-Chloro-phenyl)-2-hydroxy-ethylamino]-propyl}benzo[1,3]dioxole-2,2-dicarboxylic acid bis-amide A mixture of 5-{2-[2-(3-chloro-phenyl)-2-hydroxy-ethylamino]-propyl)-benzo[1,3]dioxole-2,2-dicarboxylic acid bis-ethyl ester (2.4 g, 5 mmol) and ammonia (excess) was stirred for 48 h. The reaction mixture was concentrated and the residue obtained was extracted with chloroform:methanol (3:1). It was washed with water and dried over anhydrous $MgSO_4$. The organic layer was filtered and concentrated. The residue obtained was chromatographed over silica gel eluted with 9:1 chloroform methanol to yield a brown solid; mp 98; yield. 1.0 g; 45%; M+H 420.

EXAMPLE 61

5-{2-[2-(3-Chloro-phenyl)-2-hydroxy-ethylamino]-propyl}-benzo[1,3]dioxole-2,2-dicarboxylic acid bis-2-propyl amide A mixture of 5-{2-[2-(3-chloro-phenyl)-2-hydroxy-ethylamino]-propyl}-benzo-[1,3]dioxole-2,2-dicarboxylic acid bis-ethyl ester (2.4 g, 5 mmol) and isopropylamine (10 mL, excess) was refluxed in ethanol for 48 h. The reaction mixture was concentrated and the residue obtained was extracted with chloroform:methanol (3:1). It was washed with water and dried over anhydrous $MgSO_4$. The organic layer was filtered and concentrated. The residue obtained was chromatographed over silica gel eluted with 9:1 chloroform:methanol to yield a colorless spongy solid; mp 60; yield 1.5 g; 60%; M+H 504.

EXAMPLE 62

5-{2-[2-(3-Chloro-phenyl)-2-hydroxy-ethylamino]-propyl}-benzo[1,3]dioxole-2,2-dicarboxylic acid bis-n-butyl amide A mixture of 5-{2-[2-(3-chloro-phenyl)-2-hydroxy-ethylamino]-propyl)-benzo-[1,3]dioxole-2,2-dicarboxylic acid bis-ethyl ester (2.4 g, 5 mmol) and n-butylamine (10 mL, excess) was refluxed in ethanol for 48 h. The reaction mixture was concentrated and the residue obtained was extracted with chloroform:methanol (3:1). It was washed with water and dried over anhydrous $MgSO_4$. The organic layer was filtered and concentrated. The residue obtained was chromatographed over silica gel eluted with 9:1 chloroform:methanol to yield a brown semi solid; yield 1.6 g; 61%; M+H 532.

EXAMPLE 63

5-{2-[2-(3-Chloro-phenyl)-2-hydroxy-ethylamino]-propyl}-benzo[1,3]dioxole-2,2-dicarboxylic acid bis-phenylmethyl amide A mixture of 5-{2-[2-(3-chloro-phenyl)-2-hydroxy-ethylamino]-propyl}-benzo[1,3]dioxole-2,2-dicarboxylic acid bis-ethyl ester (2.4 g, 5 mmol) and benzylamine (10 mL, excess) was refluxed in ethanol for 48 h. The reaction mixture was concentrated and the residue obtained was extracted with chloroform:methanol (3:1). It was washed with water and dried over anhydrous $MgSO_4$. The organic layer was filtered and concentrated. The residue obtained was chromatographed over silica gel eluted with 9:1 chloroform:methanol to yield a colorless spongy solid; mp 101; yield 2.0 g; 67%; M+H 600.

EXAMPLE 64

5-{2-[2-(3-Chloro-phenyl)-2-hydroxy-ethylamino]-propyl}-benzo[1,3]dioxole-2,2-dicarboxylic acid bis-(2-furanylmethyl) amide A mixture of 5-{2-[2-(3-chloro-phenyl)-2-hydroxy-ethylamino]-propyl}-benzo[1,3]dioxole-2,2-dicarboxylic acid bis-ethyl ester (2.4 g, 5 mmol) and 2-furanylmethylamine (10 mL, excess) was refluxed in ethanol for 48 h. The reaction mixture was concentrated and the residue obtained was extracted with chloroform:methanol (3:1). It was washed with water and dried over anhydrous $MgSO_4$. The organic layer was filtered and concentrated. The residue obtained was chromatographed over silica gel eluted with 9:1 chloroform:methanol to yield a brown solid; mp 50; yield 400 mg; 14%; M+H 581.

EXAMPLE 65

5-{2-[2-(3-Chloro-phenyl)-2-hydroxy-ethylamino]-propyl}-benzo[1,3]dioxole-2,2-dicarboxylic acid bis-(glycine ethyl ester) amide A mixture of glycine ethyl ester.HCl (1.1 gm, 8 mmol) and sodium methoxide (424 mg, 8 mmol) was stirred at room temperature in ethanol for fifteen minutes. At the end, 5-{2-[2-(3-chloro-phenyl)-2-hydroxy-ethylamino]-propyl}-benzo[1,3]dioxole-2,2-dicarboxylic acid bis-ethyl ester (970 mg, 2 mmol) was added to the reaction mixture and refluxed for 48 hours. At the end ethanol was removed. The residue obtained was added to ice cold water and seperated solid was filtered. The solid was dried and purified by silica gel column chromatography by eluting it with 3:1 chloroform:methanol to yield a colorless solid; yield 500 mg; 42%; M+H 592.

EXAMPLE 66

5-{2-[2-(3-Chloro-phenyl)-3-oxazolidinyl]-propyl}-benzo[1,3]dioxole-2,2-dicarboxylic acid 5-{2-[2-(3-Chloro-phenyl)-2-hydroxy-ethylamino]-propyl}-benzo[1,3]dioxole-2,2-dicarboxylic acid sodium salt (0.46 g, 1.0 mmol) was dissolved in 4 mL of 37% formaldehyde, and stirred at room temperature for 0.5 h. Trifluoroacetic acid (0.23 g, 2.0 mmol) was then added dropwise, and the resulting white suspension was stirred for 24 h. The precipitate was filtered, washed with water, and dried in vacuo to give 0.40 g of white solid; $^1$H NMR ($CDCl_3$) δ 1.02 (d, J=6.4 Hz, 3H), 2.50 (m, 1H), 3.00 (m, 2H), 3.20 (m, 1H), 3.80 (m, 1H), 4.75 (d, J=4.5 Hz, 1H), 4.90 (d, J=4.5 Hz, 1H), 5.12 (t J=7.3 Hz, 1H), 6.70 (m, 1H), 6.86 (m, 2H), 7.40 (m, 2H), 7.50 (s, 1H); IR (KBr): 1740 $cm^{-1}$ (C=O); MS (CI) m/z 433 ($M^+$). Anal. Calcd. for $C_{21}H_{20}ClNO_7 \cdot HCl$: C, 58.14; H, 4.65; N, 3.23; Cl, 8.17. Found: C, 57.08; H, 4.78; N, 3.32; Cl, 7.51.

EXAMPLE 67

5-((2R)-2-{tert-Butoxycarbonyl-[(2R)-2-(3-chloro-phenyl)-2-hydroxy-ethyl]-amino}-propyl)-benzo[1,3]dioxole-2,2-dicarboxylic acid bis-diethylcarbamoylmethyl ester A mixture of 5-((2R)-2-{tert-butoxycarbonyl-[(2R)-2-(3-chloro-phenyl)-2-hydroxy-ethyl]-amino}-propyl)-benzo[1,3]dioxole-2,2-dicarboxylic acid (0.26 g, 0.5 mmol) and anhydrous potassium carbonate (0.28 g) in anhydrous dimethyl formamide was treated with 2-bromo-N,N-diethylacetamide (0.39 g, 2 mmol), and stirred at room temperature for 3 days. It was then diluted with water and hexanes, and the resulting suspension was filtered. The precipitate was washed with saturated sodium bicarbonate solution, water, and hexanes, and then dried in vacuo to give 0.27 g of white solid; $^1$H NMR ($CDCl_3$) δ 1.0–1.5 (m, 24H), 2.6 (m, 2H), 3.0–3.5 (m, 10H), 4.0 (m, 1H), 4.7–5.0 (m, 4H), 5.5, 6.0 (m, 1H), 6.80 (m, 3H), 7.26 (m, 2H); IR (KBr): 1772, 1668 $cm^{-1}$ (C=O); MS (ES) m/z 748 ($MH^+$).

EXAMPLE 68

5-{(2R)-2-[(2R)-2-(3-Chloro-phenyl)-2-hydroxy-ethylamino]-propyl}-benzo[1,3]dioxole-2,2-dicarboxylic acid bis-diethylcarbamoylmethyl ester A solution of 5-((2R)-2-{tert-butoxycarbonyl-[(2R)-2-(3-chloro-phenyl)-2-hydroxy-ethyl]-amino}-propyl)-benzo[1,3]dioxole-2,2-dicarboxylic acid bis-diethyl-carbamoylmethyl ester (0.16 g, 0.2 mmol) in methylene chloride (2 ml) was treated with 0.08 ml of trifluoroacetic acid at room temperature for 18 h. The mixture was then evaporated, and the residue washed with ether to give 0.12 g of white solid (TFA salt); $^1$H NMR (DMSO-$d_6$) δ 1.0–1.2 (m, 15H), 2.6 (m, 2H), 3.0–4.0 (m, 11H), 5.0 (m, 4 H), 6.1 (m, 1H), 6.80 (m, 3H), 7.26 (m, 2H), 8.7 (bs, 1H),9.2 (bs, 1H); IR (KBr): 1765,1654 $cm^{-1}$ (C=O); MS (ES) m/z 648 ($MH^+$).

EXAMPLE 69

5-{2-[2-(3-Chloro-phenyl)-2-hydroxy-ethylamino]-propyl}-benzo[1,3]dioxole-2,2-dicarboxylic acid cyclopropylmethyl ester The title compound was prepared from 5-{2-[2-(3-chloro-phenyl)-2-hydroxy-ethylamino]-propyl}-benzo[1,3]

dioxole-2,2-dicarboxylic acid and cyclopropylmethanol according to the procedure of Example 1 as an off-white solid; $^1$H NMR (DMSO) δ 0.25 (q,2H), 0.49 (q,2H), 1.01 (d,3H), 1.10 (m,1H), 2.49 (m, 1H), 2.85–3.20 (m,4H), 3.94 (d, 2H) 4.85 (bt, 1H), 6.58 (d, 1H), 6.76 (m,2H), 7.35(m, 3H), 7.46(s,1H); IR (KBr): 1653 cm$^{-1}$ (C=O), 1747 cm$^{-1}$ (C=O); MS (CI) m/z 476 (MH$^+$). Anal. Calcd. for $C_{24}H_{26}ClNO_7$: C, 60.57; H, 5.51; N, 2.94; Cl, 7.46. Found: C, 56.38; H, 5.16; N, 2.61; Cl, 7.60.

EXAMPLE 70

5-{2-[2-(3-Chloro-phenyl)-2-hydroxy-ethylamino]-propyl}-benzo[1,3]dioxole-2,2-dicarboxylic acid cyclobutylmethyl ester The title compound was prepared from 5-{2-[2-(3-chloro-phenyl)-2-hydroxy-ethylamino]-propyl}-benzo[1,3]dioxole-2,2-dicarboxylic acid and cyclobutylmethanol according to the procedure of Example 1 as an off-white solid; $^1$H NMR (DMSO) δ 1.01 (d,3H), 1.75(m,4H), 1.92 (m,2H), 2.49 (m, 1H), 2.65 (m,1H), 2.85–3.20 (m,4H), 4.09 (d, 2H), 4.85 (bt, 1H), 6.58 (d, 1H), 6.76 (m,2H), 7.35(m, 3H), 7.46(s,1H); IR (KBr): 1652 cm$^-$ (C=O), 1761 cm$^{-1}$ (C=O); MS (CI) m/z 490 (MH$^+$). Anal. Calcd. for $C_{25}H_{28}ClNO_7$: C, 61.29; H, 5.76; N, 2.86; Cl, 7.24. Found: C, 57.13; H, 5.15; N, 2.43; Cl, 6.83.

EXAMPLE 71

5-{2-[2-(3-Chloro-phenyl)-2-hydroxy-ethylamino]-propyl}-benzo[1,3]dioxole-2,2-dicarboxylic acid bis 2-(3-Thienyl)ethyl-ester The title compound was prepared from 5-}2-[2-(3-chloro-phenyl)-2-hydroxy-ethylamino]-propyl}-benzo[1,3]dioxole-2,2-dicarboxylic acid and 2-(3-thienyl)ethanol according to the procedure of Example 1 as yellow crystals (HCl salt); $^1$H NMR (CDCl$_3$) δ 1.33 (d, 3H), 2.82 (m, 1H), 2.95 (t,4H), 3.20(m, 2H), 3.48 (bd, 2H), 4.45 (t, 4H), 5.50 (bd, 1H), 5.60(bs,1H), 6.75–7.00(m, 7H), 7.21–7.32(m, 5H), 7.45(s,1H), 8.70 (bs, 1H), 10.10 (bs, 1H); IR (KBr): 1765 cm$^{-1}$ (C=O); MS (CI) m/z 642 (MH$^+$); $[α]_D^{25}$ –21° (c, 1.0, CHCl$_3$). Anal. Calcd. for $C_{34}H_{32}ClS_2NO_7 \cdot HCl$: C, 56.63; H, 4.75; N, 2.06; S, 9.45; Cl, 10.46. Found: C, 55.89; H, 4.95; N, 1.87; S, 9.45; Cl, 9.95.

EXAMPLE 72

5-{2-[2-(3-Chloro-phenyl)-2-hydroxy-ethylamino]-propyl}-benzo[1,3]dioxole-2,2-dicarboxylic acid 2-(3-Thienyl)ethyl ester The title compound was prepared from 5-{2-[2-(3-chloro-phenyl)-2-hydroxy-ethylamino]-propyl}-benzo[1,3]dioxole-2,2-dicarboxylic acid bis 2-(3-thienyl)ethyl-ester according to the procedure of Example 22 as an off-white solid; $^1$H NMR (DMSO) δ 0.96 (d,3H), 2.45 (m, 1H), 2.72–3.10 (m,6H), 4.25(t,2H), 4.80 (bt, 1H), 5.92 (bs, 1H), 6.60(d,1H), 6.79(d,2H), 7.05(d,1H), 7.17(s,1H), 7.30–7.50 (5H); IR (KBr): 1652 cm$^{-1}$ (C=O), 1751 cm$^{-1}$ (C=O); MS (CI) n/z 532 (MH$^+$). Anal. Calcd. for $C_{26}H_{26}ClSN_7$: C, 58.70; H, 4.93; N, 2.63; S, 6.01; Cl, 5.98. Found: C, 54.17; H, 4.44; N, 2.24; S, 5.13; Cl, 5.98.

EXAMPLE 73

5-{2-[2-(3-Chloro-phenyl)-2-hydroxy-ethylamino]-propyl}-benzo[1,3]dioxole-2,2-dicarboxylic acid bis 2-(Chloro)ethyl ester The title compound was prepared from 5-{2-[2-(3-chloro-phenyl)-2-hydroxy-ethylamino]-propyl}-benzo[1,3]dioxole-2,2-dicarboxylic acid and 2-chloroethanol according to the procedure of Example 1 as yellow crystals (HCl salt); $^1$H NMR (DMSO) δ 1.13 (d, 3H), 2.65 (m, 1H), 3.15–3.52(m, 4H), 3.85 (t, 4H), 4.60 (t, 4 H), 5.55 (bd, 1H), 6.40(bs,1H), 6.86(d,1H), 7.08(m,2H), 7.40–7.58(m,4H), 8.85 (bs, 1H), 9.40 (bs, 1H); IR (KBr): 1770 cm$^{-1}$ (C=O); MS (CI) m/z 548 (MH$^+$); $[α]_D^{25}$ –28° (c, 1.0, DMSO). Anal. Calcd. for $C_{24}H_{26}C_{13}NO_7 \cdot HCl$: C, 49.42; H, 4.67; N, 2.40;Cl, 25.9. Found: C, 49.69; H, 4.38; N, 2.32; Cl, 23.20.

EXAMPLE 74

5-{(2R)-2-[(2R)-2-(3-Chloro-phenyl)-2-hydroxy-ethylamino]-propyl}-benzo[1,3]dioxole-2,2-dicarboxylic acid bis-(2-ethylbutyl) ester The title compound was prepared from 5-{2-[2-(3-chloro-phenyl)-2-hydroxy-ethylamino]-propyl}-benzo[1,3]dioxole-2,2-dicarboxylic acid and 2-ethylbutanol according to the procedure of Example 1 as an off-white gum (HCl salt); $^1$H NMR (CDCl$_3$) δ 0.80–0.95 (m, 12H), 1.25–1.45 (m, 10H), 1.50–1.65 (m, 3H), 2.75–2.85 (m, 1H), 3.10–3.40 (m, 1H), 3.47–3.49 (m, 2H), 4.25 (d, 5H), 5.50 (d, 1H), 6.70–6.80 (m, 1H), 6.80–6.90 (m, 2H), 7.20–7.45 (m, 3H), 7.46 (s, 1H), 8.74 (bs, 1 H), 10.06 (bs, 1H); IR (KBr): 2964 cm$^{-1}$ (—OH), 1766 cm$^{-1}$ (C=O); MS (ES) m/z 590.4 (MH$^+$); $[α]_D^{25}$ –21° (c, 1.0, CHCl$_3$). Anal. Calcd. for $C_{32}H_{44}ClNO_7 \cdot HCl$: C, 61.34; H, 7.08; N, 2.24; Cl, 11.32. Found: C, 61.09; H, 7.46; N, 2.12; Cl, 10.77.

EXAMPLE 75

5-{(2R)-2-[(2R)-2-(3-Chloro-phenyl)-2-hydroxy-ethylamino]-propyl}-benzo[1,3]dioxole-2,2-dicarboxylic acid bis-(3-methylbutyl)ester The title compound was prepared from 5-{2-[2-(3-chloro-phenyl)-2-hydroxy-ethylamino]-propyl}-benzo[1,3]dioxole-2,2-dicarboxylic acid and 3-methylbutanol according to the procedure of Example 1 as an off-white foam (HCl salt); $^1$H NMR (CDCl$_3$) δ 0.90 (d, 12H), 1.35 (d, 2H), 1.55–1.80 (m, 6H), 2.70–2.85 (m, 1H), 3.45–3.55 (m, 3H), 4.30 (t, 4H), 5.45 (bd, 1H), 5.65 (bs, 1H), 6.70–6.80 (m, 1 H), 6.80–6.90 (m, 3H), 7.25–7.35 (m, 3H), 7.43 (s, 1H), 8.74 (bs, 1H), 10.08 (bs, 1H); IR (KBr): 3303 cm$^{-1}$ (—OH), 1765 cm$^{-1}$ (C=O); MS (ES) m/z 562.4 (MH$^+$); $[α]_D^{25}$ –24° (c, 1.0, CHCl$_3$). Anal. Calcd. for $C_{30}H_{40}ClNO_7 \cdot HCl$: C, 60.20; H, 6.74; N, 2.34; Cl, 11.85. Found: C, 59.98; H, 7.04; N, 2.24; Cl, 12.09.

EXAMPLE 76

5-{(2R)-2-[(2R)-2-(3-Chloro-phenyl)-2-hydroxy-ethylamino]-propyl}-benzo[1,3]dioxole-2,2-dicarboxylic acid (3-methylbutyl)ester The title compound was prepared from 5-{(2R)-2-[(2R)-2-(3-chloro-phenyl)-2-hydroxy-ethylamino]-propyl}-benzo[1,3]dioxole-2,2-dicarboxylic acid bis-(3-methylbutyl)ester according to the procedure of Example 22 as an off-white solid; $^1$H NMR (DMSO) δ 0.80–0.85 (m, 6H), 1.02–1.09 (m, 3H), 1.45 (q, 2H), 1.55–1.70 (m, 1H), 3.01–3.05 (m, 2H), 3.15–3.25 (m, 1H), 3.26–3.40 (m, 2H), 4.15 (t, 2H), 5.00–5.08 (m, 1H), 6.45 (bs, 1H), 6.55–6.65 (m, 1H), 6.75–6.90 (m, 2H), 7.45–7.49 (m, 5H), 7.51 (s, 1H); IR (Kbr): 3394 cm$^{-1}$ (—OH), 1651 cm$^{-1}$ (C=O); MS (ES) m/z 492.0 (MH$^{+):}$ $[α]_D^{25}$ –22° (c, 1.0, CHCl$_3$). Anal. Calcd. for $C_{25}H_{30}ClNO_7$: C, 61.04; H, 6.15; N, 2.85; Cl, 7.20. Found: C, 59.80; H, 6.10; N, 2.89; Cl, 7.10.

EXAMPLE 77

5-{(2R)-2-[(2R)-2-(3-Chloro-phenyl)-2-hydroxy-ethylamino]-propyl}-benzo[1,3]dioxole-2,2-dicarboxylic acid bis-adamantan-1-ylmethyl ester The title compound was prepared from 5-{2-[2-(3-chloro-phenyl)-2-hydroxy-ethylamino]-propyl}-benzo[1,3]dioxole-2,2-dicarboxylic acid and adamantan-1-ylmethanol according to the procedure of Example 1 as a white solid (HCl salt); $^1$H NMR (CDCl$_3$) δ 1.25 (m, 2H), 1.35 (d, 3H), 1.51 (s, 12H), 1.55–1.61 (m, 2H), 1.61–1.67 (m, 4H), 1.67–1.75 (m, 6H), 1.97 (s, 4H), 3.20 (s, 2H), 3.42–3.49 (m, 2H), 3.88 (s, 4H), 4-11-4.16 (q, 1H), 5.45 (bd, 1H), 5.65 (bd, 1H), 6.75 (m, 1H), 6.78–6.89 (m, 2H), 7.23–7.30 (m, 3H), 7.44 (s, 1H), 8.74 (bs, 1H), 10.115 (bs, 1H); IR (KBr) 3418 cm$^{-1}$ (—OH), 1767 cm$^{-1}$ (C=O); MS (ES) m/z 718.4 (MH$^+$); [α]$_D^{25}$ -15° (c, 1.0, CHCl$_3$). Anal. Calcd. for C$_{42}$H$_{52}$ClNO$_7$: C, 68.94; H, 9.22; N, 1.90; Cl, 9.40. Found: C, 67.48; H, 7.49; N, 1.48; Cl, 8.10.

EXAMPLE 78

5-{(2R)-2-[(2R)-2-(3-Chloro-phenyl)-2-hydroxy-ethylamino]-propyl}-benzo[1,3]dioxole-2,2-dicarboxylic acid bis-(2,2-dimethyl-propyl) ester The title compound was prepared from 5-{2-[2-(3-chloro-phenyl)-2-hydroxy-ethylamino]-propyl}-benzo[1,3]dioxole-2,2-dicarboxylic acid and 2,2-dimethylpropanol according to the procedure of Example 1 as an off-white foam (HCl salt); $^1$H NMR (CDCl$_3$) δ 0.924 (s, 18H), 1.45 (d, 2H), 1.75 (s, 2H), 2.80 (m, 1H), 3.17 (m, 1H), 3.45 (m, 1H), 3.98 (s, 4H), 5.45–5.55 (bd, 1H), 5.63–5.67 (bs, 1H), 6.75–6.80 (m, 2H), 6.80–6.89 (m, 2H), 7.25–7.35 (m, 3H), 7.440 (s, 1H), 8.75 (bs, 1H), 10.10 (bs, 1H); IR (KBr) 3355 cm$^{-1}$ (—OH), 1767 cm$^{-1}$ (C=O); MS (ES) m/z 562.3 (MH$^+$); [α]$_D^{25}$ -23° (c, 1.0, CHCl$_3$). Anal. Calcd. for C$_{30}$H$_{40}$ClNO$_7$: C, 60.20; H, 6.90; N, 2.34; Cl, 11.85. Found: C, 59.74; H, 6.97; N, 2.23; Cl, 11.60.

EXAMPLE 79

5-{(2R)-2-[(2R)-2-(3-Chloro-phenyl)-2-hydroxy-ethylamino]-propyl}-benzo[1,3]dioxole-2,2-dicarboxylic acid adamantan-1-ylmethyl ester The title compound was prepared from 5-{(2R)-2-[(2R)-2-(3-chloro-phenyl)-2-hydroxy-ethylamino]-propyl}-benzo[1,3]dioxole-2,2-dicarboxylic acid bis-adamantan-1-ylmethyl ester according to the procedure of Example 22 as an off-white solid; $^1$H NMR (DMSO) δ 1.03–1.09 (m, 3H), 1.44 (s, 6H), 1.45–1.64 (m, 8H), 1.86 (s, 4H), 3.02–3.15 (m, 1H), 3.25–3.55 (m, 2H), 3.70–3.80 (m, 2H), 4.58 (s, 2H), 5.06–5.10 (m, 1H), 6.52–6.65 (m, 1H), 6.79–6.88 (m, 2H), 7.32–7.49 (m, 3H), 7.49 (s, 1H); IR (KBr) 3384 cm$^{-1}$ (—OH), 1758 cm$^{-1}$ (C=O), 1651 cm$^{-1}$ (C=O); MS (ES) m/z 570.3 (MH$^+$); [α]$_D^{25}$ -29° (c, 1.0, CHCl$_3$). Anal. Calcd. for C$_{31}$H$_{36}$ClNO$_7$: C, 65.31; H, 6.37; N, 2.46; Cl, 6.39. Found: C, 64.19; H, 6.20; N, 2.33; Cl, 6.33.

EXAMPLE 80

5-{(2R)-2-[(2R)-2-(3-Chloro-phenyl)-2-hydroxy-ethylamino]-propyl}-benzo[1,3]dioxole-2,2-dicarboxylic acid (2,2-dimethyl-propyl)ester The title compound was prepared from 5-{(2R)-2-[(2R)-2-(3-chloro-phenyl)-2-hydroxy-ethylamino]-propyl}-benzo[1,3]dioxole-2,2-dicarboxylic acid bis-(2,2-dimethyl-propyl) ester according to the procedure of Example 22 as a white solid; $^1$H NMR (DMSO) δ 0.868 (s, 9H), 1.02–1.06 (m, 3H),3.00–3.02 (m, 1H), 3.24–3.30 (m, 1H), 3.35 (s, 5H), 3.80 (t, 2H), 4.55 (s, 1H), 5.03 (m, 1H), 6.52 (m, 1H), 6.61 (m, 1H), 6.79 (m, 1H), 7.34 (m, 3H), 7.48 (s, 1H); IR (KBr) 3398 cm$^{-1}$ (—OH), 1748 cm$^{-1}$ (C=O), 1654 cm$^{-1}$ (C=O); MS (ES) m/z 492.3 (MH$^+$); [α]$_D^{25}$ -93° (c, 1.0, CHCl$_3$). Anal. Calcd. for C$_{25}$H$_{30}$ClNO$_7$: C, 61.04; H, 6.15; N, 2.85; Cl, 7.21. Found: C, 56.96; H,5.65; N, 2.63; Cl, 7.05.

EXAMPLE 81

5-{(2R)-2-[(2R)-2-(3-Chloro-phenyl)-2-hydroxy-ethylamino]-propyl}-benzo[1,3]dioxole-2,2-dicarboxylic acid (3,3-dimethylbutyl) ester The title compound was prepared from 5-{(2R)-2-[(2R)-2-(3-chloro-phenyl)-2-hydroxy-ethylamino]-propyl}-benzo[1,3]dioxole-2,2-dicarboxylic acid bis-(3-methylbutyl)ester according to the procedure of Example 22 as an off-white solid; $^1$H NMR (DMSO) δ 0.87 (s, 9H), 1.04 (m, 3H), 1.50 (t, 2H), 3.34 (s, 8H), 4.20 (t, 2H), 4.95–5.05 (m, 1H), 6.35 (m, 1H), 6.60 (m, 1H), 6.75 (m, 1H), 7.34–7.46 (m, 3H), 7.48 (s, 1H); IR (KBr) 3410 cm$^{-1}$ (—OH), 1745 cm$^{-1}$ (C=O), 1651 cm$^{-1}$ (C=O); MS (ES) m/z 506.4 (MH$^+$); Anal. Calcd. for C$_{26}$H$_{32}$ClNO$_7$: C, 61.72; H, 6.37; N, 2.77; Cl, 7.01. Found: C, 60.69; H, 6.20; N, 2.63; Cl,7.06.

EXAMPLE 82

5-{(2R)-2-[(2R)-2-(3-Chloro-phenyl)-2-hydroxy-ethylamino]-propyl}-benzo[1,3]dioxole-2,2-dicarboxylic aicd bis-(1-methyl-cyclohexylmethyl) ester The title compound was prepared from 5-{2-[2-(3-chloro-phenyl)-2-hydroxy-ethylamino]-propyl}-benzo[1,3]dioxole-2,2-dicarboxylic acid and 1-methylcyclohexyl-methanol according to the procedure of Example 1 as an off-white solid; $^1$H NMR (DMSO-d$_6$,400 MHz) δ 0.84 (s, 6H, CH$_3$, CH$_3$), 1.09 (d, J=6.4 Hz, 3H, CH$_3$), 1.1–1.4 (m, 20H, cyclohexyl), 2.6 (m, 1H, CH), 3–3.3 (m, 3H, CH, CH$_2$), 3.4 (brs, 1H, CH), 4.04 (s, 4H, OCH$_2$, OCH$_2$), 5.05 (m, 1H, CH), 6.35 (d, J=4.17 Hz, 1H, OH), 6.85 (dd, J=7.9, 1.32 Hz, 1H, Ar—H), 7.07 (s, 1H, Ar—H), 7.09 (d, J=8.35 Hz, Ar—H), 7.38–7.42 (m, 3H, Ar—H), 7.5 (s, 1H, Ar—H), 8.8 (brs, 1H, NH), 9.4 (brs, 1H, NH); IR (KBr, cm$^{-1}$) 3400 (OH), 2900 (NH), 1760 (CO); MS m/e 641 (M$^+$); Analysis for: C$_{36}$H$_{48}$ClNO$_7$×HCl: Calc'd: C, 63.71; H, 7.28; N, 2.06; Found: C, 63.72; H, 7.03; N, 1.91.

EXAMPLE 83

5-{(2R)-2-[(2R)-2-(3-Chloro-phenyl)-2-hydroxy-ethylamino]-propyl}-benzo[1,3]dioxole-2,2-dicarboxylic aicd bis-(2-cyclohexyl-2-methyl-propyl) ester The title compound was prepared from 5-{2-[2-(3-chloro-phenyl)-2-hydroxy-ethylamino]-propyl}-benzo-[1,3]dioxole-2,2-dicarboxylic acid and 2-cyclohexyl-2-methylpropanol according to the procedure of Example 1 as an off-white solid; $^1$H NMR (DMSO-d$_6$,400 MHz) δ 1.1 (s, 6H, CH$_3$, CH$_3$), 1.45 (s, 6H, CH$_3$, CH$_3$), 1.5 (s, 6H, CH$_3$, CH$_3$), 2.6 (m, 1H, CH), 3–3.3 (m, 3H, CH, CH$_2$), 3.4 (brs, 1H, CH), 4.04 (s, 4H, OCH$_2$, OCH$_2$), 5.05 (m, 1H, CH), 6.35 (d, J=4.17 Hz, 1H, OH), 6.85 (dd, J=7.9, 1.32 Hz, 1H, Ar—H), 7.07 (m, 2H, Ar—H), 7.38–7.42 (m, 3H, Ar—H), 7.5 (s, 1H, Ar—H), 8.8 (brs, 1H, NH), 9.4 (brs, 1H, NH); IR (KBr, cm$^{-1}$) 3400 (OH), 2900 (NH), 1760 (CO); MS m/e 698 (M+H)$^+$; Analysis for: C$_{40}$H$_{56}$ClNO$_7$×HCl: Calc'd: C, 65.38; H, 7.82; N, 1.91; Found: C, 65.32; H, 7.96; N, 1.94.

EXAMPLE 84

5-{(2R)-2-[(2R)-2-(3-Chloro-phenyl)-2-hydroxy-ethylamino]-propyl}-benzo[1,3]dioxole-2,2-dicarboxylic aicd bis-(2-methyl-2-nitro-propyl) ester The title compound was prepared from 5-{2-[2-(3-chlorophenyl)-2-hydroxy-ethylamino]-propyl}-benzo[1,3]dioxole-2,2-dicarboxylic acid and 2-methyl-2-nitropropanol according to the procedure of Example 1 as an off-white solid; $^1$H NMR (DMSO-d$_6$,400 MHz) δ 0.78 (s, 12H, 4×CH$_3$), 0.8–1.0 (m, 4H, CH$_2$), 1–1.2 (m, 11H, cyclohexyl, CH$_3$), 1.5–1.65 (m, 10 H, cyclohexyl), 2.6 (m, 1H, CH), 3–3.3 (m, 3H, CH, CH$_2$), 3.4 (brs, 1H, CH), 4.04 (s, 4H, OCH$_2$, OCH$_2$), 5.05 (m, 1H, CH), 6.35 (d, J=4.17 Hz, 1H, OH), 6.83 (dd, J=7.9, 1.32 Hz, 1H, Ar—H), 7.06 (s 1H, Ar—H), 7.09 (d, J=8.35 Hz), 7.38–7.42 (m, 3H, Ar—H), 7.5 (s, 1H, Ar—H), 8.8 (brs, 1H, NH), 9.4 (brs, 1H, NH); IR (KBr, cm$^{-1}$) 3400 (OH), 2900 (NH), 1760 (CO); Analysis for: C$_{28}$H$_{34}$ClN$_3$O$_{11}$×HCl: Calc'd: C, 50.92; H, 5.34; N, 6.36; Found: C, 50.72; H, 5.42; N, 5.96.

EXAMPLE 85

5-{(2R)-2-[(2R)-2-(3-Chloro-phenyl)-2-hydroxy-ethylamino]-propyl}-benzo[1,3]dioxole-2,2-dicarboxylic aicd bis-(2,2,4-trimethyl-pentyl) ester The title compound was prepared from 5-{2-[2-(3-chlorophenyl)-2-hydroxy-ethylamino]-propyl}-benzo[1,3]dioxole-2,2-dicarboxylic acid and 2,2,4-trimethylpentanol according to the procedure of Example 1 as an off-white solid; $^1$H NMR (DMSO-d$_6$,400 MHz) δ 0.65–0.9 (m, 24H, 8×CH$_3$), 1.09 (d, J=6.4 Hz, 3H, CH$_3$), 1.1–1.4 (m, 4H, CH$_2$, CH$_2$), 2.62 (m, 1H, CH), 3–3.3 (m, 3H, CH, CH$_2$), 3.4 (brs, 1H, CH), 4.04 (s, 4H, OCH$_2$, OCH$_2$), 5.05 (m, 1H, CH), 6.34 (d, J=3.95 Hz, 1H, OH), 6.85 (dd, J=7.9, 1.32 Hz, 1H, Ar—H), 7.07 (m, 2H, Ar—H), 7.38–7.42 (m, 3H, Ar—H), 7.5 (s, 1H, Ar—H), 8.7 (brs, 1H, NH), 9.1 (brs, 1H, NH); IR (KBr, cm$^{-1}$) 3300 (OH), 2900 (NH), 1760 (CO); MS m/e 646 (M+H)$^+$; Analysis for: C$_{36}$H$_{52}$ClNO$_7$×HCl: Calc'd: C, 63.33; H, 7.83; N, 2.05; Found: C, 62.96; H, 7.71; N, 2.44.

EXAMPLE 86

5-{(2R)-2-[(2R)-2-(3-Chloro-phenyl)-2-hydroxy-ethylamino]-propyl}-benzo[1,3]dioxole-2,2-dicarboxylic aicd bis-(2,2-dimethyl-pentyl) ester The title compound was prepared from 5-{2-[2-(3-chlorophenyl)-2-hydroxy-ethylamino]-propyl}-benzo[1,3]dioxole-2,2-dicarboxylic acid and 2,2-dimethylpentanol according to the procedure of Example 1 as an off-white solid; $^1$H NMR(DMSO-d$_6$,400 MHz) 0.8 (m, 18H, 6×CH$_3$), 1.1–1.2 (m, 11H, CH$_2$ CH$_3$), 2.6 (m, 1H, CH), 3–3.3 (m, 3H, CH, CH$_2$), 3.4 (brs, 1H, CH), 4.0 (s, 4H, OCH$_2$, OCH$_2$), 5.09 (m, 1H, CH), 6.36 (d, J=4.17 Hz, 1H, OH), 6.86 (dd, J=7.9, 1.32 Hz, 1H, Ar—H), 7.07 (s 1H, Ar—H), 7.09 (d, J=8.35 Hz, Ar—H), 7.35–7.42 (m, 3H, Ar—H), 7.48 (s, 1H, Ar—H), 9.84 (brs, 1H, NH), 9.48 (brs, 1H, NH); IR (KBr, cm$^{-1}$) 3300 (OH), 2900 (NH), 1760 (CO); MS m/e 617 (M$^+$); Analysis for: C$_{34}$H$_{48}$ClNO$_7$×HCl: Calc'd: C, 62.38; H, 7.55; N, 2.14; Found: C, 62.47; H, 7.51; N, 2.31.

EXAMPLE 87

5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-furan-3-ylmethyl) ester The title compound was prepared from 5-{2-[2-(3-chlorophenyl)-2-hydroxy-ethylamino]-propyl}-benzo[1,3]dioxole-2,2-dicarboxylic acid and tetrahydrofuran-3-ylmethanol according to the procedure of Example 1 as an off-white solid; $^1$H NMR (DMSO-d$_6$,400 MHz) δ 1.03 (d, J=6.37 Hz, 3H, CH$_3$), 1.5 (m, 2H, CH$_2$), 1.9 (m, 2H, CH$_2$), 2.6 (m, 3H, CH), 3–3.3 (m, 3H, CH, CH$_2$), 3.4 (brs, 1H, CH), 3.6–3.7 (m, 6H, CH$_2$), 4.1–4.15 (m, 6H, CH$_2$), 5.09 (m, 1H, CH), 6.36 (brs, 1H, OH), 6.86 (m, 1H, Ar—H), 7.07 (m, 2H, Ar—H), 7.38–7.42 (m, 3H, Ar—H), 7.47 (s, 1H, Ar—H), 8.84 (brs, 2H, NH, NH); IR (KBr, cm$^{-1}$) 3300 (OH), 2900 (NH), 1760 (CO); MS m/e 590 (M+H)$^+$; Analysis for: C$_{30}$H$_{36}$ClNO$_9$×HCl: Calc'd: C, 57.51; H, 5.95; N, 2.24; Found: C, 57.80; H, 6.30; N, 2.21.

EXAMPLE 88

5-{(2R)-2-[(2R)-2-(3-Chloro-phenyl)-2-hydroxy-ethylamino]-propyl}-benzo[1,3]dioxole-2,2-dicarboxylic aicd bis-(3-hydroxy-2,2,4-trimethyl-pentyl) ester The title compound was prepared from 5-{2-[2-(3-chlorophenyl)-2-hydroxy-ethylamino]-propyl}-benzo[1,3]dioxole-2,2-dicarboxylic acid and cyclopropylmethanol according to the procedure of Example 1 as an off-white solid; $^1$H NMR (DMSO d$_6$,400 MHz) δ 0.7–0.95 (m, 27H, 9×CH$_3$), 1.8 (m, 1H, CH), 2.1 (m, 1H, CH), 2.6 (m, 1H, CH), 3–3.4 (m, 6H, OH, CH, CH$_2$), 3.6–3.8 (brs, 2H, CH), 4.04 (m, 2H, OCH$_2$, OCH$_2$), 4.6 (m, 1H, CH), 4.85 (m, 1H, CH), 5.05 (m, 1H, CH), 6.35 (d, J=3.7 Hz, 1H, OH), 6.85 (dd, J=7.9, 1.32 Hz, 1H, Ar—H), 7.09 (m, 2H, Ar—H), 7.38–7.42 (m, 3H, Ar—H), 7.5 (s, 1H, Ar—H), 8.78 (brs, 1H, NH), 9.2 (brs, 1H, NH); IR (KBr, cm$^{-1}$) 3400 (OH), 2900 (NH), 1750 (CO); MS m/e 678 (M+H)$^+$; Analysis for: C$_{36}$H$_{52}$ClNO$_9$×HCl: Calc'd: C, 60.50; H, 7.47; N, 1.95; Found: C, 60.30; H, 8.09; N, 1.62.

EXAMPLE 89

5-{(2R)-2-[(2R)-2-(3-Chloro-phenyl)-2-hydroxy-ethylamino]-propyl}-benzo[1,3]dioxole-2,2-dicarboxylic aicd bis-(2,2-dimethyl-3-phenyl-propyl) ester The title compound was prepared from 5-{$^2$-[2-(3-chlorophenyl)-2-hydroxy-ethylamino]-propyl}-benzo[1,3]dioxole-2,2-dicarboxylic acid and 2,2-dimethyl-3-phenylpropanol according to the procedure of Example 1 as an off-white solid; $^1$H NMR (DMSO-d$_6$,400 MHz) δ 0.82 (s, 12H, 4×CH$_3$), 1.08 (d, J=6.37 Hz, 3H, CH$_3$), 2.6 (m, 1H, CH), 3–3.3 (m, 3H, CH, CH$_2$), 3.4 (brs, 1H, CH), 3.96 (s, 4H, OCH$_2$, OCH$_2$), 5.04 (m, 1H, CH), 6.35 (d, J=4.17 Hz, 1H, OH), 6.89 (dd, J=8.13, 1.53 Hz, 1H, Ar—H), 7.05 (m, 4H, Ar—H), 7.14 (m, 8H, Ar—H), 7.38–7.42 (m, 3H, Ar—H), 7.5 (s, 1H, Ar—H), 8.81 (brs, 1H, NH), 9.38 (brs, 1H, NH); IR (KBr, cm$^-$) 3400 (OH), 2900 (NH), 1760 (CO); MS m/e 714 (M+H)$^+$; Analysis for: C$_{42}$H$_{48}$ClNO$_7$×HCl: Calc'd: C, 67.19; H, 6.58; N, 1.87; Found: C, 66.69; H, 6.53; N, 1.83.

EXAMPLE 90

5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-pyran-2-ylmethyl) ester The title compound was prepared from 5-{2-[2-(3-chlorophenyl)-2-hydroxy-ethylamino]-propyl}-benzo[1,3]dioxole-2,2-dicarboxylic acid and tetrahydropyran-2- ylmethanol according to the procedure of Example 1 as an off-white solid; $^1$H NMR (DMSO-$d_6$,400 MHz) δ 1.10 (d, J=6.37 Hz, 3H, $CH_3$), 1.1–1.2 (m, 2H, $CH_2$), 1.3–1.6 (m, 8H, $CH_2$), 1.7–1.8 (m, 2H, CH2), 2.6 (m, 1H, CH), 3–3.5 (m, 9H, CH, $CH_2$), 3.8 (m, 2H, CH), 4.19–4.2 (s, s, 4H, $OCH_2$, $OCH_2$), 5.04 (m, 1H, CH), 6.35 (d, J=4.17 Hz, 1H, OH), 6.85 (d, J=8.13 Hz, 1H, Ar—H), 7.07 (m, 2H, Ar—H), 7.36–7.42 (m, 3H, Ar—H), 7.48 (s, 1H, Ar—H), 8.76 (brs, 1H, NH), 9.18 (brs, 1H, NH); IR (KBr, $cm^{-1}$) 3400 (OH), 2900 (NH), 1760 (CO); MS m/e 618 (M+H)$^+$; Analysis for: $C_{32}H_{40}ClNO_9 \times HCl$: Calc'd: C, 58.72; H, 6.31; N, 2.14; Found: C, 57.97; H, 6.46; N, 2.08.

EXAMPLE 91

5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-furan-2-ylmethyl) ester The title compound was prepared from 5-{2-[2-(3-chloro-phenyl)-2-hydroxy-ethylamino]-propyl}-benzo[1,3]dioxole-2,2-dicarboxylic acid and tetrahydrofuran-2-ylmethanol according to the procedure of Example 1 as an off-white solid; $^1$H NMR (DMSO-$d_6$,400 MHz) δ 1.1 (d, J=6.37 Hz, 3H, $CH_3$), 1.43–1.6 (m, 2H, $CH_2$) 1.65–1.8 (m, 4H, $CH_2$), 1.98–2.0 (m, 2H, $CH_2$), 2.6 (m, 1H, CH), 3–3.3 (m, 3H, CH, $CH_2$), 3.4 (brs, 1H, CH), 3.57–3.7 (m, 4H, $CH_2$), 4.05 (m, 2H, $CH_2$), 4.2 (m, 2H, $CH_2$), 4.3 (m, 2H, $CH_2$), 5.04 (m, 1H, CH), 6.34 (d, J=3.95 Hz, 1H, OH), 6.84 (dd, J=8.13, 1.32 Hz, 1H, Ar—H), 7.07 (m, 2H, Ar—H), 7.36–7.44 (m, 3H, Ar—H), 7.48 (s, 1H, Ar—H), 8.77 (brs, 1H, NH), 9.2 (brs, 1H, NH); IR (KBr, $cm^{-1}$) 3400 (OH), 2900 (NH), 1760 (CO); MS m/e 590 (M+H)$^+$; Analysis for: $C_{30}H_{36}ClNO_9 \times HCl$: Calc'd: C, 57.51; H, 5.95; N, 2.24; Found: C, 56.37; H, 5.90; N, 2.20.

EXAMPLE 92

5-{(2R)-2-[(2R)-2-(3-Chloro-phenyl)-2-hydroxy-ethylamino]-propyl}-benzo[1,3]dioxole-2,2-dicarboxylic aicd bis-(5-methyl-[1,3]dioxan-5-ylmethyl) ester The title compound was prepared from 5-{2-[2-(3-chloro-phenyl)-2-hydroxy-ethylamino]-propyl}-benzo[1,3]dioxole-2,2-dicarboxylic acid and 5-methyl-[1,3]dioxan-5-ylmethanol according to the procedure of Example 1 as an off-white solid; $^1$H NMR (DMSO-$d_6$,400 MHz) 6 0.7 (s, 3H, $CH_3$), 0.74 (s, 3H, $CH_3$), 1.1 (d, J=6.59 Hz, 3H, $CH_3$), 2.6 (m, 1H, CH), 3–3.3 (m, 8H, CH, $CH_2$), 3.6–3.7 (m, 4H, $CH_2$), 4.6–4.8 (m, 4H, $CH_2$), 5.04 (m, 1H, CH), 6.34 (brs, 1H, OH), 6.84 (dd, J=8.13, 1.32 Hz, 1H, Ar—H), 7.07 (m, 2H, Ar—H), 7.36–7.44 (m, 3H, Ar—H), 7.48 (s, 1H, Ar—H), 8.77 (brs, 1H, NH), 9.2 (brs, 1H, NH); IR (KBr, $cm^-$) 3400 (OH), 2900 (NH), 1760 (CO); MS m/e 650 (M+H)+; Analysis for: $C_{32}H_{40}ClNO_{11} \times HCl$: Calc'd: C, 55.98; H, 6.02; N, 2.04; Found: C, 54.67; H, 6.58; N, 2.05.

EXAMPLE 93

5-{(2R)-2-[(2R)-2-(3-Chloro-phenyl)-2-hydroxy-ethylamino]-propyl}-benzo[1,3]dioxole-2,2-dicarboxylic aicd bis-(1-methyl-cyclohex-3-enylmethyl) ester The title compound was prepared from 5-{2-[2-(3-chloro-phenyl)-2-hydroxy-ethylamino]-propyl}-benzo[1,3]dioxole-2,2-dicarboxylic acid and 1-methylcyclohex-3-enylmethanol according to the procedure of Example 1 as an off-white solid; $^1$H NMR (DMSO-$d_6$,400 MHz) δ 0.84 (s, 6H, 2×$CH_3$), 1.09 (d, J=6.4 Hz, 3H, $CH_3$), 1.25–1.4 (m, 4H, $CH_2$), 1.6–1.65 (m, 2H, $CH_2$), 1.8–2.0 (m, 6H, $CH_2$), 2.6 (m, 1H, CH), 3–3.3 (m, 3H, CH, $CH_2$), 3.4 (brs, 1H, CH), 4.04 (m, 4H, $OCH_2$, $OCH_2$), 5.05 (m, 1H, CH), 5.55–5.65 (m, 4H, CH), 6.35 (d, J=4.17 Hz, 1H, OH), 6.85 (dd, J=7.9, 1.32 Hz, 1H, Ar—H), 7.07 (m, 2H, Ar—H), 7.38–7.42 (m, 3H, Ar—H), 7.5 (s, 1H, Ar—H), 8.8 (brs, 1H, NH), 9.4 (brs, 1H, NH); IR (KBr, $cm^{-1}$) 3400 (OH), 2900 (NH), 1760 (CO); MS m/e 638 (M+H)$^+$; Analysis for: $C_{36}H_{44}ClNO_7 \times HCl$: Calc'd: C, 64.09; H, 6.72; N, 2.08; Found: C, 64.69; H, 7.19; N, 1.67.

EXAMPLE 94

5-{(2R)-2-[(2R)-2-(3-Chloro-phenyl)-2-hydroxy-ethylamino]-propyl}-benzo[1,3]dioxole-2,2-dicarboxylic aicd bis-(3-hydroxy-2,2-dimethyl-propyl) ester The title compound was prepared from 5-{2-[2-(3-chloro-phenyl)-2-hydroxy-ethylamino]-propyl}-benzo[1,3]dioxole-2,2-dicarboxylic acid 3-hydroxy-2,2-dimethyl-propanol according to the procedure of Example 1 as an off-white solid; $^1$H NMR (DMSO-$d_6$,400 MHz) δ0.78 (s, 12H, 4×$CH_3$), 1.09 (d, J=6.4 Hz, 3H, $CH_3$), 2.6 (m, 1H, CH), 3–3.3 (m, 7H, CH, $CH_2$), 3.4 (brs, 1H, CH), 4.04 (s, 4H, $OCH_2$, $OCH_2$),4.65 (m, 2H, OH), 5.05 (m, 1H, CH), 6.34 (d, J=4.17 Hz, 1H, OH), 6.85 (dd, J=7.9, 1.53 Hz, 1H, Ar—H), 7.07 (m, 2H, Ar—H), 7.37–7.42 (m, 3H, Ar—H), 7.48 (s, 1H, Ar—H), 8.78 (brs, 1H, NH), 9.2 (brs, 1H, NH); IR (KBr, $cm^{-1}$) 3400 (OH), 2900 (NH), 1760 (CO); MS m/e 594 (M+H)$^+$; Analysis for: $C_{30}H_{40}ClNO_9 \times HCl$: Calc'd: C, 57.14; H, 6.55; N, 2.22; Found: C, 56.44; H, 6.62; N, 2.38.

EXAMPLE 95

5-{(2R)-2-[(2R)-2-(3-Chloro-phenyl)-2-hydroxy-ethylamino]-propyl}-benzo[1,3]dioxole-2,2-dicarboxylic acid (2-ethoxy-ethyl) ester Through a stirred room temperature solution of 8.0 g (0.019 mole) 5-{2-[2-(3-chloro-phenyl-2-hydroxy-ethylamino]-propyl}-benzo[1,3]dioxole-2,2-dicarboxylic acid and 30 mL of 2-ethoxyethanol was bubbled $HCl_{(g)}$ for 5 min. After heating at 100° C. for 12 h, TLC (9/1 $CH_2Cl_2$/MeOH) indicated the formation of both 5-{2-[2-(3-chloro-phenyl)-2-hydroxy-ethylamino]-propyl}-benzo[1,3]dioxole-2,2-dicarboxylic acid bis-(2-ethoxy-ethyl) ester ($R_f$=0.8; 9/1 $CH_2Cl_2$/MeOH) and 5-{(2R)-2-[(2R)-2-(3-chloro-phenyl)-2-hydroxy-ethylamino]-propyl}-benzo[1,3]dioxole-2,2-dicarboxylic acid (2-ethoxy-ethyl) ester ($R_f$=0.2; 9/1 $CH_2Cl_2$/MeOH). After cooling to room temperature, excess 2-ethoxyethanol was removed via Kugelrohr distillation (0.05 mm, oven temperature=95° C.), and the brown residue was chromatographed on silica gel, eluting with 0 to 10% MeOH in $CH_2Cl_2$, to give 1.0 g (0.002 mole, a 10% yield) of the title compound as an off-white solid; $^1$H NMR (300 MHz, DMSO-$d_6$): δ 1.12 (m, J=6.3 Hz, 3H), 2.5 (m, 3H) 3.35 (m, 8H), 5.06 (m, 1H), 6.3 (s, 1H, OH) 6.5 (m, 1H), 6.6 (m, 1H), 6.8 (m, 2H), 7.0 (m, 1H), 7.5 (m, 2H), 8.0 (m, 1H, NH), d 9.2 (m, 1H, COOH); MS (ES) m/z (relative intensity): 494 (M$^+$+H, 100).

EXAMPLE 96

5-{(2R)-2-[(2R)-2-(3-Chloro-phenyl)-2-hydroxy-ethylamino]-propyl}-benzo[1,3]dioxole-2,2-dicarboxylic acid bis-[2-(3-bromo-phenyl)-ethyl] ester hydrochloride salt The title compound was prepared as a brown oil from 5-{2-[2-(3-chloro-phenyl)-2-hydroxy-ethylamino]-propyl}- benzo[1,3]dioxole-2,2-dicarboxylic acid and 2-(3-bromophenyl)ethanol according to the procedure of Example 1; ¹H NMR (300 MHz, CDCl₃): δ 1.12 (m, J=6.3 Hz, 3H), 2.79 (m, 8H), 3.5 (m 2H), 4.18 (s, 1H, OH), 5.56 (m, 1H), 6.8 (m, 3H), 7.0 (m, 4H), 7.33 (m, 4H), 7.5 (m, 4H), 8.5 (m, 1H, NH); MS (ES) m/z (relative intensity): 788 (M⁺+H, 100).

EXAMPLE 97

5-{(2R)-2-[(2R)-2-(3-Chloro-phenyl)-2-hydroxy-ethylamino]-propyl}-benzo[1,3]dioxole-2,2-dicarboxylic acid bis-(2-m-tolyl-ethyl) ester hydrochloride salt The title compound was prepared as a brown oil from 5-{2-[2-(3-chloro-phenyl)-2-hydroxy-ethylamino]-propyl}-benzo[1,3]dioxole-2,2-dicarboxylic acid and 2-(3-methylphenyl)ethanol according to the procedure of Example 1; yield: 81%; ¹H NMR (300 MHz, CDCl₃): δ 1.12 (m, J=6.3 Hz, 3H), 2.27 (s, 6H), 2.79 (m, 7H), 3.19 (m, 1H), 3.48 (m, 2H), 4.29 (m, J=6.6 Hz, 4H), 5.49 (m, 1H,) 6.75 (m, J=8.1 Hz, 1H), 6.83 (m, 1H), 7.05 (m, 8H), 7.20 (m, 1H), 7.27 (m, 1H), 7.43 (s, 1H), 7.5 (m, 2H); MS (ES) m/z (relative intensity): 658 (M⁺+H, 100).

EXAMPLE 98

5-{(2R)-2-[(2R)-2-(3-Chloro-phenyl)-2-hydroxy-ethylamino]-propyl}-benzo[1,3]dioxole-2,2-dicarboxylic acid diallyl ester

Step 1

(R,R)-5-{2-[[2-(3-Chloro-phenyl)-2-hydroxy-ethyl]-(2,2,2-trichloro-ethoxycarbonyl)-amino]-propyl}-benzo[1,3]dioxole-2,2-dicarboxylic acid diethyl ester To a 0° C. solution of 3.0 g (5.83 mmol) (R,R)-5-{2-[2-(3-chloro-phenyl)-2-hydroxy-ethylamino]-propyl}-benzo[1,3]dioxole-2,2-dicarboxylic acid diethyl ester hydrochloride salt and 60 mL CH₂Cl₂ was added 2.54 mL (1.88 g, 14.57 mmol) of i-Pr₂NEt followed by 0.84 mL (1.30 g, 6.12 mmol) of 2,2,2-trichloroethyl chloroformate. After stirring at room temperature for 6 h, the reaction mixture was quenched with 10 mL sat. aq. NaHCO₃, and extracted with 3×100 mL Et₂O. The combined organics were washed with 1×100 1N HCl, 1×100 mL brine, dried over MgSO₄, filtered and evaporated to a yellow oil. Flash chromatography on silica gel, eluting with hexanes/EtOAc (4/1 to 2/1), gives 3.46 g (5.30 mmol, a 91% yield) of the title compound (R_f=0.32; 2/1 hexanes/EtOAc) as an oily, off-white solid; ¹H NMR 300 MHz, CDCl₃): δ 1.20–1.39 (complex m, 9H), 2.60–2.80 (m, 1H), 2.80–2.91 (m, 1H), 3.01–3.19 (m, 1H), 3.23–3.31 (m, 1H), 3.40–3.53 (m, 1H), 4.10–4.23 (m, 1H), 4.30–4.42 (complex m, 4H), 4.70–4.89 (m, 3H), 6.65–6.88 (complex m, 4H), 7.15–7.39 (complex m, 3H); MS (ES) m/z (relative intensity): 654 (M⁺+H, 100).

Step 2

5-{(2R)-2-[[(2R)-2-(tert-Butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid diethyl ester To a −78° C. solution of 3.75 g (5.47 mmol) (R,R)-5-{2-[[2-(3-chloro-phenyl)-2-hydroxy-ethyl]-(2,2,2-trichloro-ethoxycarbonyl)-amino]-propyl}-benzo[1,3]dioxole-2,2-dicarboxylic acid diethyl ester and 60 mL of CH₂Cl₂ was added 1.27 mL (1.17 g, 10.94 mmol) of 2,6-lutidene followed by 1.38 mL (1.59 g, 6.03 mmol) of TBSOTf. After stirring at −78° C. for 1.5 h, the reaction mixture was quenched with 50 mL sat. aq. NaHCO₃ and warmed to room temperature. After extraction with 3×150 mL Et₂O, the combined organics were washed with 1×200 mL sat. CuSO₄, 1×200 mL brine, dried over MgSO₄, filtered and evaporated to a cloudy white oil. Flash chromatography on silica gel, eluting with hexanes/EtOAc (8/1 to 4/1) gave 3.42 g (4.46 mmol, an 82% yield) of the title compound (R_f=0.31; 4/1 hexanes/EtOAc) as a gummy colorless solid; ¹H NMR (300 MHz, CDCl₃): δ−0.13−(−0.08) (m, 3H), 0.00–0.06 (m, 3H), 0.85–0.91 (m, 9H), 1.05 (d, J=6.7 Hz, 3H), 1.33 (t, J=7.1 Hz, 6H), 2.60–2.75 (m, 1H), 2.77–2.96 (m, 1H), 3.00–3.31 (m, 2H), 3.77–4.00 (m, 1H), 4.35 (q, J=7.1 Hz, 4H), 4.65–4.88 (m, 2H), 5.02–5.20 (m, 1H), 6.60–6.85 (m, 4H), 7.15–7.37 (m, 3H); MS (ES) m/z (relative intensity): 790 (M⁺+Na, 100), 768 (M⁺+H, 20).

Step 3

5-{(2R)-2-[[(2R)-2-(tert-Butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid To a room temperature solution of 3.31 g (4.31 mmol) 5-{(2R)-2-[[(2R)-2-(tert-butyl-dimethyl-siloxy)-2-(3-chloro-phenyl)-ethyl]-(2,2,2-tichloro-ethoxycarbonyl)-amino]-propyl}-benzo[1,3]dioxole-2,2-dicarboxylic acid diethyl ester, 100 mL MeOH and 25 mL H₂O was added 4.31 mL (21.56 mmol) of a 5N NaOH solution. After sting at room temperature for 80 h, the solvent was evaporated, and the resulting slurry was acidified to pH 1 with 1 N HCl. The reaction mixture is extracted with 3×100 mL EtOAc, and the combined organics were washed with 2×30 mL brine, dried over Na₂SO₄, filtered and evaporated to give 3.01 g (4.23 mmol, a 98% yield) of the title compound (R_f=0.0; 10/1 CHCl₃/MeOH) as an off-white solid; ¹H NMR (300 MHz, CDCl₃): δ−0.19−(−0.11) (m, 3H), 0.01–0.09 (m, 3H), 0.81–0.91 (m, 9H), 0.93–0.97 (m, 3H), 2.55–2.97 (complex m, 3H), 3.07–3.35 (m, 2H), 3.80–4.40 (br m, 2H), 4.60–4.83 (m, 2H), 5.03–5.18 (m, 1H), 6.60–6.92 (m, 4H), 7.15–7.39 (m, 3H); MS (ES) m/z (relative intensity): 734 (M⁺+Na, 30), 712 (M⁺+H, 100).

Step 4

5-{(2R)-2-[[(2R)-2-(tert-Butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid diallyl ester To a room temperature solution of 950 mg (1.34 mmol) 5-{(2R)-2-[[(2R)-2-(tert-butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid and 15 mL DMF was added 267 mg (2.67 mmol) of KHCO₃ and 0.26 mL (471 mg, 2.80 mmol) of allyl iodide. After stirring at room temperature for 16 h, the reaction was quenched with 10 mL sat. aq. NaHCO₃ and extracted with 3×100 mL Et₂O. The combined organics were washed with 1×150 mL brine, dried over MgSO₄, filtered and evaporated to a colorless oil. Flash chromatography on silica gel, eluting with hexanes/EtOAc (8/1 to 4/1), gave 670 mg (0.85 mmol, a 63% yield) of the title compound (R_f=0.62; 2/1 hexanes/EtOAc) as a colorless oil; ¹H NMR (300 MHz, CDCl₃):

49

δ–0.19–(–0.11) (m, 3H), 0.00–0.08 (m, 3H), 0.87 (s, 9H), 1.04 (d, J=6.7 Hz, 3H), 2.60–2.74 (m, 1H), 2.77–2.98 (m, 1H), 3.03–3.17 (m, 1H), 3.18–3.30 (m, 1H), 3.75–3.98 (m, 1H), 4.65–4.87 (m, 6H), 5.03–5.18 (m, 1H), 5.29 (d, J=17.3 Hz, 2H), 5.34 (d, J=23.7 Hz, 2H), 5.82–5.97 (complex m, 2H), 6.60–6.88 (m, 4H), 7.15–7.37 (m, 3H); MS (ES) m/z (relative intensity): 814 ($M^+$+Na, 100).

Step 5

5{(2R)-2-[[(2R)-2-(3-Chloro-phenyl)-2-hydroxy-ethyl]-(2,2,2-trichloro-ethoxycarbonyl)-amino]-propyl}-benzo[1,3]dioxole-2,2-dicarboxylic acid diallyl ester To a 0° C. solution of 650 mg (0.82 mmol) 5-{(2R)-2-[[(2R)-2-(tert-butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid diallyl ester and 20 mL THF was added 1.0 mL of HF·pyridine, and the reaction mixture was warmed to room temperature. After 22 h, TLC indicated that some starting material remained ($R_f$=0.62 (2/1 hexanes/EtOAc), and an additional 1.0 mL of HF·pyridine was added. After a total of 26 h, TLC indicated the disappearance of starting material and the formation of the title compound ($R_f$=0.28 (2/1 hexanes/EtOAc). The reaction mixture was slowly quenched with 30 mL of sat. aq. $NaHCO_3$, extracted with 2×75 mL $Et_2O$ and then with 1×75 mL EtOAc. The combined organics were washed with 1×100 mL brine, dried over $MgSO_4$, filtered and evaporated to a colorless oil. Flash chromatography on silica gel, eluting with hexanes/EtOAc (2/1), gave 460 mg (0.68 mmol, an 83% yield) of the title compound ($R_f$=0.28; 2/1 hexanes/EtOAc) as a colorless oil; $^1$H NMR (300 MHz, $CDCl_3$): δ 1.20–1.37 (m, 3H), 2.60–2.78 (m, 2H), 2.80–2.91 (m, 1H), 2.98–3.18 (m, 1H), 3.23–3.40 (m, 1H), 3.41–3.54 (m, 2H), 4.10–4.26 (br m, 1H), 4.73–4.92 (5H), 5.22–5.40 (complex m, 4H), 5.81–5.98 (complex m, 2H), 6.62–6.87 (m, 4H), 7.17–7.41 (m, 3H); MS (ES) m/z (relative intensity): 700 ($M^+$+Na, 100).

Step 6

5-{(2R)-2-[(2R)-2-(3-Chloro-phenyl)-2-hydroxy-ethylamino]-propyl}-benzo[1,3]dioxole-2,2-dicarboxylic acid diallyl ester A mixture of 370 mg (0.55 mmol) 5-{(2R)-2-[[(2R)-2-(3-chloro-phenyl)-2-hydroxy-ethyl]-(2,2,2-trichloro-ethoxycarbonyl)-amino]-propyl}-benzo[1,3]dioxole-2,2-dicarboxylic acid diallyl ester, 10 mL glacial acetic acid and 357 mg (5.46 mmol) of Zn dust were stirred at room temperature for 40 h. The reaction mixture was filtered through celite, poured into 50 mL brine, and extracted with 3×50 mL EtOAc. The combined organics were washed with 3×75 mL sat. $NaHCO_3$, 1×75 mL brine, dried over $Na_2SO_4$, filtered and evaporated to a colorless oil. Flash chromatography on silica gel, eluting with $CHCl_3$/MeOH (20/1 to 10/1), gave 180 mg (0.36 mmol, a 66% yield) of the title compound ($R_f$=0.35; 10/1 $CHCl_3$/MeOH) as a colorless gum; $^1$H NMR (300 MHz, $CDCl_3$): δ 1.20–1.33 (m, 3H), 2.70–2.81 (m, 1H), 3.00–3.19 (m, 2H), 3.36–3.45 (m, 2H), 4.50–5.50 (br s, 2H), 4.70–4.80 (m, 4H), 5.10–5.20 (m, 1H), 5.25–5.40 (m, 4H), 5.82–6.00 (complex m, 2H), 6.70–6.91 (m, 3H), 7.17–7.30 (m, 3H), 7.41 (s, 1H); MS (ES) m/z (relative intensity): 502 ($M^+$, 100).

50

EXAMPLE 99

5-{(2R)-2-[(2R)-2-(3-Chloro-phenyl)-2-hydroxy-ethylamino]-propyl}-benzo[1,3]dioxole-2,2-dicarboxylic acid bis-(3-phenyl-allyl)ester Step 1

5-{(2R)-2-[[(2R)-2-(tert-Butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid bis-(3-phenyl-allyl) ester The title compound was prepared as a colorless oil according to the procedure of Example 4, Step 4 except that cinnamyl bromide was used in place of allyl iodide; yield 66%; $R_f$=0.68 (2/1 hexanes/EtOAc); $^1$H NMR (300 MHz, $CDCl_3$): δ–0.19–(–0.11) (m, 3H), –0.01–0.05 (m, 3H), 0.83–0.90 (m, 9H), 1.02 (d, J=6.7 Hz, 3H), 2.60–2.75 (m, 1H), 2.77–2.96 (m, 1H), 3.04–3.33 (m, 2H), 3.76–4.00 (m, 1H), 4.65–4.85 (m, 2H), 4.90–4.98 (m, 4H), 5.02–5.20 (m, 1H), 6.20–6.33 (m, 2H), 6.60–6.85 (m, 5H), 7.15–7.45 (m, 14H); MS (ES) m/z(relative intensity) 944 ($M^+$, 100).

Step 2

5-{(2R)-2-[[(2R)2-(3-Chloro-phenyl)-2-hydroxy-ethyl]-(2,2,2-trichloro-ethoxycarbonyl)-amino]-propyl}-benzo[1,3]dioxole-2,2-dicarboxylic acid bis-(3-phenyl-allyl) ester The title compound was prepared as a colorless oil according to the procedure of Example 4, Step 5 except that 5-{(2R)-2-[[(2R)-2-(tert-butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid bis-(3-phenyl-allyl) ester was used in place of 5-{(2R)-2-[[(2R)-2-(tert-butyl-dimethyl-siloxy)-2-(3-chloro-phenyl)-ethyl]-(2,2,2-trichloro-ethoxycarbonyl)-amino]-propyl}-benzo[1,3]dioxole-2,2-dicarboxylic acid diallyl ester; yield 78%; $R_f$=0.31 (2/1 hexanes/EtOAc); $^1$H NMR (300 MHz, $CDCl_3$): δ 1.20–1.35 (m, 3H), 2.58–2.80 (m, 1H), 2.81–3.20 (m, 2H), 3.22–3.56 (m, 2H), 4.10–4.31 (m, 3H), 4.70–4.95 (m, 5H), 6.17–6.43 (m, 2H), 6.60–6.90 (m, 5H), 7.15–7.45 (m, 14H).; MS (ES) m/z (relative intensity): 830 ($M^+$+H, 100).

Step 3

5-{(2R)-2-[(2R)-2-(3-Chloro-phenyl)-2-hydroxy-ethylamino]-propyl}-benzo[1,3]dioxole-2,2-dicarboxylic acid bis-(3-phenyl-allyl)ester The fide compound was prepared as a colorless oil according to the procedure of Example 4, Step 6 except that 5-{($^2$R)-2-[[(2R)2-(3-chloro-phenyl)-2-hydroxy-ethyl]-(2,2,2-trichloro-ethoxycarbonyl)-amino]-propyl}-benzo[1,3]dioxole-2,2-dicarboxylic acid bis-(3-phenyl-allyl) ester was used in place of 5-{(2R)-2-[[(2R)-2-(3-chloro-phenyl)-2-hydroxy-ethyl]-(2,2,2-trichloro-ethoxycarbonyl)-amino]-propyl}-benzo[1,3]dioxole-2,2-dicarboxylic acid diallyl ester; yield 59%; $R_f$=0.35 (10/1 $CHCl_3$/MeOH); $^1$H NMR (300 MHz, $CDCl_3$): δ 1.15 (d, J=6.3 Hz, 3H), 2.50–3.70 (brs, 2H), 2.60–2.71 (m, 1H), 2.80–2.92 (m, 2H), 2.95–3.15 (m, 2H), 4.83–4.95 (m, 5H), 5.25–5.40 (m, 4H), 6.08–6.30 (complex m, 2H), 6.66–6.91 (m, 5H), 7.15–7.40 (m, 14H); MS (ES) m/z (relative intensity): 654 ($M^+$, 100).

EXAMPLE 100

5-{(2R)-2-[(2R)-2-(3-Chloro-phenyl)-2-hydroxy-ethylamino]-propyl}-benzo[1,3]dioxole-2,2-dicarboxylic acid dicyclooctyl ester The title compound was prepared as a white gum from 5-{2-[2-(3-chloro-phenyl)-2-hydroxy-ethylamino]-propyl}- benzo[1,3]dioxole-2,2-dicarboxylic acid and cyclooctanol according to the procedure of Example 1; yield 84%; $R_f$=0.30 (10/1 CHCl$_3$/MeOH); 1H NMR (300 MHz, CDCl$_3$): δ 1.30–1.39 (brd, 3H), 1.40–1.92 (m, 28H), 2.72–2.87 (m, 1H), 3.06–3.30 (m, 2H), 3.39–3.52 (m, 2H), 3.80–3.91 (m, 1H), 5.02–5.13 (m, 1H), 5.40–5.80 (m, 1H), 6.71–6.89 (m, 4H), 7.21–7.37 (m, 2H), 7.44 (s, 1H), 8.73 (brs, 1H), 10.11 (brs, 1H); MS (ES) m/z (relative intensity): 679 (M$^+$, 100).

EXAMPLE 101

5-{(2R)-2-[(2R)-2-(3-Chloro-phenyl)-2-hydroxy-ethylamino]-propyl}-benzo[1,3]dioxole-2,2-dicarboxylic acid bis-(4-benzyloxy-but-2-enyl)ester To a room temperature solution of 110 mg (0.25 mmol) of 5-{2-[2-(3-chloro-phenyl)-3-oxazolidinyl]-propyl}-benzo[1,3]dioxole-2,2-dicarboxylic acid and 5 mL of DMF was added 69 mg (0.69 mmol) of K$_2$CO$_3$ followed by 195 mg (0.76 mmol) of cis-4-benzyloxy-2-buten-1-methane sulfonate. After heating at 50° C. for 20 h, the reaction mixture was cooled to room temperature, poured into 50 mL of brine and extracted with 2×50 mL EtOAc. The combined organics were washed with 1×50 mL sat. aq. NaHCO$_3$, 1×50 mL brine, dried over Na$_2$SO$_4$, filtered and evaporated to a yellow oil. Flash chromatography on silica gel, eluting with CHCl$_3$/MeOH (40/1 to 10/1), gave 89 mg (0.12 mmol, a 47% yield) of the title compound ($R_f$=0.30 (10/1 CHCl$_3$/MeOH) as a yellow oil. $^1$H NMR (300 MHz, CDCl$_3$): δ 0.98–1.10 (m, 3H), 2.44–2.78 (m, 3H), 2.82–3.00 (m, 2H), 4.11–4.20 (m, 4H), 4.40–4.70 (m, 2H), 4.85–4.95 (m,, 4H), 5.70–5.79 (m, 2H), 5.81–5.92 (m, 2H), 6.72–6.90 (m, 3H), 7.17–7.47 (m, 14H); MS (ES) m/z (relative intensity): 742 (M$^+$, 100).

EXAMPLE 102

5-{(2R)-2-[(2R)-2-(3-Chloro-phenyl)-2-hydroxy-ethylamino]-propyl}benzo[1,3]dioxole-2,2-dicarboxylic acid phenethyl ester To a 0° C. solution of 0.630 g (1.0 mmol) of 5-{(2R)-2-[(2R)-2-(3-chloro-phenyl)-2-hydroxy-ethylamino]-propyl}-benzo[1,3]dioxole-2,2-dicarboxylic acid bis-(2-phenethyl) ester in 12 mL CH$_3$CN was added 5.6 mL 1 N NaOH (5.6 mmol), and the resulting solution was stirred at room temperature for 12 h. The solution was concentrated, 10 mL of water and 10 mL of ether were added, the pH of the mixture was adjusted to pH 8 with sat. aq. NH$_4$Cl, and the resulting white precipitate was collected by filtration. After washing with sat. aq. NaHCO$_3$, water and ether, the resulting solid was dried under vacuum to give 0.4 g (0.76 mmol, a 76% yield) of the title compound ($R_f$=0.39; 9/1 CHCl$_3$/MeOH) as a tan solid ; mp 75–82° C.; $^1$H NMR (300 MHz, DMSO-d$_6$): δ 1.00 (d, 3H), δ 2.5 (br m, 4H), δ 2.84–3.10 (m, 5H), δ 3.35 (br, water), δ 4.28 (t, 2H), δ 4.90 (m, 1H), δ 6.6 (d, 1H), δ 6.76 (d, 2H), δ 7.21 (br s, 6H), δ 7.36 (m, 3H), δ 7.46 (s, 1H); MS (ES) m/z (relative intensity): 526 (M$^+$, 100).

EXAMPLE 103

5-{(2R)-2-[(2R)-2-(3-Chloro-phenyl)-2-hydroxy-ethylamino]-propyl}benzo[1,3]dioxole-2,2-dicarboxylic acid (1-phenyl-ethyl) ester The title compound was prepared as a tan solid according to the procedure of Example 102 from 5-{(2R)-2-[(2R)-2-(3-chloro-phenyl)-2-hydroxy-ethylamino]-propyl}benzo[1,3]dioxole-2,2-dicarboxylic acid bis-(1-phenylethyl) ester; yield: 22%; $R_f$=0.39 (9/1 CHCl$_3$/MeOH; mp 71–79° C.; $^1$H NMR (300 MHz, DMSO-d$_6$): δ 1.00 (d, 3H), δ 1.5 (br m, 3H), δ 2.4–2.75 (m, 1H), δ 3.15–3.45(br m, 5H), δ 4.90 (br d, 1H), δ 5.20 (br d, 1H), δ 5.90 (q, 1H), δ 6.6 (d, 1H), δ 6.76 (d, 2H), δ 7.21 (br s, 6H), δ 7.36 (m, 3H), δ 7.46 (s, 1H); MS (ES) m/z (relative intensity): 526 (M$^+$, 100).

EXAMPLE 104

5-{(2R)-2-[(2R)-2-(3-Chloro-phenyl)-2-hydroxy-ethylamino]-propyl}benzo[1,3]dioxole-2,2-dicarboxylic acid bis-(3-benzyloxy-propyl)ester The title compound was prepared as a yellow gum from 5-{2-[2-(3-chloro-phenyl)-2-hydroxy-ethylamino]-propyl}-benzo[1,3]dioxole-2,2-dicarboxylic acid and 3-benzyloxy-propanol according to the procedure of Example 1; yield: 38%; $R_f$=0.52 (9/1 CHCl$_3$/MeOH); $^1$H NMR (300 MHz, CDCl$_3$): δ 1.32 (d, 3H), δ 2.00 (m, 4H), δ 2.75 (m, 1H), δ 3.30 (s, 2H), δ 3.50 (m, 4H), δ 4.40 (br m, 12H), δ 5.49 (s, 1H), δ 6.68–6.85 (m, 3H), δ 7.24–7.40 (m, 13H), δ 7.43 (s, 1H); MS (ES) m/z (relative intensity): 518 (M$^+$-HCl, 100).

What is claimed is:

1. A compound of the formula:

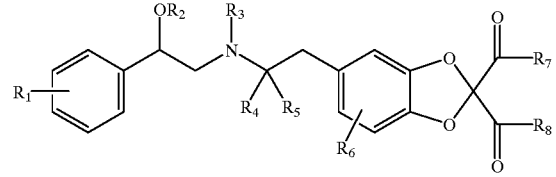

wherein:

$R_1$ and $R_6$ are independently hydrogen, $C_1$ to $C_6$ alkyl, trifluoromethyl, cyano, $C_1$ to $C_6$ alkoxy, or halogen;

$R_2$ is hydrogen or $C_1$ to $C_6$ trialkylsilyl;

$R_3$ is hydrogen or $C_1$ to $C_6$ alkoxycarbonyl;

or $R_2$ and $R_3$ are joined to form a ring:

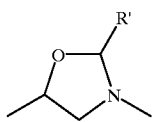

wherein R' is hydrogen, $C_1$ to $C_6$ alkyl, or aryl;

$R_4$ and $R_5$ are independently hydrogen or $C_1$ to $C_6$ alkyl;

$R_7$ and $R_8$ are independently OR$_9$;

$R_9$ in each instance is independently selected from H, $C_1$ to $C_{12}$ cycloalkyl, $C_1$ to $C_{12}$ silylalkyl, aryl, arylalkyl, heteroaryl, alkoxyalkyl, —CHR$_{12}$COOR$_{13}$, —CHR$_{12}$C(O)R$_{13}$, —CHR$_{12}$CONR$_{10}$R$_{11}$, —CHR$_{12}$OCOOR$_{13}$, or —CHR$_{12}$OC(O)R$_{13}$, with the provision that R$_9$ is not hydrogen in both R$_7$ and R$_8$;

$R_{12}$ and $R_{13}$ are independently hydrogen, $C_1$ to $C_{12}$ alkyl, aryl, or aralkyl; or a pharmaceutically acceptable salt thereof, enantiomer thereof, racemic mixture thereof, or diastereomeric mixture thereof.

2. A compound of claim 1 which is 5-{2-[2-(3-chloro-phenyl)-2-hydroxy-ethylamino]-propyl}-benzo[1,3]dioxole-2,2-dicarboxylic acid bis-(2-methoxy-ethyl) ester or a pharmaceutically acceptable salt thereof.

3. A compound of claim 1 which is 5-{2-[2-(3-chloro-phenyl)-2-hydroxy-ethylamino]-propyl}-benzo[1,3]

dioxole-2,2-dicarboxylic acid diphenethyl ester or a pharmaceutically acceptable salt thereof.

4. A compound of claim 1 which is 5-{2-[2-(3-chloro-phenyl)-2-hydroxy-ethylamino]-propyl}-benzo[1,3]dioxole-2,2-dicarboxylic acid bis-(2-butoxy-ethyl) ester or a pharmaceutically acceptable salt thereof.

5. A compound of claim 1 which is 5-{2-[2-(3-chloro-phenyl)-2-hydroxy-ethylamino]-propyl}-benzo[1,3]dioxole-2,2-dicarboxylic acid bis-(2-phenoxy-ethyl) ester or a pharmaceutically acceptable salt thereof.

6. A compound of claim 1 which is 5-{2-[2-(3-chloro-phenyl)-2-hydroxy-ethylamino]-propyl}-benzo[1,3]dioxole-2,2-dicarboxylic acid bis-(2-ethoxy-ethyl) ester or a pharmaceutically acceptable salt thereof.

7. A compound of claim 1 which is 5-{2-[2-(3-chloro-phenyl)-2-hydroxy-ethylamino]-propyl}-benzo[1,3]dioxole-2,2-dicarboxylic acid bis-(2-tert-butoxy-ethyl) ester or a pharmaceutically acceptable salt thereof.

8. A compound of claim 1 which is 5-{2-[2-(3-chloro-phenyl)-2-hydroxy-ethylamino]-propyl}-benzo[1,3]dioxole-2,2-dicarboxylic acid (2-tert-butoxy-ethyl) ester or a pharmaceutically acceptable salt thereof.

9. A compound of claim 1 which is 5-{2-[2-(3-chloro-phenyl)-2-hydroxy-ethylamino]-propyl}-benzo[1,3]dioxole-2,2-dicarboxylic acid bis-(2-isobutoxy-ethyl) ester or a pharmaceutically acceptable salt thereof.

10. A compound of claim 1 which is 5-{2-[2-(3-chloro-phenyl)-2-hydroxy-ethylamino]-propyl}-benzo[1,3]dioxole-2,2-dicarboxylic acid bis-(benzyl) ester or a pharmaceutically acceptable salt thereof.

11. A compound of claim 1 which is 5-{2-[2-(3-chloro-phenyl)-2-hydroxy-ethylamino]-propyl}-benzo[1,3]dioxole-2,2-dicarboxylic acid bis-(cyclohexyl) ester or a pharmaceutically acceptable salt thereof.

12. A compound of claim 1 which is 5-{2-[2-(3-chloro-phenyl)-2-hydroxy-ethylamino]-propyl}-benzo[1,3]dioxole-2,2-dicarboxylic acid bis-(cyclopentyl) ester or a pharmaceutically acceptable salt thereof.

13. A compound of claim 1 which is 5-{2-[2-(3-chloro-phenyl)-2-hydroxy-ethylamino]-propyl}-benzo[1,3]dioxole-2,2-dicarboxylic acid bis-(1-phenyl-ethyl) ester or a pharmaceutically acceptable salt thereof.

14. A compound of claim 1 which is 5-{2-[2-(3-chloro-phenyl)-2-hydroxy-ethylamino]-propyl}-benzo[1,3]dioxole-2,2-dicarboxylic acid bis-(2-isopropoxy-ethyl) ester or a pharmaceutically acceptable salt thereof.

15. A compound of claim 1 which is 5-{2-[2-(3-chloro-phenyl)-2-hydroxy-ethylamino]-propyl}-benzo[1,3]dioxole-2,2-dicarboxylic acid bis-methoxycarbonylmethyl ester or a pharmaceutically acceptable salt thereof.

16. A compound of claim 1 which is 5-{2-[2-(3-chloro-phenyl)-2-hydroxy-ethylamino]-propyl}-benzo[1,3]dioxole-2,2-dicarboxylic acid bis-propoxycarbonylmethyl ester or a pharmaceutically acceptable salt thereof.

17. A compound of claim 1 which is 5-{2-[2-(3-chloro-phenyl)-2-hydroxy-ethylamino]-propyl}-benzo[1,3]dioxole-2,2-dicarboxylic acid bis-(1-methoxycarbonyl-ethyl) ester or a pharmaceutically acceptable salt thereof.

18. A compound of claim 1 which is 5-{2-[2-(3-chloro-phenyl)-2-hydroxy-ethylamino]-propyl}-benzo[1,3]dioxole-2,2-dicarboxylic acid bis-isopropoxycarbonyl-methyl ester or a pharmaceutically acceptable salt thereof.

19. A compound of claim 1 which is 5-{2-[2-(3-chloro-phenyl)-2-hydroxy-ethylamino]-propyl}-benzo[1,3]dioxole-2,2-dicarboxylic acid bis-ethoxycarbonylmethyl ester or a pharmaceutically acceptable salt thereof.

20. A compound of claim 1 which is 5-{2-[2-(3-chloro-phenyl)-2-hydroxy-ethylamino]-propyl}-benzo[1,3]dioxole-2,2-dicarboxylic acid bis-(1-ethoxycarbonyl-ethyl) ester or a pharmaceutically acceptable salt thereof.

21. A compound of claim 1 which is 5-{2-[2-(3-chloro-phenyl)-2-hydroxy-ethylamino]-propyl}-benzo[1,3]dioxole-2,2-dicarboxylic acid bis-trimethylsilanylmethyl ester or a pharmaceutically acceptable salt thereof.

22. A compound of claim 1 which is 5-{2-[2-(3-chloro-phenyl)-2-hydroxy-ethylamino]-propyl}-benzo[1,3]dioxole-2,2-dicarboxylic acid bis-(2-trimethylsilanyl-ethyl) ester or a pharmaceutically acceptable salt thereof.

23. A compound of claim 1 which is 5-{2-[2-(3-chloro-phenyl)-2-hydroxy-ethylamino]-propyl}-benzo[1,3]dioxole-2,2-dicarboxylic acid bis-(3-trimethylsilanyl-propyl) ester or a pharmaceutically acceptable salt thereof.

24. A compound of claim 1 which is 5-{2-[2-(3-chloro-phenyl)-2-hydroxy-ethylamino]-propyl}-benzo[1,3]dioxole-2,2-dicarboxylic acid bis-cyclohexylmethyl ester or a pharmaceutically acceptable salt thereof.

25. A compound of claim 1 which is 5-{2-[2-(3-chloro-phenyl)-2-hydroxy-ethylamino]-propyl}-benzo[1,3]dioxole-2,2-dicarboxylic acid bis-(2-cyclohexyl-ethyl) ester or a pharmaceutically acceptable salt thereof.

26. A compound of claim 1 which is 5-{2-[2-(3-chloro-phenyl)-2-hydroxy-ethylamino]-propyl}-benzo[1,3]dioxole-2,2-dicarboxylic acid bis-(3-cyclopentyl-propyl) ester or a pharmaceutically acceptable salt thereof.

27. A compound of claim 1 which is 5-{2-[2-(3-chloro-phenyl)-2-hydroxy-ethylamino]-propyl}-benzo[1,3]dioxole-2,2-dicarboxylic acid bis-cyclopropylmethyl ester or a pharmaceutically acceptable salt thereof.

28. A compound of claim 1 which is 5-{2-[2-(3-chloro-phenyl)-2-hydroxy-ethylamino]-propyl}-benzo[1,3]dioxole-2,2-dicarboxylic acid bis-(1-methyl-cyclopropyl-methyl) ester or a pharmaceutically acceptable salt thereof.

29. A compound of claim 1 which is 5-{2-[2-(3-chloro-phenyl)-2-hydroxy-ethylamino]-propyl}-benzo[1,3]dioxole-2,2-dicarboxylic acid bis-cyclobutylmethyl ester or a pharmaceutically acceptable salt thereof.

30. A compound of claim 1 which is 5-{2-[2-(3-chloro-phenyl)-2-hydroxy-ethylamino]-propyl}-benzo[1,3]dioxole-2,2-dicarboxylic acid bis-(2-cyclopentyl-ethyl) ester or a pharmaceutically acceptable salt thereof.

31. A compound of claim 1 which is 5-{2-[2-(3-chloro-phenyl)-2-hydroxy-ethylamino]propyl}benzo[1,3]dioxole-2,2-dicarboxylic acid bis-acetoxymethyl ester or a pharmaceutically acceptable salt thereof.

32. A compound of claim 1 which is 5-{2-[2-(3-chloro-phenyl)-2-hydroxy-ethylamino]propyl}benzo[1,3]dioxole-2,2-dicarboxylic acid bis-propionyloxymethyl ester or a pharmaceutically acceptable salt thereof.

33. A compound of claim 1 which is 5-{2-[2-(3-chloro-phenyl)-2-hydroxy-ethylamino]propyl}benzo[1,3]dioxole-2,2-dicarboxylic acid bis-butyryloxymethyl ester or a pharmaceutically acceptable salt thereof.

34. A compound of claim 1 which is 5-{2-[2-(3-chloro-phenyl)-2-hydroxy-ethylamino]propyl}benzo[1,3]dioxole-2,2-dicarboxylic acid bis-isobutyryloxymethyl ester or a pharmaceutically acceptable salt thereof.

35. A compound of claim 1 which is 5-{2-[2-(3-chloro-phenyl)-2-hydroxy-ethylamino]propyl}benzo[1,3]dioxole-2,2-dicarboxylic acid bis-heptanoyloxymethyl ester or a pharmaceutically acceptable salt thereof.

36. A compound of claim 1 which is 5-{2-[2-(3-chloro-phenyl)-2-hydroxy-ethylamino]propyl}benzo[1,3]dioxole-2,2-dicarboxylic acid bis-(4-methyl-pentanoyloxy-methyl) ester or a pharmaceutically acceptable salt thereof.

37. A compound of claim 1 which is 5-{2-[2-(3-chloro-phenyl)-2-hydroxy-ethylamino]propyl benzo[1,3]dioxole-2, 2-dicarboxylic acid bis-hexanoyloxymethyl ester or a pharmaceutically acceptable salt thereof.

38. A compound of claim 1 which is 5-{2-[2-(3-chloro-phenyl)-2-hydroxy-ethylamino]propyl}benzo[1,3]dioxole-2,2-dicarboxylic acid bis-(2,2-dimethyl-propionyloxymethyl) ester or a pharmaceutically acceptable salt thereof.

39. A compound of claim 1 which is 5-{2-[2-(3-chloro-phenyl)-2-hydroxy-ethylamino]propyl}benzo[1,3]dioxole-2,2-dicarboxylic acid bis cyclohexanecarbonyloxymethyl ester or a pharmaceutically acceptable salt thereof.

40. A compound of claim 1 which is 5-{2-[2-(3-chloro-phenyl)-2-hydroxy-ethylamino]propyl}benzo[1,3]dioxole-2,2-dicarboxylic acid bis-(1-propionyloxy-ethyl) ester or a pharmaceutically acceptable salt thereof.

41. A compound of claim 1 which is 5-{2-[2-(3-chloro-phenyl)-2-hydroxy-ethylamino]propyl}benzo[1,3]dioxole-2,2-dicarboxylic acid bis-[1-(2,2-dimethyl-propionyloxyethyl) ester or a pharmaceutically acceptable salt thereof.

42. A compound of claim 1 which is 5-{2-[2-(3-chloro-phenyl)-2-hydroxy-ethylamino]propyl}benzo[1,3]dioxole-2,2-dicarboxylic acid bis-(3,3-dimethyl-butyryloxymethyl) ester or a pharmaceutically acceptable salt thereof.

43. A compound of claim 1 which is 5-{2-[2-(3-chloro-phenyl)-2-hydroxy-ethylamino]propyl}benzo[1,3]dioxole-2,2-dicarboxylic acid bis-[1-(3,3-dimethyl-butyryl-oxy)ethyl)}ester or a pharmaceutically acceptable salt thereof.

44. A compound of claim 1 which is 5-{2-[2-(3-chloro-phenyl)-2-hydroxy-ethylamino]propyl}benzo[1,3]dioxole-2,2-dicarboxylic acid bis-(3-cyclopentyl-propionyl-oxymethyl) ester or a pharmaceutically acceptable salt thereof.

45. A compound of claim 1 which is 5-{2-[2-(3-chloro-phenyl)-2-hydroxy-ethylamino]propyl}benzo[1,3]dioxole-2,2-dicarboxylic acid bis-benzoyloxymethyl ester or a pharmaceutically acceptable salt thereof.

46. A compound of claim 1 which is 5-{2-[2-(3-chloro-phenyl)-2-hydroxy-ethylamino]propyl}benzo[1,3]dioxole-2,2-dicarboxylic acid bis-(benzoyloxy-ethyl) ester or a pharmaceutically acceptable salt thereof.

47. A compound of claim 1 which is 5-{2-[2-(3-chloro-phenyl)-2-hydroxy-ethylamino]propyl}benzo[1,3]dioxole-2,2-dicarboxylic acid bis-(2,2-dimethyl-butyryloxy-methyl) ester or a pharmaceutically acceptable salt thereof.

48. A compound of claim 1 which is 5-((2R)-2-{tert-Butoxycarbonyl-[(2R)-2-(3-chloro-phenyl)-2-hydroxy-ethyl]-amino}-propyl)-benzo[1,3]dioxole-2,2-dicarboxylic acid bis-diethylcarbamoylmethyl ester or a pharmaceutically acceptable salt thereof.

49. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-diethylcarbamoylmethyl ester or a pharmaceutically acceptable salt thereof.

50. A compound of claim 1 which is 5-{2-[2-(3-Chloro-phenyl)-2-hydroxy-ethylamino]-propyl}-benzo[1,3]dioxole-2,2-dicarboxylic acid cyclopropylmethyl ester or a pharmaceutically acceptable salt thereof.

51. A compound of claim 1 which is 5-{2-[2-(3-Chloro-phenyl)-2-hydroxy-ethylamino]-propyl}-benzo[1,3]dioxole-2,2-dicarboxylic acid cyclobutylmethyl ester or a pharmaceutically acceptable salt thereof.

52. A compound of claim 1 which is 5-{2-[2-(3-Chloro-phenyl)-2-hydroxy-ethylamino]-propyl}-benzo[1,3]dioxole-2,2-dicarboxylic acid bis 2-(3-Thienyl)ethyl-ester or a pharmaceutically acceptable salt thereof.

53. A compound of claim 1 which is 5-{2-[2-(3-Chloro-phenyl)-2-hydroxy-ethylamino]-propyl}-benzo[1,3]dioxole-2,2-dicarboxylic acid 2-(3-Thienyl)ethyl ester or a pharmaceutically acceptable salt thereof.

54. A compound of claim 1 which is 5-{2-[2-(3-Chloro-phenyl)-2-hydroxy-ethylamino]-propyl}-benzo[1,3]dioxole-2,2-dicarboxylic acid bis 2-(Chloro)ethyl ester or a pharmaceutically acceptable salt thereof.

55. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-adamantan-1-ylmethyl ester or a pharmaceutically acceptable salt thereof.

56. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid adamantan-1-ylmethyl ester or a pharmaceutically acceptable salt thereof.

57. A compound of claim 1 which is) A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(1-methyl-cyclohexylmethyl) ester or a pharmaceutically acceptable salt thereof.

58. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(2-cyclohexyl-2-methyl-propyl) ester or a pharmaceutically acceptable salt thereof.

59. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(2-methyl-2-nitro-propyl) ester or a pharmaceutically acceptable salt thereof.

60. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-furan-3-ylmethyl) ester or a pharmaceutically acceptable salt thereof.

61. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(3-hydroxy-2,2,4-trimethyl-pentyl) ester or a pharmaceutically acceptable salt thereof.

62. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(2,2-dimethyl-3-phenyl-propyl) ester or a pharmaceutically acceptable salt thereof.

63. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-pyran-2-ylmethyl) ester or a pharmaceutically acceptable salt thereof.

64. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(tetrahydro-furan-2-ylmethyl) ester or a pharmaceutically acceptable salt thereof.

65. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(5-methyl-[1,3]dioxan-5-ylmethyl) ester or a pharmaceutically acceptable salt thereof.

66. A compound of claim 1 which is 5-{(2R)-2-[(2R)-2-(3-Chloro-phenyl)-2-hydroxy-ethylamino]-propyl}-benzo[1,3]dioxole-2,2-dicarboxylic aicd bis-(1-methyl-cyclohex-3-enylmethyl) ester or a pharmaceutically acceptable salt thereof.

67. A compound of claim 1 which is 5-{(2R)-2-[(2R)-2-(3-Chloro-phenyl)-2-hydroxy-ethylamino]-propyl}-benzo

[1,3]dioxole-2,2-dicarboxylic aicd bis-(3-hydroxy-2,2-dimethyl-propyl) ester or a pharmaceutically acceptable salt thereof.

68. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid (2-ethoxy-ethyl) ester or a pharmaceutically acceptable salt thereof.

69. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-[2-(3-bromo-phenyl)-ethyl]ester hydrochloride salt.

70. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-(2-m-tolyl-ethyl) ester hydrochloride salt.

71. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid diallyl ester or a pharmaceutically acceptable salt thereof.

72. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-(3-phenyl-allyl)ester or a pharmaceutically acceptable salt thereof.

73. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid dicyclooctyl ester or a pharmaceutically acceptable salt thereof.

74. A compound of claim 1 which is 5-{(2R)-2-[(2R)-2-(3-Chloro-phenyl)-2-hydroxy-ethylamino]-propyl}-benzo[1,3]dioxole-2,2-dicarboxylic acid bis-(4-benzyloxy-but-2-enyl)ester or a pharmaceutically acceptable salt thereof.

75. A compound of claim 1 which is 5-{(2R)-2-[(2R)-2-(3-Chloro-phenyl)-2-hydroxy-ethylamino]-propyl}benzo[1,3]dioxole-2,2-dicarboxylic acid phenethyl ester or a pharmaceutically acceptable salt thereof.

76. A compound of claim 1 which is 5-{(2R)-2-[(2R)-2-(3-Chloro-phenyl)-2-hydroxy-ethylamino]-propyl}benzo[1,3]dioxole-2,2-dicarboxylic acid (1-phenyl-ethyl) ester or a pharmaceutically acceptable salt thereof.

77. A compound of claim 1 which is 5-{(2R)-2-[(2R)-2-(3-Chloro-phenyl)-2-hydroxy-ethylamino]-propyl}benzo[1,3]dioxole-2,2-dicarboxylic acid bis-(3-benzyloxy-propyl) ester or a pharmaceutically acceptable salt thereof.

78. A compound of the formula:

wherein:
$R_1$ and $R_6$ are independently hydrogen, $C_1$ to $C_6$ alkyl, trifluoromethyl, cyano, $C_1$ to $C_6$ alkoxy, or halogen;
R' is hydrogen, $C_1$ to $C_6$ alkyl, or aryl;
$R_4$ and $R_5$ are independently hydrogen or $C_1$ to $C_6$ alkyl;
$R_7$ and $R_8$ are independently $OR_9$ or $NR_{10}R_{11}$;
$R_9$ is hydrogen, $C_1$ to $C_{12}$ alkyl, $C_1$ to $C_{12}$ cycloalkyl, $C_1$ to $C_{12}$ silylalkyl, aryl, arylalkyl, alkoxyalkyl, heteroaryl, $-CHR_{12}COOR_{13}$, $-CHR_{12}C(O)R_{13}$, $-CHR_{12}CONR_{10}R_{11}$, $-CHR_{12}OCOOR_{13}$, or $-CHR_{12}OC(O)R_{13}$, with the provision that $R_9$ is not hydrogen in both $R_7$ and $R_8$;
$R_{10}$ and $R_{11}$ are independently hydrogen, $C_1$ to $C_{12}$ alkyl, aralkyl, aryl, furanylalkyl, or alkoxycarbonylalkyl;
$R_{12}$ and $R_{13}$ are independently hydrogen, $C_1$ to $C_{12}$ alkyl, aryl, or aralkyl; or a pharmaceutically acceptable salt thereof, enantiomer thereof, racemic mixture thereof, or diastereomeric mixture thereof.

79. A compound of claim 78 which is 5-{2-[2-(3-chloro-phenyl)-3-oxazolidinyl]-propyl}-benzo[1,3]dioxole-2,2-dicarboxylic acid or a pharmaceutically acceptable salt thereof.

80. A method of treating diabetes in a mammal, the method comprising administering to a mammal in need thereof an effective amount of a compound of claim 1 or a pharmaceutically acceptable salt thereof, enantiomer thereof, racemic mixture thereof, or diastereomeric mixture thereof.

81. A method of treating diabetes in a mammal, the method comprising administering to a mammal in need thereof an effective amount of a compound of claim 78 or a pharmaceutically acceptable salt thereof, enantiomer thereof, racemic mixture thereof, or diastereomeric mixture thereof.

82. A method of treating obesity in a mammal, the method comprising administering to a mammal in need thereof an effective amount of compound of claim 1 or a pharmaceutically acceptable salt thereof, enantiomer thereof, racemic mixture thereof, or diastereomeric mixture thereof.

83. A method of treating obesity in a mammal, the method comprising administering to a mammal in need thereof an effective amount of compound of claim 78 or a pharmaceutically acceptable salt thereof, enantiomer thereof, racemic mixture thereof, or diastereomeric mixture thereof.

84. A method of treating hyperglycemia in a mammal, the method comprising administering to a mammal in need thereof an effective amount of a compound of claim 1 or a pharmaceutically acceptable salt thereof, enantiomer thereof, racemic mixture thereof, or diastereomeric mixture thereof.

85. A method of treating hyperglycemia in a mammal, the method comprising administering to a mammal in need thereof an effective amount of a compound of claim 78 or a pharmaceutically acceptable salt thereof, enantiomer thereof, racemic mixture thereof, or diastereomeric mixture thereof.

86. A pharmaceutical composition comprising an effective amount of a compound of claim 1, or a pharmaceutically acceptable salt thereof, enantiomer thereof, racemic mixture thereof, or diastereomeric mixture thereof, in combination with a pharmaceutically acceptable carrier.

87. A pharmaceutical composition comprising an effective amount of a compound of claim 78, or a pharmaceutically acceptable salt thereof, enantiomer thereof, racemic mixture thereof, or diastereomeric mixture thereof, in combination with a pharmaceutically acceptable carrier.

* * * * *